(12) United States Patent
Chen et al.

(10) Patent No.: US 10,913,954 B2
(45) Date of Patent: Feb. 9, 2021

(54) ABIOTIC STRESS TOLERANT PLANTS AND METHODS

(71) Applicants: PIONEER OVERSEAS CORPORATION, Johnston, IA (US); SINOBIOWAY BIO-AGRICULTURE GROUP CO., LTD., Beijing (CN)

(72) Inventors: Guangwu Chen, Beijing (CN); Chengfeng Du, Beijing (CN); Yang Gao, Beijing (CN); Shangwu Liang, Beijing (CN); Guihua Lu, Beijing (CN); Guanfan Mao, Beijing (CN); Xuguang Tan, Beijing (CN); Changgui Wang, Beijing (CN); Guokui Wang, Beijing (CN)

(73) Assignees: PIONEER OVERSEAS CORPORATION; SINOBIOWAY BIO-AGRICULTURE GROUP CO LTD

( * ) Notice: Subject to any disclaimer, the term of this patent is extended or adjusted under 35 U.S.C. 154(b) by 0 days.

(21) Appl. No.: 16/312,508

(22) PCT Filed: Jun. 29, 2017

(86) PCT No.: PCT/CN2017/090755
§ 371 (c)(1),
(2) Date: Dec. 21, 2018

(87) PCT Pub. No.: WO2018/001302
PCT Pub. Date: Jan. 4, 2018

(65) Prior Publication Data
US 2019/0177742 A1  Jun. 13, 2019

(30) Foreign Application Priority Data
Jun. 30, 2016 (CN) .......................... 2016 1 0507365

(51) Int. Cl.
*C12N 15/82* (2006.01)
*C12Q 1/6895* (2018.01)
*C07K 14/415* (2006.01)

(52) U.S. Cl.
CPC ........ *C12N 15/8273* (2013.01); *C07K 14/415* (2013.01); *C12N 15/827* (2013.01); *C12N 15/8261* (2013.01); *C12N 15/8271* (2013.01); *C12N 15/8274* (2013.01); *C12Q 1/6895* (2013.01); *C12Q 2600/158* (2013.01)

(58) Field of Classification Search
None
See application file for complete search history.

(56) References Cited

U.S. PATENT DOCUMENTS

| 6,417,428 B1 * | 7/2002 | Thomashow | C07K 14/395 435/6.14 |
| 7,135,616 B2 * | 11/2006 | Heard | C07K 14/415 800/278 |
| 2009/0100536 A1 | 4/2009 | Adams et al. | |

FOREIGN PATENT DOCUMENTS

CN   105338806 A   2/2016

OTHER PUBLICATIONS

Grafi et al. Methyl-CpG-binding domain (MBD) proteins in plants. Biochim Biophys Acta. May-Jun. 2007;1769(5-6):287-94. Epub Mar. 1, 2007. Review. (Year: 2007).*
Farrell. The Regulation of Gene Expression in Plants and Animals. Chapter 1 pp. 1-38 In Regulation of Gene Expression in Plants, Edited by Carole L. Bassett., 2007, Springer. (Year: 2007).*
Kim et al. A 20 nucleotide upstream element is essential for the nopaline synthase (nos) promoter activity. Plant Mol Biol. Jan. 1994; 24(1):105-17. (Year: 1994).*
Ha S.B.et al. Cis-acting regulatory elements controlling temporal and organ-specific activity of nopaline synthase promoter. Nucleic Acids Res. Jan. 11, 1989;17(1):215-23. (Year: 1989).*
Ullrich et al. Means to optimize protein expression in transgenic plants. Curr. Opin. Biotechnol. Apr. 2015;32:61-67. (Year: 2015).*
Predicted: *Oryza sativa* Japonica Group cytosolic isocitrate dehydrogenase[NADP] (LOC4327213), mRNA Accession No. XM_015758671.1 Genbank Mar. 1, 2016 (Mar. 1, 2016).
Yuan, Jin-Cheng, et al.: "Cloning and Character Analysis of NADP+-Dependent Isocitrate Dehydrogenase Gene in Maize", Plant Physiology Journal, Apr. 30, 2015 (Apr. 30, 2015), vol. 51, No. 4, pp. 481-487.
International Search Report for International Application No. PCT/CN2017/090755, dated Oct. 10, 2017.
International Written Opinion for International Application No. PCT/CN2017/090755, dated Oct. 10, 2017.

* cited by examiner

*Primary Examiner* — Cynthia E Collins

(57) ABSTRACT

Isolated polynucleotides and polypeptides, and recombinant DNA constructs are useful for conferring improved drought tolerance, and/or for regulating flowering time. Compositions (such as plants or seeds) comprise these recombinant DNA constructs; and methods utilize these recombinant DNA constructs. The recombinant DNA constructs comprise a polynucleotide operably linked to a promoter that is functional in a plant, wherein said polynucleotides encode drought tolerance polypeptides and/or flowering time-regulating polypeptide.

2 Claims, 7 Drawing Sheets
Specification includes a Sequence Listing.

ABIOTIC STRESS TOLERANT PLANTS AND METHODS

FIELD

The field of the disclosure relates to plant breeding and genetics and, particularly, relates to recombinant DNA constructs useful in plants for improving tolerance to abiotic stress, such as drought, and cold stress, and recombinant DNA constructs useful regulating flowering time and/or heading date of plants.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and have to adjust to the prevailing environmental conditions of their surroundings. This has led to their development of a great plasticity in gene regulation, morphogenesis, and metabolism. Adaption and defense strategies involve the activation of genes encoding proteins important in the acclimation or defense towards the different stresses.

Drought (insufficient available water) is one of the major abiotic stresses that limit crop productivity worldwide, and exposure of plants to a water-limiting environment during various developmental stages appear to activate various physiological and developmental changes. Genetic research has shown that drought tolerance is a quantitative trait, controlled by many genes. Molecular marker-assisted breeding has led to improved drought tolerance in crops. Transgenic approaches to engineering drought tolerance in crops have made progress (Vinocur B. and Altman A. (2005) Curr. Opin. Biotechnol. 16:123-132; Lawlor D W. (2013) J. Exp. Bot. 64:83-108).

SUMMARY

The following embodiments are among those encompassed by the disclosure:

In one embodiment, the present disclosure includes an isolated polynucleotide, comprising: (a) a polynucleotide with nucleotide sequence of at least 85% sequence identity to SEQ ID NO: 2, 5, 8, 11, 14, 17, 20 or 23; (b) a polynucleotide with nucleotide sequence of at least 85% sequence identity to SEQ ID NO: 3, 6, 9, 12, 15, 18, 21 or 24; (c) a polynucleotide encoding a polypeptide with amino acid sequence of at least 90% sequence identity to SEQ ID NO: 4, 7, 10, 13, 16, 19, 22 or 25; or (d) the full complement of the nucleotide sequence of (a), (b) or (c), wherein over-expression of the polynucleotide in a plant enhances drought tolerance; the isolated polynucleotide comprises the nucleotide sequence of SEQ ID NO: 2, 3, 5, 6, 8, 9, 11, 12, 14, 15, 17, 18, 20, 21, 23 or 24; and the said polypeptide comprises the amino acid sequence of SEQ ID NO: 4, 7, 10, 13, 16, 19, 22 or 25. Further, over-expression of the polynucleotide in a plant enhances the grain yield under normal conditions. Alteration the expression of the polynucleotide in a plant can regulate the flowering time, wherein increasing expression of the polynucleotide in plant promotes early flowering time; and reducing expression of the polynucleotide in plant delays flowering time. Over-expression of the polynucleotide in a plant enhances nitrogen stress tolerance or improves NUE.

In another embodiment, the present disclosure includes a recombinant DNA construct comprising the isolated polynucleotide operably linked to at least one heterologous regulatory element, wherein the polynucleotide comprises (a) a polynucleotide with nucleotide sequence of at least 85% sequence identity to SEQ ID NO: 2, 3, 5, 6, 8, 9, 11, 12, 14, 15, 17, 18, 20, 21, 23 or 24; (b) a polynucleotide encoding a polypeptide with amino acid sequence of at least 90% sequence identity to SEQ ID NO: 4, 7, 10, 13, 16, 19, 22 or 25; or (c) the full complement of the nucleotide sequence of (a) or (b).

In another embodiment, the present disclosure includes a modified plant or seed comprising an increased expression of at least one polynucleotide encoding a ICDH1, MtN3L, DN-DTP6, ANKL1, MBD2, TP1, ACOAT1, DN-DTP7 polypeptide compared to a control plant or seed, wherein the polynucleotide comprises (a) a polynucleotide with nucleotide sequence of at least 85% sequence identity to SEQ ID NO: 2, 3, 5, 6, 8, 9, 11, 12, 14, 15, 17, 18, 20, 21, 23 or 24; (b) a polynucleotide encoding a polypeptide with amino acid sequence of at least 90% sequence identity to SEQ ID NO: 4, 7, 10, 13, 16, 19, 22 or 25; or (c) the full complement of the nucleotide sequence of (a) or (b).

The modified plant comprises in its genome a recombinant DNA construct comprising a polynucleotide operably linked to at least one heterologous regulatory element, wherein the polynucleotide comprises (a) a polynucleotide with nucleotide sequence of at least 85% sequence identity to SEQ ID NO: 2, 3, 5, 6, 8, 9, 11, 12, 14, 15, 17, 18, 20, 21, 23 or 24; (b) a polynucleotide encoding a polypeptide with amino acid sequence of at least 90% sequence identity to SEQ ID NO: 4, 7, 10, 13, 16, 19, 22 or 25; or (c) the full complement of the nucleotide sequence of (a) or (b), wherein the said plant exhibits improved drought tolerance when compared to the control plant, and the said improved drought tolerance may be increased survival rate, reduced leaf rolling degree, improved seed setting rate, or increased grain yield under drought condition.

The plant comprises a modified regulatory element to increase the expression of the endogenous polynucleotide, wherein the polynucleotide comprises: (a) a polynucleotide with nucleotide sequence of at least 85% sequence identity to SEQ ID NO: 2, 5, 8, 11, 14, 17, 20 or 23; (b) a polynucleotide with nucleotide sequence of at least 85% sequence identity to SEQ ID NO: 3, 6, 9, 12, 15, 18, 21 or 24; (c) a polynucleotide encoding a polypeptide with amino acid sequence of at least 90% sequence identity to SEQ ID NO: 4, 7, 10, 13, 16, 19, 22 or 25; or (d) the full complement of the nucleotide sequence of (a), (b) or (c); wherein said plant exhibits improved drought tolerance when compared to the control plant.

The plant exhibits improved grain yield under normal conditions when compared to the control plant.

The plant exhibits early flowering time when compared to the control plant planted under the same conditions. Further, the plant exhibits early flowering time by about 6~11 days when compared to the control plant. Also, further, the plant is rice plant and is planted in a latitude of more than about 300 N.

The plant exhibits improved low nitrogen tolerance or NUE when compared to the control plant.

A modified plant comprising a reduced expression of a polynucleotide compared to a control plant, wherein the polynucleotide comprises: (a) a polynucleotide with nucleotide sequence of at least 85% sequence identity to SEQ ID NO: 14; (b) a polynucleotide with nucleotide sequence of at least 85% sequence identity to SEQ ID NO: 15; (c) a polynucleotide encoding a polypeptide with amino acid sequence of at least 90% sequence identity to SEQ ID NO: 16; or (d) the full complement of the nucleotide sequence of (a), (b) or (c); wherein the plant exhibits late flowering time when compared to the control plant planted under the same conditions.

In another embodiment, methods are provided for increasing drought tolerance in a plant, the method comprises increasing the expression of at least one polynucleotide encoding an ICDH1, MtN3L, DN-DTP6, ANKL1, MBD2, TP1, ACOAT1, DN-DTP7 polypeptide in the plant compared to a control plant, wherein the polynucleotide comprises: (a) a polynucleotide with nucleotide sequence of at least 85% sequence identity to SEQ ID NO: 2, 5, 8, 11, 14, 17, 20 or 23; (b) a polynucleotide with nucleotide sequence of at least 85% sequence identity to SEQ ID NO: 3, 6, 9, 12, 15, 18, 21 or 24; and (c) a polynucleotide encoding a polypeptide with amino acid sequence of at least 90% sequence identity to SEQ ID NO: 4, 7, 10, 13, 16, 19, 22 or 25. Wherein the obtained plant exhibits increased drought tolerance when compared to the control plant, and the said improved drought tolerance may be increased survival rate, reduced leaf rolling degree, improved seed setting rate, or increased grain yield under drought condition.

Further, the expression of the polynucleotide is increased by: (a) increasing the expression of the polynucleotide encoding an ICDH1, MtN3L, DN-DTP6, ANKL1, MBD2, TP1, ACOAT1, DN-DTP7 polypeptide in plant by a recombinant DNA construct, wherein the recombinant DNA construct comprises the polynucleotide encoding the ICDH1, MtN3L, DN-DTP6, ANKL1, MBD2, TP1, ACOAT1, DN-DTP7 polypeptide operably linked to at least one heterologous regulatory element, wherein the polynucleotide encodes the polypeptide having an amino acid sequence of at least 90% sequence identity compared to SEQ ID NO: 4, 7, 10, 13, 16, 19, 22 or 25; or (b) increasing the expression of an endogenous polynucleotide encoding the polypeptide having an amino acid sequence of at least 90% sequence identity compared to SEQ ID NO: 4, 7, 10, 13, 16, 19, 22 or 25.

In another embodiment, methods are provided for evaluating drought tolerance in a plant, comprising: (a) introducing into a regenerable plant cell a recombinant DNA construct comprising a polynucleotide operably linked to at least one heterologous regulatory element, wherein the polynucleotide encodes a polypeptide having an amino acid sequence of at least 80% sequence identity, when compared to SEQ ID NO: 4, 7, 10, 13, 16, 19, 22 or 25; (b) regenerating a transgenic plant from the regenerable plant cell after step (a), wherein the transgenic plant comprises in its genome the recombinant DNA construct; (c) obtaining a progeny plant derived from the transgenic plant, wherein the progeny plant comprises in its genome the recombinant DNA construct; and (d) evaluating the progeny plant for drought tolerance compared to the control plant not comprising the recombinant DNA construct.

In another embodiment, methods are provided for enhancing grain yield in a rice plant, when compared to a control plant, wherein the plant exhibits enhanced grain yield under normal and/or stress conditions, the method comprises the step of increasing the expression of the endogenous OsICDH1, OsMtN3L, OsDN-DTP6, OsANKL1, OsMBD2, OsTP1, OsACOAT1 or OsDN-DTP7 gene or a heterologous OsICDH1, OsMtN3L, OsDN-DTP6, OsANKL1, OsMBD2, OsTP1, OsACOAT1 or OsDN-DTP7 gene in the rice plant.

In another embodiment, methods of regulating flowering time in a rice plant are provided, the method comprises altering the expression of a polynucleotide encoding a MBD2 polypeptide in the rice plant. The polynucleotide comprises: (a) a polynucleotide with nucleotide sequence of at least 85% sequence identity to SEQ ID NO: 14; (b) a polynucleotide with nucleotide sequence of at least 85% sequence identity to SEQ ID NO: 15; and (c) a polynucleotide encoding a polypeptide with amino acid sequence of at least 90% sequence identity to SEQ ID NO: 16. The expression of the polynucleotide is altered by: (a) increasing the expression of the polynucleotide encoding a MBD2 polypeptide in plant by a recombinant DNA construct, wherein the recombinant DNA construct comprises the polynucleotide encoding the MBD2 polypeptide operably linked to at least one heterologous regulatory element, wherein the polynucleotide encodes the polypeptide having an amino acid sequence of at least 90% sequence identity compared to SEQ ID NO: 16; or (b) increasing or decreasing the expression of an endogenous polynucleotide encoding the polypeptide having an amino acid sequence of at least 90% sequence identity compared to SEQ ID NO: 16; or (c) decreasing the expression of the polynucleotide encoding a MBD2 polypeptide in plant by a recombinant DNA construct, wherein the recombinant DNA construct comprises a silencing element that down regulates the expression of an endogenous polynucleotide encoding the polypeptide having an amino acid sequence of at least 90% sequence identity compared to SEQ ID NO: 16. Further, the increased expression of the polynucleotide in the rice plant promotes early flowering time when compared to the control plant not having said increased expression; the increased expression of the polynucleotide in the rice plant promotes early flowering time by about 6~11 days when compared to the control plant not having said increased expression; reducing the expression level of the polynucleotide in the rice plant delays flowering time when compared to the control plant not having said reduced expression.

In another embodiment, methods of increasing low nitrogen tolerance or NUE in a plant are provided, the method comprises increasing the expression of at least one polynucleotide encoding a MtN3L or ANKL1 polypeptide in a plant compared to a control plant not having such increased expression, wherein the polynucleotide comprises: (a) a polynucleotide with nucleotide sequence of at least 85% sequence identity to SEQ ID NO: 5 or 11; (b) a polynucleotide with nucleotide sequence of at least 85% sequence identity to SEQ ID NO: 6 or 12; and (c) a polynucleotide encoding a polypeptide with amino acid sequence of at least 90% sequence identity to SEQ ID NO: 7 or 13. The expression of the polynucleotide is increased by: (a) increasing the expression of the polynucleotide encoding a MtN3L or ANKL1 polypeptide in plant by a recombinant DNA construct, wherein the recombinant DNA construct comprises the polynucleotide encoding the MtN3L or ANKL1 polypeptide operably linked to at least one heterologous regulatory element, wherein the polynucleotide encodes the polypeptide having an amino acid sequence of at least 90% sequence identity compared to SEQ ID NO: 7 or 13; or (b) increasing the expression of an endogenous polynucleotide encoding the polypeptide having an amino acid sequence of at least 90% sequence identity compared to SEQ ID NO: 7 or 13.

In another embodiment, methods are provided for making a plant in which the expression or the activity of an endogenous ICDH1, MtN3L, DN-DTP6, ANKL1, MBD2, TP1, ACOAT1 or DN-DTP7 polypeptide is increased, when compared to the activity of wild-type ICDH1, MtN3L, DN-DTP6, ANKL1, MBD2, TP1, ACOAT1 or DN-DTP7 polypeptide from a control plant, and wherein the plant exhibits at least one phenotype selected from the group consisting of: increased drought tolerance, increased grain yield, increased abiotic stress tolerance and increased biomass, compared to the control plant, wherein the method comprises the steps of (i) introducing a DNA fragment or deleting a DNA fragment or (ii) introducing one or more nucleotide changes in the genomic region comprising the endogenous ICDH1, MtN3L, DN-DTP6, ANKL1, MBD2, TP1, ACOAT1 or DN-DTP7 gene, wherein the change is effective for increasing the expression or the activity of the endogenous ICDH1, MtN3L, DN-DTP6, ANKL1, MBD2, TP1, ACOAT1 or DN-DTP7 polypeptide, wherein the change is introduced using zinc finger nuclease, Transcription Activator-Like Effector Nuclease (TALEN), CRISPR-cas, guided Cas endonuclease or meganuclease.

In another embodiment, plants comprising the DNA construct of this disclosure, wherein expression of the ICDH1, MtN3L, DN-DTP6, ANKL1, MBD2, TP1, ACOAT1 or DN-DTP7 gene is increased in the plant, when compared to the control plant, and wherein the plant exhibits at least one phenotype selected from the group consisting of: increased grain yield, increased abiotic stress tolerance and increased biomass, compared to the control plant, wherein the plant exhibits an increase in abiotic stress tolerance, and the abiotic stress is drought stress.

In another embodiment, the present disclosure includes any of the plants of the disclosure, wherein the plant is selected from the group consisting of rice, maize, soybean, sunflower, sorghum, canola, wheat, alfalfa, cotton, barley, millet, sugar cane and switchgrass.

In another embodiment, methods for identifying one or more alleles associated with increased grain yield in a population of rice plants, the method comprising: (a) detecting in a population of rice plants one or more polymorphisms in (i) a genomic region encoding a polypeptide or (ii) a regulatory region controlling expression of the polypeptide, wherein the polypeptide comprises the amino acid sequence selected from the group consisting of SEQ ID NO: 4, 7, 10, 13, 16, 19, 22 or 25, or a sequence that is 90% identical to SEQ ID NO: 4, 7, 10, 13, 16, 19, 22 or 25, wherein the one or more polymorphisms in the genomic region encoding the polypeptide or in the regulatory region controlling expression of the polypeptide is associated with grain yield; and (b) identifying one or more alleles at the one or more polymorphisms that are associated with increased grain yield, wherein the one or more alleles associated with increased grain yield is used for marker assisted selection of a rice plant with increased grain yield, the one or more polymorphisms is in the coding region of the polynucleotide, and the regulatory region is a promoter.

In another embodiment, the present disclosure concerns a recombinant DNA construct comprising any of the isolated polynucleotides of the present disclosure operably linked to at least one regulatory element, and a cell, a plant, or a seed comprising the recombinant DNA construct. The cell may be eukaryotic, e.g., a yeast, insect or plant cell; or prokaryotic, e.g., a bacterial cell.

BRIEF DESCRIPTION OF THE DRAWINGS AND SEQUENCE LISTING

The disclosure can be more fully understood from the following detailed description and the accompanying drawings and Sequence Listing which form a part of this application.

Figure 1:
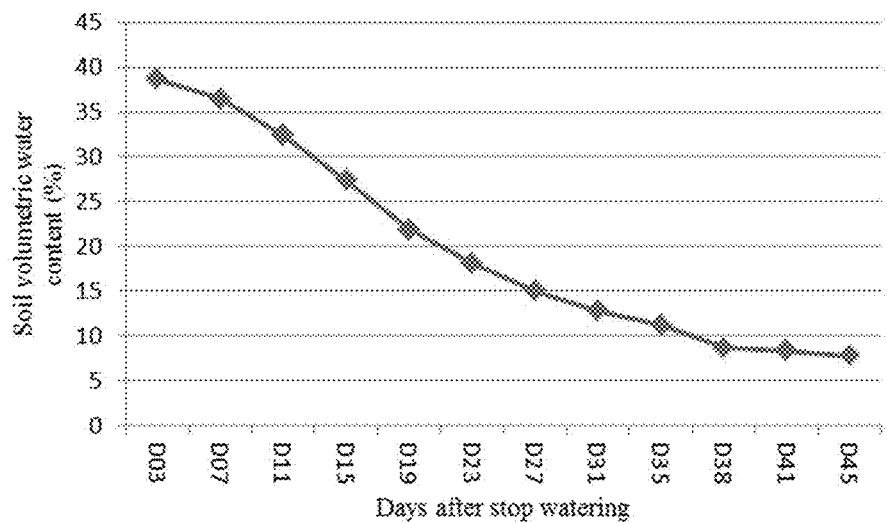
FIG. 1 shows changes of soil volumetric moisture content at different developmental stage in Hainan field in the first field experiment for drought testing OsICDH1 transgenic rice. The OsICDH1 transgenic rice started heading at 25 days after stopping watering.

Table 1. SEQ ID NOs for nucleotide and amino acid sequences provided in the sequence listing Table 2. Rice gene names, Gene IDs (from TIGR) and Construct IDs Table 3. Primers for cloning rice drought tolerance genes Table 4. PCR reaction mixture for cloning drought tolerance genes Table 5. PCR cycle conditions Table 6. Enhanced drought tolerance of OsICDH1 transgenic rice plants under greenhouse conditions (1$^{st}$ experiment)

Table 7. Enhanced drought tolerance of OsICDH1 transgenic rice plants under greenhouse conditions (2$^{nd}$ experiment)

Table 8. Enhanced drought tolerance of OsDN-DTP6 transgenic rice plants under greenhouse conditions Table 9. Enhanced drought tolerance of OsANKL1 transgenic rice plants under greenhouse conditions Table 10. Enhanced drought tolerance of OsMBD2 transgenic rice plants under greenhouse conditions Table 11. Enhanced drought tolerance of OsTP1 transgenic rice plants under greenhouse conditions (1$^{st}$ experiment)

Table 12. Enhanced drought tolerance of OsTP1 transgenic rice plants under greenhouse conditions (2$^{nd}$ experiment)

Table 13. Enhanced drought tolerance of OsACOAT1 transgenic rice plants under greenhouse conditions Table 14. Drought sensitive assay of OsDN-DTP7 transgenic rice plants under greenhouse conditions Table 15. Grain yield analysis of OsICDH1 transgenic rice plants under well-watered conditions Table 16. Grain yield analysis of OsANKL1 transgenic rice plants under well-watered conditions Table 17. Grain yield analysis of OsMBD2 transgenic rice plants under well-watered conditions Table 18. grain yield analysis of OsACOAT1 transgenic rice plants under well-watered conditions Table 19. grain yield analysis of OsDN-DTP7 transgenic rice plants under well-watered conditions Table 20. Grain yield analysis of OsICDH1 transgenic rice plants under field drought conditions (1$^{st}$ experiment)

Table 21. Grain yield analysis of OsICDH1 transgenic rice plants under field drought conditions (2$^{nd}$ experiment)

Table 22. Grain yield analysis of OsMtN3L transgenic rice plants under field drought conditions (1$^{st}$ experiment)

Table 23. Grain yield analysis of OsMtN3L transgenic rice plants under field drought conditions (2$^{nd}$ experiment)

Table 24. Grain yield analysis of OsDN-DTP6 transgenic rice plants under field drought conditions (1$^{st}$ experiment)

Table 25. Grain yield analysis of OsDN-DTP6 transgenic rice plants under field drought conditions (2$^{nd}$ experiment)

Table 26. Grain yield analysis of OsANKL1 transgenic rice plants under field drought conditions (1$^{st}$ experiment)

Table 27. Grain yield analysis of OsANKL1 transgenic rice plants under field drought conditions (2$^{nd}$ experiment)

Table 28. Grain yield analysis of OsMBD2 transgenic rice plants under field drought conditions (1$^{st}$ experiment)

Table 29. Grain yield analysis of OsMBD2 transgenic rice plants under field drought conditions (2$^{nd}$ experiment)

Table 30. Grain yield analysis of OsTP1 transgenic rice plants under field drought conditions (1$^{st}$ experiment)

Table 31. Grain yield analysis of OsTP1 transgenic rice plants under field drought conditions (2$^{nd}$ experiment)

Table 32. Grain yield analysis of OsACOAT1 transgenic rice plants under field drought conditions (1$^{st}$ experiment)

Table 33. Grain yield analysis of OsACOAT1 transgenic rice plants under field drought conditions (2$^{nd}$ experiment)

Table 34. Grain yield analysis of OsDN-DTP7 transgenic rice plants under field drought conditions (1$^{st}$ experiment)

Table 35. Grain yield analysis of OsDN-DTP7 transgenic rice plants under field drought conditions (2$^{nd}$ experiment)

Table 36. Paraquat tolerance assay of OsICDH1 transgenic rice plants (1$^{st}$ experiment)

Table 37. Paraquat tolerance assay of OsICDH1 transgenic rice plants (2$^{nd}$ experiment)

Table 38. Paraquat tolerance assay of OsMtN3L transgenic rice plants (1$^{st}$ experiment)

Table 39. Paraquat tolerance assay of OsMtN3L transgenic rice plants (2$^{nd}$ experiment)

Table 40. Paraquat tolerance assay of OsDN-DTP6 transgenic rice plants (1$^{st}$ experiment)

Table 41. Paraquat tolerance assay of OsDN-DTP6 transgenic rice plants (2$^{nd}$ experiment)

Table 42. Paraquat tolerance assay of OsANKL1 transgenic rice plants (1$^{st}$ experiment)

Table 43. Paraquat tolerance assay of OsANKL1 transgenic rice plants (2$^{nd}$ experiment)

Table 44. Paraquat tolerance assay of OsMBD2 transgenic rice plants (1$^{st}$ experiment)

Table 45. Paraquat tolerance assay of OsMBD2 transgenic rice plants (2$^{nd}$ experiment)

Table 46. Paraquat tolerance assay of OsTP1 transgenic rice plants (1$^{st}$ experiment)

Table 47. Paraquat tolerance assay of OsTP1 transgenic rice plants (2$^{nd}$ experiment)

Table 48. Paraquat tolerance assay of OsACOAT1 transgenic rice plants (1$^{st}$ experiment)

Table 49. Paraquat tolerance assay of OsACOAT1 transgenic rice plants (2$^{nd}$ experiment)

Table 50. Paraquat tolerance assay of OsDN-DTP7 transgenic rice plants (1$^{st}$ experiment)

Table 51. Paraquat tolerance assay of OsDN-DTP7 transgenic rice plants (2$^{nd}$ experiment)

Table 52. Flowering trait and grain yield of OsMBD2 transgenic rice plants in Ningxia (1$^{st}$ experiment)

Table 53. Flowering trait and grain yield of OsMBD2 transgenic rice plants in Ningxia (2$^{nd}$ experiment)

Table 54. Flowering trait and grain yield of OsMBD2 transgenic rice plants in Ningxia (3$^{rd}$ experiment)

Table 55. Grain yield analysis of OsMtN3L transgenic rice under field low nitrogen condition Table 56. Grain yield analysis of OsANKL1 (DP0960) transgenic rice under field low nitrogen condition Table 57. Chlorate sensitive assay of OsANKL1 transgenic rice seedlings (1$^{st}$ experiment)

Table 58. Chlorate sensitive assay of OsANKL1 transgenic rice seedlings (2$^{nd}$ experiment)

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Artificial | DP0158 vector | 1 | n/a |
| Oryza sativa | OsICDH1 | 2, 3 | 4 |
| Oryza sativa | OsMtN3L | 5, 6 | 7 |

TABLE 1-continued

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| Oryza sativa | OsDN-DTP6 | 8, 9 | 10 |
| Oryza sativa | OsANKL1 | 11, 12 | 13 |
| Oryza sativa | OsMBD2 | 14, 15 | 16 |
| Oryza sativa | OsTP1 | 17, 18 | 19 |
| Oryza sativa | OsACOAT1 | 20, 21 | 22 |
| Oryza sativa | OsDN-DTP7 | 23, 24 | 25 |
| Artificial | Primers | 26-57 | n/a |

The Sequence Listing contains the one-letter code for nucleotide sequences and the three-letter code for amino acid sequences as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. § 1.822.

SEQ ID NO: 1 is the nucleotide sequence of vector DP0158.

SEQ ID NO: 2 is the nucleotide sequence of cDNA of OsICDH1 gene.

SEQ ID NO: 3 is the nucleotide sequence of CDS of OsICDH1 gene.

SEQ ID NO: 4 is the amino acid sequence of OsICDH1 polypeptide.

SEQ ID NO: 5 is the nucleotide sequence of gDNA of OsMtN3L gene.

SEQ ID NO: 6 is the nucleotide sequence of CDS of OsMtN3L gene.

SEQ ID NO: 7 is the amino acid sequence of OsMtN3L polypeptide.

SEQ ID NO: 8 is the nucleotide sequence of gDNA of OsDN-DTP6 gene.

SEQ ID NO: 9 is the nucleotide sequence of CDS of OsDN-DTP6 gene.

SEQ ID NO: 10 is the amino acid sequence of OsDN-DTP6 polypeptide.

SEQ ID NO: 11 is the nucleotide sequence of gDNA of OsANKL1 gene.

SEQ ID NO: 12 is the nucleotide sequence of CDS of OsANKL1 gene.

SEQ ID NO: 13 is the amino acid sequence of OsANKL1 polypeptide.

SEQ ID NO: 14 is the nucleotide sequence of gDNA of OsMBD2 gene.

SEQ ID NO: 15 is the nucleotide sequence of CDS of OsMBD2 gene.

SEQ ID NO: 16 is the amino acid sequence of OsMBD2 polypeptide.

SEQ ID NO: 17 is the nucleotide sequence of gDNA of OsTP1 gene.

SEQ ID NO: 18 is the nucleotide sequence of CDS of OsTP1 gene.

SEQ ID NO: 19 is the amino acid sequence of OsTP1 polypeptide.

SEQ ID NO: 20 is the nucleotide sequence of cDNA of OsACOAT1 gene.

SEQ ID NO: 21 is the nucleotide sequence of CDS of OsACOAT1 gene.

SEQ ID NO: 22 is the amino acid sequence of OsACOAT1 polypeptide.

SEQ ID NO: 23 is the nucleotide sequence of cDNA of OsDN-DTP7 gene.

SEQ ID NO: 24 is the nucleotide sequence of CDS of OsDN-DTP7 gene.

SEQ ID NO: 25 is the amino acid sequence of OsDN-DTP7 polypeptide.

SEQ ID NO: 26 is forward primer for cloning cDNA of OsICDH1 gene.

SEQ ID NO: 27 is reverse primer for cloning cDNA of OsICDH1 gene.

SEQ ID NO: 28 is forward primer for cloning gDNA of OsMtN3L gene.

SEQ ID NO: 29 is reverse primer for cloning gDNA of OsMtN3L gene.

SEQ ID NO: 30 is forward primer for cloning gDNA of OsDN-DTP6 gene.

SEQ ID NO: 31 is reverse primer for cloning gDNA of OsDN-DTP6 gene.

SEQ ID NO: 32 is forward primer for cloning gDNA of OsANKL1 gene.

SEQ ID NO: 33 is reverse primer for cloning gDNA of OsANKL1 gene.

SEQ ID NO: 34 is forward primer for cloning gDNA of OsMBD2 gene.

SEQ ID NO: 35 is reverse primer for cloning gDNA of OsMBD2 gene.

SEQ ID NO: 36 is forward primer for cloning gDNA of OsTP1 gene.

SEQ ID NO: 37 is reverse primer for cloning gDNA of OsTP1 gene.

SEQ ID NO: 38 is forward primer for cloning cDNA of OsACOAT1 gene.

SEQ ID NO: 39 is reverse primer for cloning cDNA of OsACOAT1 gene.

SEQ ID NO: 40 is forward primer for cloning cDNA of OsDN-DTP7 gene.

SEQ ID NO: 41 is reverse primer for cloning cDNA of OsDN-DTP7 gene.

SEQ ID NO: 42 is forward primer for real-time RT-PCR analysis of OsICDH1 gene.

SEQ ID NO: 43 is reverse primer for real-time RT-PCR analysis of OsICDH1 gene.

SEQ ID NO: 44 is forward primer for real-time RT-PCR analysis of OsMtN3L gene.

SEQ ID NO: 45 is reverse primer for real-time RT-PCR analysis of OsMtN3L gene.

SEQ ID NO: 46 is forward primer for real-time RT-PCR analysis of OsDN-DTP6 gene.

SEQ ID NO: 47 is reverse primer for real-time RT-PCR analysis of OsDN-DTP6 gene.

SEQ ID NO: 48 is forward primer for real-time RT-PCR analysis of OsANKL1 gene.

SEQ ID NO: 49 is reverse primer for real-time RT-PCR analysis of OsANKL1 gene.

SEQ ID NO: 50 is forward primer for real-time RT-PCR analysis of OsMBD2 gene.

SEQ ID NO: 51 is reverse primer for real-time RT-PCR analysis of OsMBD2 gene.

SEQ ID NO: 52 is forward primer for real-time RT-PCR analysis of OsTP1 gene.

SEQ ID NO: 53 is reverse primer for real-time RT-PCR analysis of OsTP1 gene.

SEQ ID NO: 54 is forward primer for real-time RT-PCR analysis of OsACOAT1 gene.

SEQ ID NO: 55 is reverse primer for real-time RT-PCR analysis of OsACOAT1 gene.

SEQ ID NO: 56 is forward primer for real-time RT-PCR analysis of OsDN-DTP7 gene.

SEQ ID NO: 57 is reverse primer for real-time RT-PCR analysis of OsDN-DTP7 gene.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsICDH1 (NADP-dependent isocitrate dehydrogenase)" refers to a rice polypeptide that confers drought tolerance phenotype and is encoded by the rice gene locus LOC_Os01g14580.1. "ICDH1 polypeptide" refers herein to the OsICDH1 polypeptide and its homologs from other organisms.

The OsICDH1 polypeptide (SEQ ID NO: 4) is encoded by the coding sequence (CDS) (SEQ ID NO: 3) or nucleotide sequence (SEQ ID NO: 2) at rice gene locus LOC_Os01g14580.1. This polypeptide is annotated as "dehydrogenase, putative, expressed" in TIGR (the internet at plant biology msu.edu/index.shtml) and is annotated as "NADP-dependent isocitrate dehydrogenase" in NCBI (on the world web at ncbi.nlm.nih.gov), however does not have any prior assigned function.

The term "OsMtN3L (MtN3-Like protein)" refers to a rice polypeptide that confers drought tolerance and is encoded by the rice gene locus LOC_Os01g40960.1. "MtN3L polypeptide" refers herein to the OsMtN3L polypeptide and its homologs from other organisms.

The OsMtN3L polypeptide (SEQ ID NO: 7) is encoded by the coding sequence (CDS) (SEQ ID NO: 6) or nucleotide sequence (SEQ ID NO: 5) at rice gene locus LOC_Os01g40960.1. This polypeptide is annotated as "Nodulin MtN3 family protein, putative, expressed" in TIGR and "MtN3-like" in NCBI, however does not have any prior assigned function.

The term "OsDN-DTP6 (drought tolerance protein 6)" refers to a rice polypeptide that confers drought tolerance and is encoded by the rice gene locus LOC_Os09g15190.1. "DN-DTP6 polypeptide" refers herein to the OsDN-DTP6 polypeptide and its homologs from other organisms.

The OsDN-DTP6 polypeptide (SEQ ID NO: 10) is encoded by the coding sequence (CDS) (SEQ ID NO: 9) or nucleotide sequence (SEQ ID NO: 8) at rice gene locus LOC_Os09g15190.1. This polypeptide is annotated as "expressed protein" in TIGR.

The term "OsANKL1 (Ankyrin like protein)" refers to a rice polypeptide that confers drought tolerance phenotype and is encoded by the rice gene locus LOC_Os09g15200.1. "ANKL1 polypeptide" refers herein to the OsANKL1 polypeptide and its homologs from other organisms.

The OsANKL1 polypeptide (SEQ ID NO: 13) is encoded by the coding sequence (CDS) (SEQ ID NO: 12) or nucleotide sequence (SEQ ID NO: 11) at rice gene locus LOC_Os09g15200.1. This polypeptide is annotated as "ankyrin repeat family protein, putative, expressed" in TIGR and is annotated as "ankyrin-like protein" in NCBI, however does not have any prior assigned function.

The term "OsMBD2 (Methyl-binding domain protein MBD2)" refers to a rice polypeptide that confers drought tolerance and regulates rice flowering traits and is encoded by the rice gene locus LOC_Os06g48870.1. "MBD2 polypeptide" refers herein to the OsMBD2 polypeptide and its homologs from other organisms.

The OsMBD2 polypeptide (SEQ ID NO: 16) is encoded by the coding sequence (CDS) (SEQ ID NO: 15) or nucleotide sequence (SEQ ID NO: 14) at rice gene locus LOC_Os06g48870.1. This polypeptide is annotated as "Methyl-binding domain protein MBD, putative, expressed" in TIGR.

The term "OsTP1 (trehalose phosphatase 1)" refers to a rice polypeptide that confers drought tolerance and is encoded by the rice gene locus LOC_Os05g03810.1. "TP1 polypeptide" refers herein to the OsTP1 polypeptide and its homologs from other organisms.

The OsTP1 polypeptide (SEQ ID NO: 19) is encoded by the coding sequence (CDS) (SEQ ID NO: 18) or nucleotide sequence (SEQ ID NO: 17) at rice gene locus LOC_Os05g03810.1. This polypeptide is annotated as "trehalose phosphatase, putative, expressed" in TIGR.

The term "OsACOAT1 (acetylornithine aminotransferase)" refers to a rice polypeptide that confers drought tolerance phenotype and is encoded by the rice gene locus LOC_Os05g03830.1. "ACOAT1 polypeptide" refers herein to the OsACOAT1 polypeptide and its homologs from other organisms.

The OsACOAT1 polypeptide (SEQ ID NO: 22) is encoded by the coding sequence (CDS) (SEQ ID NO: 21) or nucleotide sequence (SEQ ID NO: 20) at rice gene locus LOC_Os05g03830.1. This polypeptide is annotated as "aminotransferase, putative, expressed" in TIGR, and is annotated as "acetylornithine aminotransferase" in NCBI.

The term "OsDN-DTP7 (drought tolerance protein 7)" refers to a rice polypeptide that confers drought tolerance phenotype and is encoded by the rice gene locus LOC_Os03g15720.1. "DN-DTP7 polypeptide" refers herein to the OsDN-DTP7 polypeptide and its homologs from other organisms.

The OsDN-DTP7 polypeptide (SEQ ID NO: 25) is encoded by the coding sequence (CDS) (SEQ ID NO: 24) or nucleotide sequence (SEQ ID NO: 23) at rice gene locus LOC_Os03g15720.1. This polypeptide is annotated as "expressed protein" in TIGR.

The terms "monocot" and "monocotyledonous plant" are used interchangeably herein. A monocot of the current disclosure includes plants of the Gramineae family.

The terms "dicot" and "dicotyledonous plant" are used interchangeably herein. A dicot of the current disclosure includes the following families: Brassicaceae, Leguminosae, and Solanaceae.

"Flowering" refers to the process of anthesis, i.e. glume dehiscent and anthers scattering under suitable temperature and humidity, or the process of flower formation.

Herein flowering is used to refer the process from young panicle differentiation, maturation, to the panicle heading.

"Flower development" or "floral development" is intended to mean the development of a flower or inflorescence from the initiation of the floral meristem to the development of the mature flower.

"Reproductive development" is intended to mean the development of a flower or inflorescence from the initiation of the floral meristem through pollination and the development of mature fruit.

Plants having an "early flowering time" as used herein are plants which start to flower earlier than control plants. Hence this term refers to plants that show an earlier start of flowering. Flowering time of plants can be assessed by counting the number of days (time to flower) between sowing and the emergence of a first inflorescence. The "flowering time" of a plant can for instance be determined using the method as described in WO 2007/093444.

"Heading" used herein refers the process of cereal panicle extended from flag leaf sheath "Heading date" and "heading time" are used interchangeably herein, and refers to the number of days from the day of seeding to the day when 50% young panicle of an individual plant head out the flag leaf sheath. Heading date is an important agronomic trait, which is under the regulation of basic nutritional genes and photoperiod-sensitivity genes and plays a key role in the adaptation and geo-graphic distribution of rice varieties. Appropriate heading date is a prerequisite for attaining the desired yield level.

The rice panicle will flower after the panicle headed out under normal condition. Herein heading date will be used to indicate the flowering time.

"Plant height" as used herein refers to the height from the surface of the field to the top of the highest panicle or leaf of an individual plant.

The terms "full complement" and "full-length complement" are used interchangeably herein, and refer to a complement of a given nucleotide sequence, wherein the complement and the nucleotide sequence consist of the same number of nucleotides and are 100% complementary.

The term "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

Increased biomass can be measured, for example, as an increase in plant height, plant total leaf area, plant fresh weight, plant dry weight or plant seed yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products. Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits, such as in the forms of greater yield or improved screening.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

In this disclosure, ZH11-TC and DP0158 indicate control plants, ZH11-TC represents rice plants generated from tissue cultured Zhonghua 11, and DP0158 represent plants transformed with empty vector of DP0158.

"Genome" as it applies to plant cells encompasses not only chromosomal DNA found within the nucleus, but also organelle DNA found within subcellular components (e.g., mitochondria, plastid) of the cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc. "Heterologous" with respect to sequence means a sequence that originates from a foreign species, or, if from the same species, is substantially modified from its native form in composition and/or genomic locus by deliberate human intervention. "Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases.

Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Messenger RNA (mRNA)" refers to the RNA which has no intron and can be translated into protein by the cell.

"cDNA" refers to a DNA that is complementary to and synthesized from an mRNA template using reverse transcriptase. The cDNA can be single-stranded or converted into the double-stranded form using the Klenow fragment of DNA polymerase I.

"Mature" protein refers to a post-translationally processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogonous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

The terms "entry clone" and "entry vector" are used interchangeably herein.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type. "Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel. (1992) *Plant Phys.* 100:1627-1632). A "mitochondrial signal peptide" is an amino acid sequence which directs a precursor protein into the mitochondria (Zhang and Glaser. (2002) *Trends Plant Sci* 7:14-21).

DNA nucleases and other mutation enzyme domains may be fused with DNA binding domains to produce the double strand break (DSBs) in the target DNA. DNA binding domains include, for example, an array specific DNA binding domain or a site-specific DNA binding domain. Site specific DNA binding domains include but are not limited to a TAL (Transcription Activator-Like Effector) or a zinc finger binding domain.

Examples of DNA-binding domains fused to DNA nucleases include but are not limited to TALEN and multiple TALENs. Transcription Activator-Like Effector Nucleases (TALENs) are artificial restriction enzymes generated by fusing the TAL effector DNA binding domain to a DNA enzyme domain. TAL proteins are produced by bacteria and include a highly conserved 33-34 amino acid DNA binding domain sequence (PCT publication No. WO2014127287; US Patent Publication No. US20140087426).

The original TALEN chimera was prepared using the wild-type Fok1 endonuclease domain. However, TALEN may also include chimera made from Fok1 endonuclease domain variants with mutations designed to improve cleavage specificity and cleavage activity. In some instances, multiple TALENs can be expressed to target multiple genomic regions.

A zinc finger is another type of DNA binding domain that can be used for introducing mutations into the target DNA.

Various protein engineering techniques can be used to alter the DNA-binding specificity of zinc fingers and tandem repeats of such engineered zinc fingers can be used to target desired genomic DNA sequences. Fusing a second protein domain such as a transcriptional repressor to a zinc finger that can bind near the promoter of the YEP gene can change the expression levels of ICDH1, MtN3L, DN-DTP6, ANKL1, MBD2, TP1, ACOAT1 or DN-DTP7 gene.

In one embodiment, a regulatory element driving the endogenous gene expression or the coding sequence itself, for example, may be edited or inserted into a plant by genome editing using a CRISPR/Cas9 system.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

Cas gene relates to a gene that is generally coupled, associated or close to or in the vicinity of flanking CRISPR loci. The terms "Cas gene", "CRISPR-associated (Cas) gene" are used interchangeably herein. (Haft et al. (2005) Computational Biology, PLoS Comput Biol 1(6): e60. doi: 10.1371/journal.pcbi.0010060). As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by a guide polynucleotide to recognize and optionally introduce a double strand break at a specific target site into the genome of a cell (U.S. 2015/0082478). The guide polynucleotide/Cas endonuclease system includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA if a correct protospacer-adjacent motif (PAM) is approximately oriented at the 3' end of the target sequence. The Cas endonuclease can be introduced directly into a cell by any method known in the art, for example, but not limited to transient introduction methods, transfection and/or topical application.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site (U.S. 2015/0082478). The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Methods to determine the relationship of various polynucleotide and polypeptide sequences are known. As used herein, "reference sequence" is a defined sequence used as a basis for sequence comparison. A reference sequence may be a subset or the entirety of a specified sequence, such as a segment of a full-length cDNA or gene sequence, or may be the complete cDNA or gene sequence. As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100 or longer. Those of skill in the art understand that to avoid a high similarity to a reference sequence due to inclusion of gaps in the sequence, a gap penalty is typically introduced and is subtracted from the number of matches.

Alignments using these programs can be performed using the default parameters. The CLUSTAL program is well described by Higgins, et al. (1988) *Gene* 73:237-244; Higgins, et al. (1989) *CABIOS* 5:151-153; Corpet, et al. (1988) *Nucleic Acids Res.* 16:10881-10890; Huang, et al. (1992) *CABIOS* 8:155-165 and Pearson, et al. (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al. (1990) *J. Mol. Biol.* 215:403 are based on the algorithm of Karlin and Altschul. (1990) supra. BLAST nucleotide searches can be performed with the BLASTN program, score=100, wordlength=12, to obtain nucleotide sequences homologous to a nucleotide sequence encoding a protein of the disclosures. BLAST protein searches can be performed with the BLASTX program, score=50, wordlength=3, to obtain amino acid sequences homologous to a protein or polypeptide of the disclosures. To obtain gapped alignments for comparison purposes, Gapped BLAST (in BLAST 2.0) can be utilized as described in Altschul, et al. (1997) *Nucleic Acids Res.* 25:3389. Alternatively, PSI-BLAST (in BLAST 2.0) can be used to perform an iterated search that detects distant relationships between molecules (Altschul, et al. (1997) supra). When utilizing BLAST, Gapped BLAST, PSI-BLAST and the default parameters of the respective programs (e.g., BLASTN for nucleotide sequences, BLASTX for proteins) can be used (the National Center for Biotechnology Information of the National Library of Medicine of the National Institutes of Health of the U.S. government). Alignment may also be performed by manual inspection.

Paired sequence identity/similarity values can be obtained using GAP Version 10 with the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch. (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

Unless stated otherwise, multiple alignments of the sequences provided herein are performed using the Clustal V method of alignment (Higgins and Sharp. (1989) *CABIOS*. 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

As used herein, "sequence identity" or "identity" in the context of two polynucleotides or polypeptide sequences make reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, and recombinant DNA constructs useful for conferring drought tolerance; compositions (such as plants or seeds) comprising these recombinant DNA constructs; and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16, 19, 22 or 25; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. Over-expression of the encoded polypeptide increases plant drought tolerance, and/or paraquat tolerance activity. Over-expression of the encoded polypeptide increases plant grain yield under normal conditions.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16, 19, 22 or 25. The polypeptide is preferably a drought tolerance polypeptide. Over-expression of the polypeptide increases plant drought tolerance and/or paraquat tolerance activity. Over-expression of the encoded polypeptide increases plant grain yield under normal conditions.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15, 18, 21 or 24; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 2, 5, 8, 11, 14, 17, 20 or 23; or (iii) a full complement of the nucleic acid sequence of (i) or (ii). Any of the foregoing isolated polynucleotides may be utilized in any recombinant DNA constructs of the present disclosure. The isolated polynucleotide preferably encodes a drought tolerance polypeptide. Over-expression of the polypeptide improves plant drought tolerance and/or paraquat tolerance activity. Over-expression of the encoded polypeptide increases plant grain yield under normal conditions.

An isolated polynucleotides are provided comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 16; or (ii) a full complement of the nucleic acid sequence of (i), wherein the full complement and the nucleic acid sequence of (i) consist of the same number of nucleotides and are 100% complementary. Over-expression of the encoded polypeptide promotes the transition from vegetative growth to reproductive growth.

An isolated polypeptides are provided having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 16. The polypeptides are MBD2 which can regulate the flowering time.

An isolated polynucleotide are provided comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 14 or 15; or (ii) a full complement of the nucleic acid sequence of (i). The isolated polynucleotide preferably encodes a protein which can regulate the flowering time. Over-expression of this polynucleotide promotes the transition from vegetative growth to reproductive growth; reducing the expression level of the polynucleotide prolongs time of transition from vegetative growth to reproductive growth.

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 7 or 13; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. Over-expression of the encoded polypeptide increases plant low nitrogen tolerance or NUE.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 7 or 13. Over-expression of the polypeptide increases plant low nitrogen tolerance or NUE.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 6 or 12; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 5 or 11; or (iii) a full complement of the nucleic acid sequence of (i) or (ii). Any of the foregoing isolated polynucleotides may be utilized in any recombinant DNA constructs of the present disclosure. Over-expression of the polypeptide improves plant low nitrogen tolerance or NUE.

Recombinant DNA Constructs and Suppression DNA Constructs:

In one aspect, the present disclosure includes recombinant DNA constructs (including suppression DNA constructs).

In one embodiment, a recombinant DNA construct comprises a polynucleotide operably linked to at least one regulatory element (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16, 19, 22 or 25; or (ii) a full complement of the nucleic acid sequence of (i).

In another embodiment, a recombinant DNA construct comprises a polynucleotide operably linked to at least one regulatory element (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 3, 6, 9, 12, 15, 18, 21 or 24; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 2, 5, 8, 11, 14, 17, 20 or 23; or (iii) a full complement of the nucleic acid sequence of (i) or (ii).

In another embodiment, a recombinant DNA construct comprises a polynucleotide operably linked to at least one regulatory element (e.g., a promoter functional in a plant), wherein said polynucleotide encodes a drought tolerance polypeptide. The polypeptide preferably has drought tolerance, low nitrogen tolerance and/or paraquat tolerance activity. The polypeptide may be from, for example, *Oryza sativa*, *Arabidopsis thaliana*, *Zea mays*, *Glycine max*, *Glycine tabacina*, *Glycine soja* or *Glycine tomentella*.

In another embodiment, a recombinant DNA construct comprises a polynucleotide operably linked to at least one regulatory element (e.g., a promoter functional in a plant), wherein said polynucleotide encodes a MBD2 protein. This polypeptide regulates flowering time, and may be from, for example, *Oryza sativa*, *Oryza australiensis*, *Oryza barthii*, *Oryza glaberrima* (African rice), *Oryza latifolia*, *Oryza longistaminata*, *Oryza meridionalis*, *Oryza officinalis*, *Oryza punctata*, *Oryza rufipogon* (brownbeard or red rice), *Oryza nivara* (Indian wild rice), *Arabidopsis thaliana*, *Zea mays*, *Glycine max*, *Glycine tabacina*, *Glycine soja* or *Glycine tomentella*.

In another aspect, the present disclosure includes suppression DNA constructs.

A suppression DNA construct may comprise at least one regulatory element (e.g., a promoter functional in a plant) operably linked to (a) all or part of: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 16, or (ii) a full complement of the nucleic acid sequence of (a)(i); or (b) a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to said all or part of a sense strand or antisense strand from which said region is derived, and wherein said target gene of interest encodes a flowering time-regulating polypeptide MBD2; or (c) all or part of: (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 15, or (ii) a full complement of the nucleic acid sequence of (c)(i). The suppression DNA construct may comprise a cosuppression construct, antisense construct, viral-suppression construct, hairpin suppression construct, stem-loop suppression construct, double-stranded RNA-producing construct, RNAi construct, or small RNA construct (e.g., an siRNA construct or an miRNA construct).

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive of, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (for example, U.S. Pat. No. 5,107,065). The complementarity of an antisense RNA may be with respect to any part of the specific gene transcript, i.e., at the 5' non-coding sequence, 3' non-coding sequence, introns, or the coding sequence.

RNA interference (RNAi) refers to the process of sequence-specific post-transcriptional gene silencing (PTGS) in animals mediated by short interfering RNAs (siRNAs) (Fire et al. (1998) Nature 391:806). The corresponding process in plants is commonly referred to as PTGS or RNA silencing and is also referred to as quelling in fungi. The process of PTGS is thought to be an evolutionarily-conserved cellular defense mechanism used to prevent the expression of foreign genes and is commonly shared by diverse flora and phyla (Fire et al. (1999) Trends Genet. 15:358).

Small RNAs play an important role in controlling gene expression, for example, small RNAs regulate many developmental processes which include flowering. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to 24 nucleotides (nt) in length that have been identified in both animals and plants (Lagos-Quintana et al. (2001) *Science* 294:853-858, Lagos-Quintana et al. (2002) *Curr. Biol.* 12:735-739; Lau et al. (2001) *Science* 294:858-862; Lee and Ambros. (2001) *Science* 294:862-864; Llave et al. (2002) *Plant Cell* 14:1605-1619; Mourelatos et al. (2002) *Genes Dev.* 16:720-728; Park et al. (2002) *Curr. Biol.* 12:1484-1495; Reinhart et al. (2002) *Genes Dev.* 16: 1616-1626). They are processed from longer precursor transcripts that range in size from approximately 70 to 200 nt, and these precursor transcripts have the ability to form stable hairpin structures.

miRNAs appear to regulate target genes by binding to complementary sequences located in the transcripts produced by these genes. It seems likely that miRNAs can enter at least two pathways of target gene regulation: (1) translational inhibition; and (2) RNA cleavage. miRNAs entering the RNA cleavage pathway are analogous to the 21-25 nt siRNAs generated during RNAi in animals and PTGS in plants, and likely are incorporated into an RNA-induced silencing complex (RISC) that is similar or identical to that seen for RNAi.

Regulatory Elements:

A recombinant DNA construct (including a suppression DNA construct) of the present disclosure may comprise at least one regulatory element.

A regulatory element may be a promoter or enhancer.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) *Plant J.* 12(2):255-265; Kwon et al. (1994) *Plant Physiol.* 105:357-367; Yamamoto et al. (1994) *Plant Cell Physiol.* 35(5):773-778; Gotor et al. (1993) *Plant J.* 3:509-518; Orozco et al. (1993) *Plant Mol. Biol.* 23(6): 1129-1138; and Matsuoka et al. (1993) *Proc. Natl. Acad. Sci. USA* 90(20):9586-9590).

Promoters which are seed or embryo-specific and may be useful in the disclosure include soybean Kunitz trypsin inhibitor (Kti3, Jofuku and Goldberg. (1989) *Plant Cell* 1:1079-1093), convicilin, vicilin, and legumin (pea cotyledons) (Rerie, W. G., et al. (1991) *Mol. Gen. Genet.* 259: 149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7: L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in certain embodiments include the following: 1) the stress-inducible promoter RD29A (Kasuga et al. (1999) *Nature Biotechnol.* 17:287-291); 2) the stress-inducible promoter Rab17 (Vilardell et al. (1991) *Plant Mol. Bio.* 17:985-993; Kamp Busk et al. (1997) *Plant J* 11(6): 1285-1295); 3) the barley promoter B22E whose expression is specific to the pedicel in developing maize kernels ("Primary Structure of a Novel Barley Gene Differentially Expressed in Immature Aleurone Layers". Klemsdal, S. S. et al. (1991) *Mol. Gen. Genet.* 228(1/2):9-16); and 4) maize promoter Zag2 ("Identification and molecular characterization of ZAG1, the maize homolog of the *Arabidopsis* floral homeotic gene AGAMOUS", Schmidt, R. J. et al. (1993) *Plant Cell* 5(7):729-737; "Structural characterization, chromosomal localization and phylogenetic evaluation of two pairs of AGAMOUS-like MADS-box genes from maize", Theissen et al. (1995) *Gene* 156(2):155-166; NCBI Gen- Bank Accession No. X80206)). Zag2 transcripts can be detected 5 days prior to pollination to 7 to 8 days after pollination ("DAP"), and directs expression in the carpel of developing female inflorescences and CimI which is specific to the nucleus of developing maize kernels. CimI transcript is detected 4 to 5 days before pollination to 6 to 8 DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, CimI that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006), the maize ROOTMET2 promoter (WO005063998, published Jul. 14, 2005), the CR1BIO promoter (WO006055487, published May 26, 2006), the CRWAQ81 (WO005035770, published Apr. 21, 2005) and the maize ZRP2.47 promoter (NCBI accession number: U38790; GI No. 1063664).

Recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

Any plant can be selected for the identification of regulatory elements and polypeptide genes to be used in recombinant DNA constructs of the present disclosure. Examples of suitable plant targets for the isolation of genes and regulatory elements would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, vine, watermelon, wheat, yams, and zucchini.

Compositions:

A composition of the present disclosure is a plant comprising in its genome any of the recombinant DNA constructs (including any of the suppression DNA constructs) of the present disclosure (such as any of the constructs discussed above). Compositions also include any progeny of the plant, and any seed obtained from the plant or its progeny, wherein the progeny or seed comprises within its genome the recombinant DNA construct (or suppression DNA construct). Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct (or suppression DNA construct). These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant.

Particular embodiments include but are not limited to the following:

1. A transgenic plant (for example, a rice or maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4, 7, 10, 13, 16, 19, 22 or 25, and wherein said plant exhibits increased drought tolerance and/or paraquat tolerance when compared to a control plant. The plant may further exhibit an alteration of at least one agronomic characteristic when compared to the control plant.

2. A transgenic plant (for example, a rice or maize or soybean plant) comprising in its genome a recombinant DNA construct comprising a polynucleotide operably linked to at least one regulatory element, wherein said polynucleotide encodes a polypeptide, and wherein said plant exhibits increased drought tolerance and/or paraquat tolerance when compared to a control plant. The plant may further exhibit an alteration of at least one agronomic characteristic when compared to the control plant.

3. A transgenic plant (for example, a rice or maize or soybean plant) comprising in its genome a recombinant DNA construct comprising a polynucleotide operably linked to at least one regulatory element, wherein said polynucleotide encodes a polypeptide, and wherein said plant exhibits an alteration of at least one agronomic characteristic when compared to a control plant.

4. A transgenic plant (for example, a rice or maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 16, and wherein said plant exhibits earlier flowering time when compared to a control plant. The plant may further exhibit an alteration of at least one agronomic characteristic when compared to the control plant.

5. A transgenic plant (for example, a rice or maize or soybean plant) comprising in its genome a suppression DNA construct comprising at least one regulatory element operably linked to a region derived from all or part of a sense strand or antisense strand of a target gene of interest, said region having a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to said all or part of a sense strand or antisense strand from which said region is derived, and wherein said target gene of interest encodes a flowering time-regulating polypeptide, and wherein said plant exhibits delayed flowering time when compared to a control plant.

6. A transgenic plant (for example, a rice or maize or soybean plant) comprising in its genome a suppression DNA construct comprising at least one regulatory element operably linked to all or part of (a) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 16; or (b) a full complement of the nucleic acid sequence of (a), and wherein said plant exhibits delayed flowering time when compared to a control plant.

7. Any progeny of the above plants in embodiment 1-6, any seeds of the above plants in embodiment 1-6, any seeds of progeny of the above plants in embodiment 1-6, and cells from any of the above plants in embodiment 1-6 and progeny thereof.

In any of the foregoing embodiment 1-7 or other embodiments, the drought tolerance polypeptide may be from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Zea mays, Glycine max, Glycine tabacina, Glycine soja* or *Glycine tomentella*.

In any of the foregoing embodiment 1-7 or other embodiments, the recombinant DNA construct (or suppression DNA construct) may comprise at least a promoter functional in a plant as a regulatory element.

In any of the foregoing embodiment 1-7 or other embodiments, the alteration of at least one agronomic characteristic is either an increase or decrease.

In any of the foregoing embodiment 1-7 or other embodiments, the at least one agronomic characteristic may be selected from the group consisting of greenness, grain yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress. For example, the alteration of at least one agronomic characteristic may be an increase in grain yield, greenness or biomass.

In any of the foregoing embodiment 1-7 or other embodiments, the plant may exhibit the alteration of at least one agronomic characteristic when compared, under water limiting conditions, to a control plant.

In any of the foregoing embodiment 1-7 or other embodiments, the plant may exhibit the alteration of at least one agronomic characteristic when compared, under oxidative stress (paraquat) conditions, to a control plant.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that over-expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Environmental conditions" refer to conditions under which the plant is grown, such as the availability of water, availability of nutrients, or the presence of insects or disease.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

The Examples below describe some representative protocols and techniques for simulating drought conditions and/or evaluating drought tolerance; simulating oxidative conditions.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration. One of ordinary skill in the art would readily recognize a suitable control or reference plant to be utilized when assessing or measuring an agronomic characteristic or phenotype of a transgenic plant using compositions or methods as described herein. For example, by way of non-limiting illustrations:

1. Progeny of a transformed plant which is hemizygous with respect to a recombinant DNA construct (or suppression DNA construct), such that the progeny are segregating into plants either comprising or not comprising the recombinant DNA construct (or suppression DNA construct): the progeny comprising the recombinant DNA construct (or suppression DNA construct) would be typically measured relative to the progeny not comprising the recombinant DNA construct (or suppression DNA construct). The progeny not comprising the recombinant DNA construct (or the suppression DNA construct) is the control or reference plant.

2. Introgression of a recombinant DNA construct (or suppression DNA construct) into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct (or suppression DNA construct): the second hybrid line would typically be measured relative to the first hybrid line (i.e., the first hybrid line is the control or reference plant).

4. A plant comprising a recombinant DNA construct (or suppression DNA construct): the plant may be assessed or measured relative to a control plant not comprising the recombinant DNA construct (or suppression DNA construct) but otherwise having a comparable genetic background to the plant (e.g., sharing at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity of nuclear genetic material compared to the plant comprising the recombinant DNA construct (or suppression DNA construct)). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Methods:

Methods include but are not limited to methods for increasing drought tolerance in a plant, methods for evaluating drought tolerance in a plant, methods for increasing paraquat tolerance, methods for altering an agronomic characteristic in a plant, methods for determining an alteration of an agronomic characteristic in a plant, methods for regulating plant flowering time, methods for observing and/or evaluating plant agricultural characteristics, methods for increasing low nitrogen tolerance, and methods for producing seed. The plant may be a monocotyledonous or dicotyledonous plant, for example, rice, maize or soybean plant. The plant may also be sunflower, canola, wheat, alfalfa, cotton, barley, millet, sugar cane or sorghum. The seed may be a maize or soybean seed, for example, a maize hybrid seed or maize inbred seed.

Methods include but are not limited to the following:

A method for transforming a cell comprising transforming a cell with any one or more of the isolated polynucleotides of the present disclosure, wherein, in particular embodiments, the cell is eukaryotic cell, e.g., a yeast, insect or plant cell; or prokaryotic cell, e.g., a bacterial cell.

A method for producing a transgenic plant comprising transforming a plant cell with any of the isolated polynucleotides or recombinant DNA constructs (including suppression DNA constructs) of the present disclosure and regenerating a transgenic plant from the transformed plant cell, wherein, the transgenic plant and the transgenic seed obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory element, and wherein the transformed host cell is grown under conditions that are suitable for expression of the recombinant DNA construct.

A method for altering the level of expression of a polypeptide of the disclosure in a host cell comprising: (a) transforming a host cell with a recombinant DNA construct of the present disclosure; and (b) growing the transformed host cell under conditions that are suitable for the expression of the recombinant DNA construct, wherein the expression of the recombinant DNA construct results in production of altered levels of the polypeptide of the disclosure in the transformed host cell.

A method of increasing drought tolerance in a plant, comprising increasing the expression of at least one polynucleotide encoding an ICDH1, MtN3L, DN-DTP6, ANKL1, MBD2, TP1, ACOAT1, DN-DTP7 polypeptide in plant, wherein the polynucleotide comprises: (a) a polynucleotide with nucleotide sequence of at least 85% sequence identity to SEQ ID NO: 2, 5, 8, 11, 14, 17, 20 or 23; (b) a polynucleotide with nucleotide sequence of at least 85% sequence identity to SEQ ID NO: 3, 6, 9, 12, 15, 18, 21 or 24; and (c) a polynucleotide encoding a polypeptide with amino acid sequence of at least 90% sequence identity to SEQ ID NO: 4, 7, 10, 13, 16, 19, 22 or 25.

A method of increasing drought tolerance and/or paraquat tolerance in a plant, comprising: (a) introducing into a regenerable plant cell a recombinant DNA construct comprising a polynucleotide operably linked to at least one regulatory element (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO: 4, 7, 10, 13, 16, 19, 22 or 25; (b) regenerating a transgenic plant from the regenerable plant cell after step (a), wherein the transgenic plant comprises in its genome the recombinant DNA construct and exhibits increased drought tolerance and/or paraquat tolerance when compared to a control plant; and further (c) obtaining a progeny plant derived from transgenic plant, wherein said progeny plant comprises in its genome the recombinant DNA construct and exhibits increased drought tolerance and/or paraquat tolerance when compared to a control plant.

A method of evaluating drought tolerance and/or paraquat tolerance in a plant comprising (a) obtaining a transgenic plant, which comprises in its genome a recombinant DNA construct comprising a polynucleotide operably linked to at least one regulatory element (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4, 7, 10, 13, 16, 19, 22 or 25; (b) obtaining a progeny plant derived from said transgenic plant, wherein the progeny plant comprises in its genome the recombinant DNA construct; and (c) evaluating the progeny plant for drought tolerance and/or paraquat tolerance compared to a control plant.

A method of determining an alteration of an agronomic characteristic in a plant comprising (a) obtaining a transgenic plant which comprises in its genome a recombinant DNA construct comprising a polynucleotide operably linked to at least one regulatory element (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when compared to SEQ ID NO: 4, 7, 10, 13, 16, 19, 22 or 25; (b) obtaining a progeny plant derived from said transgenic plant, wherein the progeny plant comprises in its genome the recombinant DNA construct; and (c) determining whether the progeny plant exhibits an alteration in at least one agronomic characteristic when compared, optionally under water limiting conditions to a control plant.

A method of regulating plant flowering time comprising: (a) introducing into a regenerable plant cell a recombinant DNA construct comprising a polynucleotide operably linked to at least one regulatory element (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, when compared to SEQ ID NO: 16; and (b) regenerating a transgenic plant from the regenerable plant cell after step (a), wherein the transgenic plant comprises in its genome the recombinant DNA construct and exhibits regulated flowering time when compared to a control plant not comprising the recombinant DNA construct. The method may further comprise (c) obtaining a progeny plant derived from the transgenic plant, wherein said progeny plant comprises in its genome the recombinant DNA construct and exhibits altered flowering time when compared to a control plant not comprising the recombinant DNA construct.

A method of increasing low nitrogen tolerance or NUE in a plant, comprising increasing the expression of at least one polynucleotide encoding a MtN3L or ANKL1 polypeptide in plant, wherein the polynucleotide comprises: (a) a polynucleotide with nucleotide sequence of at least 85% sequence identity to SEQ ID NO: 5 or 11; (b) a polynucleotide with nucleotide sequence of at least 85% sequence identity to SEQ ID NO: 6 or 12; and (c) a polynucleotide encoding a polypeptide with amino acid sequence of at least 90% sequence identity to SEQ ID NO: 7 or 13. Wherein the expression of the polynucleotide is increased by a step selected from the group consisting of: (a) increasing the expression of the polynucleotide encoding a MtN3L or ANKL1 polypeptide in plant by a recombinant DNA construct, wherein the recombinant DNA construct comprises the polynucleotide encoding the MtN3L or ANKL1 polypeptide operably linked to at least one heterologous regulatory element, wherein the polynucleotide encodes the polypeptide having an amino acid sequence of at least 90% sequence identity compared to SEQ ID NO: 7 or 13; and (b) increasing the expression of an endogenous polynucleotide encoding the polypeptide having an amino acid sequence of at least 90% sequence identity compared to SEQ ID NO: 7 or 13.

A method of producing seed comprising any of the preceding methods, and further comprising obtaining seeds from said progeny plant, wherein said seeds comprise in their genome said recombinant DNA construct (or suppression DNA construct).

In any of the preceding methods or any other embodiments of methods of the present disclosure, in said introducing step, the said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a medium comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the step of determining an alteration of an agronomic characteristic in a transgenic plant, if applicable, may comprise determining whether the transgenic plant exhibits an alteration of at least one agronomic characteristic when compared, under varying environmental conditions, to a control plant not comprising the recombinant DNA construct.

In any of the preceding methods or any other embodiments of methods of the present disclosure, the step of determining an alteration of an agronomic characteristic in a progeny plant, if applicable, may comprise determining whether the progeny plant exhibits an alteration of at least one agronomic characteristic when compared, under varying environmental conditions, to a control plant not comprising the recombinant DNA construct.

In any of the preceding methods or any other embodiments of methods of the present disclosure, the plant may exhibit the alteration of at least one agronomic characteristic when compared, under water limiting conditions to a control plant.

In any of the preceding methods or any other embodiments of methods of the present disclosure, alternatives exist for introducing into a regenerable plant cell a recombinant DNA construct comprising a polynucleotide operably linked to at least one regulatory element. For example, one may introduce into a regenerable plant cell a regulatory element (such as one or more enhancers, optionally as part of a transposable element), and then screen for an event in which the regulatory element is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and noncoding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

Stacking of Traits in Transgenic Plant

Transgenic plants may comprise a stack of one or more drought tolerance polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and cotransformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or over-expression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

EXAMPLES

The present disclosure is further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Furthermore, various modifications of the disclosure in addition to those shown and described herein will be apparent to those skilled in the art from the foregoing description. Such modifications are also intended to fall within the scope of the appended claims.

Example 1

Cloning and Vector Construction of Drought Tolerance Genes

Based on our preliminary screening of rice activation tagging population and the sequence information of gene IDs shown in Table 2, primers were designed for cloning rice drought tolerance genes OsICDH1, OsMtN3L, OsDN-DTP6, OsANKL1, OsMBD2, OsTP1, OsACOAT1 and OsDN-DTP7. The primers and the expected-lengths of the amplified genes are shown in Table 3.

For OsICDH1, OsACOAT1 and OsDN-DTP7, their cDNAs were cloned using pooled cDNA from leaf, stem and root tissues of Zhonghua 11 plant as the template. For OsMtN3L, OsDN-DTP6, OsANKL1, OsMBD2 and OsTP1, its gDNA were cloned, and amplified using genomic DNA of Zhonghua 11 as the template. The PCR reaction mixtures and PCR procedures are shown in Table 4 and Table 5.

TABLE 2

Rice gene names, Gene IDs (from TIGR) and Construct IDs

| Gene name | LOC ID | Construct ID |
|---|---|---|
| OsICDH1 | LOC_Os01g14580 | DP0854 |
| OsMtN3L | LOC_Os01g40960 | DP0902 |
| OsDN-DTP6 | LOC_Os09g15190 | DP0935 |
| OsANKL1 | LOC_Os09g15200 | DP0960 |
| OsMBD2 | LOC_Os06g48870 | DP0988 |
| OsTP1 | LOC_Os05g03810 | DP1082 |
| OsACOAT1 | LOC_Os05g03830 | DP1121 |
| OsDN-DTP7 | LOC_Os03g15720 | DP1176 |

TABLE 3

Primers for cloning rice drought tolerance genes

| Primer | Sequence | SEQ ID NO: | Gene name | Length of amplified fragment (bp) |
|---|---|---|---|---|
| gc-6703 | 5'-GACTCCGACGACCAGAAGCTACC-3' | 26 | OsICDH1 | 1349 |
| gc-6704 | 5'-CTAACATGTCCCCTGCCGTTG-3' | 27 | | |
| gc-6348 | 5'-CACTGACATGTGGCCTTCCTTCTTCC-3' | 28 | OsMtN3L | 622 |
| gc-6349 | 5'-CTAAGACAAAATTAGGTGCAGGATGGG-3' | 29 | | |

TABLE 3-continued

Primers for cloning rice drought tolerance genes

| Primer | Sequence | SEQ ID NO: | Gene name | Length of amplified fragment (bp) |
|---|---|---|---|---|
| gc-6728 | 5'-GCTGCAAAGGAGGAAGAGAAAGAGTGTTG-3' | 30 | OsDN-DTP6 | 1459 |
| gc-6729 | 5'-GAGATCGCAACAAACCCATACCCAAAC-3' | 31 | | |
| gc-6733 | 5'-CAAGTACCTGTAAATTGAAACCTGCAG-3' | 32 | OsANKL1 | 2829 |
| gc-6734 | 5'-CCACACTCTGAATTCCCCTCTTTC-3' | 33 | | |
| gc-7028 | 5'-CCCTGTTTAGAACTCCATCCTATAGATCG-3' | 34 | OsMBD2 | 4979 |
| gc-7029 | 5'-GGCAGACTGACAGAGACAAAGGCAC-3' | 35 | | |
| gc-6658 | 5'-GAAGTAGTACTAAAATGGATCTCGCACAC-3' | 36 | OsTP1 | 2044 |
| gc-6659 | 5'-GATGTTACAAAGATTAGGTGGTTCAGTC-3' | 37 | | |
| gc-6668 | 5'-CATGAACTCGCTCCAATCCTTCCTC-3' | 38 | OsACOAT1 | 1481 |
| gc-6669 | 5'-GTTCATTCTAACATCCATTGCTAAGGG-3' | 39 | | |
| gc-6393 | 5'-GCGAAAATCTTATCATTGTAGTTCTTTCC-3' | 40 | OsDN-DTP7 | 413 |
| gc-6394 | 5'-CACAATGACAGATGTACAGGTTAACC-3' | 41 | | |

TABLE 4

PCR reaction mixture for cloning drought tolerance genes

| Reaction mix | 50 μL |
|---|---|
| Template | 1 μL |
| TOYOBO KOD-FX (1.0 U/μL) | 1 μL |
| 2 × PCR buffer for KOD-FX | 25 μL |
| 2 mM dNTPs (0.4 mM each) | 10 μL |
| Primer-F/R (10 μM) | 2 μL each |
| ddH$_2$O | 9 μL |

TABLE 5

PCR cycle conditions

| 94° C. | 3 min | |
| 98° C. | 10 s | |
| 58° C. | 30 s | ×30 |
| 68° C. | (1 Kb/min) 1 min | |
| 68° C. | 5 min | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0158 (pCAMBIA1300-DsRed) (SEQ ID NO: 1).

The cloned nucleotide sequence in construct of DP0854 and coding sequence of OsICDH1 are provided as SEQ ID NO: 2 and 3, the encoded amino acid sequence of OsICDH1 is SEQ ID NO: 4; the cloned nucleotide sequence in construct of DP0902 and coding sequence of OsMtN3L are provided as SEQ ID NO: 5 and 6, the encoded amino acid sequence of OsMtN3L is SEQ ID NO: 7; the cloned nucleotide sequence in construct of DP0935 and coding sequence of OsDN-DTP6 are provided as SEQ ID NO: 8 and 9, the encoded amino acid sequence of OsDN-DTP6 is SEQ ID NO: 10; the cloned nucleotide sequence in construct of DP0960 and coding sequence of OsANKL1 are provided as SEQ ID NO: 11 and 12, the encoded amino acid sequence of OsANKL1 is SEQ ID NO: 13; the cloned nucleotide sequence in construct of DP0988 and coding sequence of OsMBD2 are provided as SEQ ID NO: 14 and 15, the encoded amino acid sequence of OsMBD2 is SEQ ID NO: 16; the cloned nucleotide sequence in construct of DP1082 and coding sequence of OsTP1 are provided as SEQ ID NO: 17 and 18, the encoded amino acid sequence of OsTP1 is SEQ ID NO: 19; the cloned nucleotide sequence in construct of DP1121 and coding sequence of OsACOAT1 are provided as SEQ ID NO: 20 and 21, the encoded amino acid sequence of OsACOAT1 is SEQ ID NO: 22; and the cloned nucleotide sequence in construct of DP1176 and coding sequence of OsDN-DTP7 are provided as SEQ ID NO: 23 and 24, the encoded amino acid sequence of OsDN-DTP7 is SEQ ID NO: 25.

Example 2

Transformation to Get Transgenic Rice Lines

In this research, all the over-expression vectors and empty vector (DP0158) were transformed into the Zhonghua 11 (*Oryza sativa* L.) by *Agrobacteria*-mediated method as described by Lin and Zhang ((2005) *Plant Cell Rep.* 23:540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with *Agrobacteria* with the vector. The transgenic seedlings (T$_0$) generated in transformation laboratory are transplanted in the field to get T$_1$ seeds. The T$_1$ and T$_2$ seeds are stored at cold room (4° C.). The over-expression vectors contain marker genes. T$_1$ and T$_2$ seeds which showed red color under green fluorescent light were transgenic seeds and were used in the following trait screening.

Example 3

Gene Expression Analysis

The gene expression levels in the transgenic rice plants were analyzed. A standard RT-PCR or a real-time RT-PCR procedure, such as the QuantiTect® Reverse Transcription Kit from Qiagen® and Real Time-PCR (SYBR®Premix Ex Taq™, TaKaRa), was used. EF-1α gene was used as an internal control to show that the amplification and loading of samples from the transgenic rice and the controls were similar. Gene expression was normalized based on the EF-1α mRNA levels.

The relative expression levels of OsICDH1 gene in leaves of different transgenic rice lines were determined by real-time PCR analyses. The base level of expression in ZH11-TC was set at 1.00, and the expression levels in other OsICDH1 lines ranged from about 6-376 fold-increases compared to ZH11-TC. ZH11-TC is tissue cultured ZH11 rice and DP0158 is empty vector transformed ZH11 rice plants. The primers for real-time RT-PCR for the OsICDH1 gene in the over-expression transgenic rice are listed below:

```
DP0854-F1:
                                       (SEQ ID NO: 42)
5'-CAAAAAGGAGGCGAAACTAG-3'

DP0854-R1:
                                       (SEQ ID NO: 43)
5'-CATGTACAAGAAGAGCTAGATCC-3'
```

The relative expression levels of OsMtN3L gene in leaves of different transgenic rice lines were determined by real-time PCR analyses and ranged from about 134-446 as compared to the base expression level in ZH11-TC (control; set at 1.00). OsMtN3L over-expressed in almost all the tested transgenic rice lines. The primers used for the real-time PCR are as below:

```
DP0902-F1:
                                       (SEQ ID NO: 44)
5'-TGAAGGCCAAATCGACCG-3'

DP0902-R1:
                                       (SEQ ID NO: 45)
5'-GAAGTCCATACCACAGGCAG-3'
```

The relative expression levels of OsDN-DTP6 gene in leaves of different transgenic rice lines were determined by real-time PCR analyses and ranged from about 50-508 as compared to the base expression level in DP0158 (control; set at 1.00). OsDN-DTP6 over-expressed in most the transgenic lines except DP0935.13.

```
DP0935-F1:
                                       (SEQ ID NO: 46)
5'-TTGGGACGCTTCGAGATTG-3'

DP0935-R1:
                                       (SEQ ID NO: 47)
5'-ATCTGGTCCGGAGTAAGATAATTTC-3'
```

The relative expression levels of OsANKL1 gene in leaves of different transgenic rice lines were determined by real-time PCR analyses and ranged from about 1.3-168 as compared to the base expression level in DP0158 (control; set at 1.00). The expression levels of OsANKL1 are slightly higher than that in DP0158 seedlings.

```
DP0960-F1:
                                       (SEQ ID NO: 48)
5'-GGTATCCCTAGCTATCGCAAAC-3'

DP0960-R1:
                                       (SEQ ID NO: 49)
5'-TTCCACGTGAACAGGAGAAC-3'
```

Figure 13:
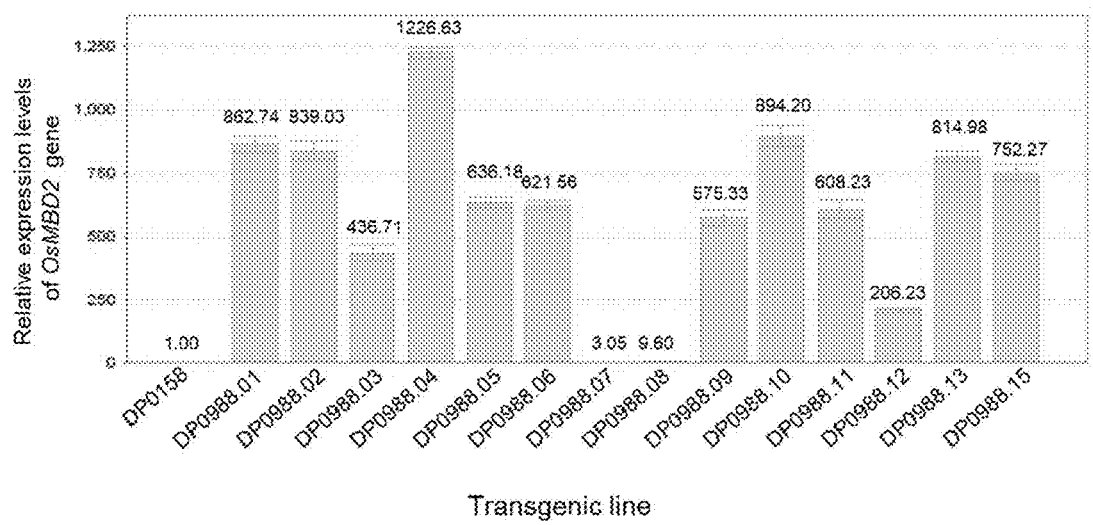
FIG. 13 shows the relative expression levels of OsMBD2 gene in leaves of different transgenic rice lines by real-time PCR analyses. The base expression level in DP0158 is set at 1.00, the numbers on the top of the columns are fold-changes compared to DP0158 rice.

The relative expression levels of OsMBD2 gene in leaves of different transgenic rice lines were determined by real-time PCR analyses and ranged from about 206-1226 as compared to the base expression level in DP0158 (control; set at 1.00) (FIG. 13.).

```
DP0988-F1:
                                       (SEQ ID NO: 50)
5'-CATACCCTGTAGACTTGCACC-3'

DP0988-R1:
                                       (SEQ ID NO: 51)
5'-CGCCCTCGTTTCATAGTTTTC-3'
```

The relative expression levels of OsTP1 gene in leaves of different transgenic rice lines were determined by real-time PCR analyses and ranged from about 1-4.8 as compared to the base expression level in DP1082.11 (control; set at 1.00). OsTP1 over-expressed in most the transgenic rice lines, while the expression of OsTP1 was low in ZH11-TC and DP0158 plants.

```
DP1082-F1:
                                       (SEQ ID NO: 52)
5'-TGCAGTTCCAGAGGTCTTTG-3'

DP1082-R1:
                                       (SEQ ID NO: 53)
5'-ATCACACGTCCATGGCTG-3'
```

The relative expression levels of OsACOAT1 gene in leaves of different transgenic rice lines were determined by real-time PCR analyses and ranged from about 6.26-33.47 as compared to the base expression level in ZH11-TC (control; set at 1.00).

```
DP1121-F1:
                                       (SEQ ID NO: 54)
5'-ACGCCCATGTGAAAGAGATC-3'

DP1121-R1:
                                       (SEQ ID NO: 55)
5'-CAAGCACGCATCAACCAAAG-3'
```

The relative expression levels of OsDN-DTP7 gene in leaves of different transgenic rice lines were determined by real-time PCR analyses and ranged from about 10-44 as compared to the base expression level in DP0158 (control; set at 1.00).

```
DP1176-F1:
                                       (SEQ ID NO: 56)
5'-GAAAGGGTATGGCTCTGGTAAG-3'

DP1176-R1:
                                       (SEQ ID NO: 57)
5'-GATGTCAGATAGTGTGCGAGG-3'
```

Example 4

Drought Assays of Transgenic Rice Plants in Greenhouse

The transgenic rice plants were screened in greenhouse drought assays. Two types of lamps were provided as light source, i.e. sodium lamp and metal halide lamp with the ratio of 1:1. Lamps provided the 16 h/8 h period of day/night, and were placed approximately 1.5 m above the seedbed. The light intensity 30 cm above the seedbed was measured as 10,000-20,000 lx in sunny day, while 6,000-10,000 lx in cloudy day, the relative humidity ranged from 30% to 90%, and the temperature ranged from 20 to 35° C.

Drought Screening Method:

T$_2$ transgenic seeds were sterilized by 800 ppm carbendazol for 8 h at 32° C. and washed 3~5 times with distilled water, then soaked in water for 16 h at 32° C., germinated for 18 h at 35~37 00 in an incubator. The germinated seeds were sowed in one tray filled with mixture of organic soil (FangJie soil from Beijing HuiYeShengDa Center), vermiculite (Beijing QingYuanShiJi Garden Center) and sand (Beijing Shuitun Construction Material Market) (V:V:V=3:3:2). The seedlings were grown under normal greenhouse condition and watered by modified IRRI solution. When the seedlings grew to 3-leaf stage, watering was stopped and the trays were kept in a dry place until the leaves became dry and curved (approximately 9~15 days depending on the seasons). The trays were transferred into water pool to recover the seedlings for 5-7 days, and then plants were scored for the recovery degree. The following scoring system was used: more than half green stem=1, more than two third green leaf=1, less than two third but more than one third green leaf=0.5, less than one third green leaf=0.2, no green leaf or less than half green stem=0. The recovery degree was the sum of the score of the green tissues, and the data were statistically analyzed using Mixed Model. The lines which showed significant better than controls (P<0.05) were considered as positive ones. Survival rate (percentage of survived plants over the total plant number) was also used as a parameter for drought screening.

Randomized block design was used for testing the transformed rice from construct level. Eight transgenic lines from the same construct were planted in one experimental unit to evaluate the transgene at construct level by Mixed Model considering construct, line and environment effects. If the survival rates or recovery degrees of the transgenic rice plants were significantly greater than control (P<0.05), the gene was considered having drought tolerant function.

GH Drought Assay Results:

1) GH Drought Tolerance (DRT) Validation Results of OsICDH1 (DP0854) Transgenic Rice In the first experiment, eight OsICDH1 transgenic lines were tested with one repeat. The three-leaf stage seedlings were placed at drought conditions for 20 days, and then were recovered in water for 6 days. The recovery degrees and the survival rates were measured. Table 6 shows that the recovery degree and the survival rate of the OsICDH1 transgenic rice plants were higher than that of ZH11-TC and DP0158 controls at the construct level. Five lines had higher survival rates than ZH11-TC and DP0158 controls at the line level. These results indicate that OsICDH1 transgenic rice may increase the drought tolerance at seedling stage.

TABLE 6

Enhanced drought tolerance of OsICDH1 transgenic rice plants under greenhouse conditions (1$^{st}$ experiment)

| Line ID | Number of survival plants | Number of total plants | Survival rate (%) | Average recovery degree | CK = ZH11-TC P value P ≤ 0.05 | CK = DP0158 P value P ≤ 0.05 |
|---|---|---|---|---|---|---|
| DP0854 (construct) | 63 | 80 | 78.78 | 1.41 | 0.3465 | 0.7895 |
| ZH11-TC | 14 | 20 | 70.00 | 1.24 | | |
| DP0158 | 15 | 20 | 75.00 | 1.36 | | |
| DP0854.06 | 9 | 10 | 90.00 | 1.41 | 0.3465 | 0.7895 |
| DP0854.07 | 8 | 10 | 80.00 | 1.41 | 0.3465 | 0.7895 |
| DP0854.08 | 9 | 10 | 90.00 | 1.41 | 0.3465 | 0.7895 |
| DP0854.09 | 8 | 10 | 80.00 | 1.41 | 0.3465 | 0.7895 |
| DP0854.10 | 7 | 10 | 70.00 | 1.41 | 0.3465 | 0.7895 |
| DP0854.11 | 8 | 10 | 80.00 | 1.41 | 0.3465 | 0.7895 |
| DP0854.12 | 7 | 10 | 70.00 | 1.41 | 0.3465 | 0.7895 |
| DP0854.13 | 7 | 10 | 70.00 | 1.41 | 0.3465 | 0.7895 |

In the second experiment, the same eight OsICDH1 transgenic rice lines were tested with one repeat. When grown to 3-leaf stage, the plants were drought stressed for 15 days and recovered in water for six days, and then the recovery degrees were scored. As shown in Table 7, OsICDH1 transgenic rice plants showed greater recovery degree and survival rate compared to ZH11-TC and DP0158 control plants at the construct level. Six transgenic rice lines showed greater survival rates than ZH11-TC and DP0158 controls (Table 7). These results also demonstrate that OsICDH1 gene may play a role in enhancing drought tolerance in plant at seedling stage.

TABLE 7

Enhanced drought tolerance of OsICDH1 transgenic rice plants under greenhouse conditions (2$^{nd}$ experiment)

| Line ID | Number of survival plants | Number of total plants | Survival rate (%) | Average recovery degree | CK = ZH11-TC P value P ≤ 0.05 | CK = DP0158 P value P ≤ 0.05 |
|---|---|---|---|---|---|---|
| DP0854 (construct) | 61 | 96 | 63.54 | 1.13 | 0.3142 | 0.5580 |
| ZH11-TC | 11 | 24 | 45.83 | 0.92 | | |
| DP0158 | 13 | 24 | 54.17 | 1.01 | | |
| DP0854.06 | 9 | 12 | 75.00 | 1.13 | 0.3142 | 0.5580 |
| DP0854.07 | 7 | 12 | 58.33 | 1.13 | 0.3142 | 0.5580 |

TABLE 7-continued

Enhanced drought tolerance of OsICDH1 transgenic rice plants under greenhouse conditions (2$^{nd}$ experiment)

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0854.08 | 10 | 12 | 83.33 | 1.13 | 0.3142 | | 0.5580 | |
| DP0854.09 | 8 | 12 | 66.67 | 1.13 | 0.3142 | | 0.5580 | |
| DP0854.10 | 8 | 12 | 66.67 | 1.13 | 0.3142 | | 0.5580 | |
| DP0854.11 | 8 | 12 | 66.67 | 1.13 | 0.3142 | | 0.5580 | |
| DP0854.12 | 5 | 12 | 41.67 | 1.13 | 0.3142 | | 0.5580 | |
| DP0854.13 | 6 | 12 | 50.00 | 1.13 | 0.3142 | | 0.5580 | |

2) GH DRT Validation Results of OsDN-DTP6 (DP0935) Transgenic Rice

Eight OsDN-DTP6 transgenic lines were tested with four repeats. When grown to 3-leaf stage, the plants were placed to drought conditions for 20 days, recovered in water for five to eight days. The recovery degree and the survival rate of OsDN-DTP6 transgenic rice plants were similar to that of ZH11-TC and DP0158 at the construct level. Analysis at the line level demonstrate that four OsDN-DTP6 transgenic rice lines exhibited higher survival rates than both ZH11-TC and DP0158 control plants, three lines showed significantly greater recovery degrees than ZH11-TC and two lines showed significantly greater recovery degrees than DP0158 control plants (Table 8). The results indicate that OsDN-DTP6 transgenic rice showed enhanced drought tolerance at seedling stage.

3) GH DRT Validation Results of OsANKL1 (DP0960) Transgenic Rice

Eight OsANKL1 transgenic rice plants were tested with three repeats. The plants grown to 3-leaf stage under normal condition, then these plants were placed to drought conditions and be without water for about 22 days, recovered in water for five days, and then the plants were drought stressed for another 22 days. After recovered in water for about six days, the recovery degrees were scored. As shown in Table 9, OsANKL1 transgenic rice exhibited similar survival rate and recovery degree to that of ZH11-TC and DP0158 controls at the construct and line levels.

TABLE 8

Enhanced drought tolerance of OsDN-DTP6 transgenic rice plants under greenhouse conditions

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0935 (construct) | 250 | 384 | 65.10 | 1.17 | 0.8423 | | 0.9040 | |
| ZH11-TC | 60 | 96 | 62.50 | 1.14 | | | | |
| DP0158 | 62 | 96 | 64.58 | 1.19 | | | | |
| DP0935.03 | 24 | 48 | 50.00 | 0.84 | 0.0528 | | 0.0224 | |
| DP0935.05 | 30 | 48 | 62.50 | 1.13 | 0.9512 | | 0.6837 | |
| DP0935.06 | 42 | 48 | 87.50 | 1.57 | 0.0048 | Y | 0.0134 | Y |
| DP0935.07 | 42 | 48 | 87.50 | 1.58 | 0.0041 | Y | 0.0117 | Y |
| DP0935.13 | 20 | 48 | 41.67 | 0.75 | 0.0099 | | 0.0035 | |
| DP0935.14 | 39 | 48 | 81.25 | 1.48 | 0.0260 | Y | 0.0602 | |
| DP0935.17 | 21 | 48 | 43.75 | 0.80 | 0.0276 | | 0.0108 | |
| DP0935.18 | 32 | 48 | 66.67 | 1.23 | 0.5538 | | 0.8058 | |

TABLE 9

Enhanced drought tolerance of OsANKL1 transgenic rice plants under greenhouse conditions

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0960 (construct) | 249 | 288 | 86.46 | 1.54 | 0.3063 | | 0.4526 | |
| ZH11-TC | 64 | 72 | 88.89 | 1.65 | | | | |

TABLE 9-continued

Enhanced drought tolerance of OsANKL1 transgenic rice plants under greenhouse conditions

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0158 | 59 | 72 | 81.94 | 1.46 | | | | |
| DP0960.01 | 30 | 36 | 83.33 | 1.54 | 0.3953 | | 0.5160 | |
| DP0960.03 | 31 | 36 | 86.11 | 1.54 | 0.3583 | | 0.5612 | |
| DP0960.07 | 33 | 36 | 91.67 | 1.58 | 0.5911 | | 0.3358 | |
| DP0960.09 | 30 | 36 | 83.33 | 1.48 | 0.1838 | | 0.8646 | |
| DP0960.10 | 35 | 36 | 97.22 | 1.68 | 0.8522 | | 0.0918 | |
| DP0960.12 | 32 | 36 | 88.89 | 1.59 | 0.6392 | | 0.3026 | |
| DP0960.13 | 30 | 36 | 83.33 | 1.49 | 0.1970 | | 0.8340 | |
| DP0960.15 | 28 | 36 | 77.78 | 1.44 | 0.0872 | | 0.8330 | |

4) GH DRT Validation Results of OsMBD2 (DP0988) Transgenic Rice

Eight OsMBD2 transgenic lines were tested. When grown to 3-leaf stage, the plants were drought stressed for 22 days, and recovered in water for six days. 50 of the 96 OsMBD2 transgenic rice survived, while 5 of the 24 ZH11-TC and 2 of the 24 DP0158 seedlings survived. OsMBD2 transgenic rice exhibited higher survival rate and exhibited significantly higher average recovery degree than both ZH11-TC and DP0158 seedlings at the construct level (Table 10). Analysis at line level showed that all the eight lines exhibited higher survival rates and average recovery degrees than both controls. These results indicated that OsMBD2 transgenic rice showed enhanced drought tolerance at seedling stage when compared to ZH11-TC and DP0158 controls, and OsMBD2 gene plays a role in improving drought tolerance of transgenic plants.

5) GH DRT Validation Results of OsTP1 (DP1082) Transgenic Rice

Eight OsTP1 transgenic rice lines were tested with three repeats. When the plants grown to 3-leaf stage, the plants were placed to dry conditions and withdraw water for about 24 days, and then were recovered in water for five days. One repeat was drought stressed again for 19 days. After recovered in water for five days, the recovery degrees were scored. As shown in Table 11, 164 of the 288 OsTP1 transgenic rice plants survived, while 35 of the 72 ZH11-TC seedlings and 27 of the 72 DP0158 seedlings survived. The OsTP1 transgenic rice exhibited higher survival rate and significantly higher recovery degree than DP0158 and of ZH11-TC controls at the construct level. Analysis at line level showed that all the eight OsTP1 transgenic lines exhibited higher survival rates and significantly recovery degrees than both ZH11-TC and DP0158 controls (Table 11). These results demonstrate that OsTP1 gene plays a role in enhancing drought tolerance in plant.

TABLE 10

Enhanced drought tolerance of OsMBD2 transgenic rice plants under greenhouse conditions

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP0988 (construct) | 50 | 96 | 52.08 | 0.85 | 0.0121 | Y | 0.0006 | Y |
| ZH11-TC | 5 | 24 | 20.83 | 0.32 | | | | |
| DP0158 | 2 | 24 | 8.33 | 0.13 | | | | |
| DP0988.01 | 6 | 12 | 50.00 | 0.89 | 0.0231 | Y | 0.0023 | Y |
| DP0988.02 | 8 | 12 | 66.67 | 0.98 | 0.0087 | Y | 0.0007 | Y |
| DP0988.03 | 8 | 12 | 66.67 | 0.84 | 0.0390 | Y | 0.0044 | Y |
| DP0988.04 | 6 | 12 | 50.00 | 0.91 | 0.0196 | Y | 0.0018 | Y |
| DP0988.05 | 10 | 12 | 83.33 | 1.13 | 0.0013 | Y | 0.0001 | Y |
| DP0988.06 | 4 | 12 | 33.33 | 0.71 | 0.1203 | | 0.0195 | Y |
| DP0988.07 | 5 | 12 | 41.67 | 0.74 | 0.0928 | | 0.0138 | Y |
| DP0988.12 | 3 | 12 | 25.00 | 0.61 | 0.2482 | | 0.0528 | |

TABLE 11

Enhanced drought tolerance of OsTP1 transgenic rice plants under greenhouse conditions (1$^{st}$ experiment)

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP1082 (construct) | 164 | 288 | 56.94 | 0.86 | 0.0385 | Y | 0.0043 | Y |
| ZH11-TC | 35 | 72 | 48.61 | 0.63 | | | | |
| DP0158 | 27 | 72 | 37.50 | 0.54 | | | | |
| DP1082.01 | 20 | 36 | 55.56 | 0.86 | 0.0385 | Y | 0.0043 | Y |
| DP1082.04 | 13 | 36 | 36.11 | 0.86 | 0.0385 | Y | 0.0043 | Y |
| DP1082.08 | 21 | 36 | 58.33 | 0.86 | 0.0385 | Y | 0.0043 | Y |
| DP1082.09 | 20 | 36 | 55.56 | 0.86 | 0.0385 | Y | 0.0043 | Y |
| DP1082.10 | 22 | 36 | 61.11 | 0.86 | 0.0385 | Y | 0.0043 | Y |
| DP1082.11 | 22 | 36 | 61.11 | 0.86 | 0.0385 | Y | 0.0043 | Y |
| DP1082.12 | 25 | 36 | 69.44 | 0.86 | 0.0385 | Y | 0.0043 | Y |
| DP1082.13 | 21 | 36 | 58.33 | 0.86 | 0.0385 | Y | 0.0043 | Y |

The same eight OsTP1 transgenic lines were tested again with three repeats. When grown to 3-leaf stage, the plants were drought stressed for about 18 days, and recovered in water for five days. 242 of the 288 OsTP1 transgenic rice seedlings survived, while 51 of the 72 ZH11-TC and 51 of the 72 DP0158 seedlings survived. OsTP1 transgenic rice exhibited higher survival rate and exhibited significantly higher average recovery degree than both ZH11-TC and DP0158 seedlings at the construct level (Table 12). Analysis at line level showed that eight lines exhibited higher survival rates and average recovery degrees than both controls. These results further demonstrate that OsTP1 transgenic rice showed enhanced drought tolerance at seedling stage, and OsTP1 plays a role in improving drought tolerance of transgenic plants.

6) GH DRT Validation Results of OsACOAT1 (DP1121) Transgenic Rice

Eight OsACOAT1 transgenic lines were tested with four repeats. When the plants grown to 3-leaf stage, they were first drought stressed for about 26 days, recovered in water for about five days, and then the plants were drought stressed for 22 days again. After recover in water for about five days, the recover degrees were scored. As shown in Table 13, the OsACOAT1 transgenic rice plants exhibited similar survival rate and recovery degree at the construct level and at the line level, when compared to ZH11-TC and DP0158 controls.

TABLE 12

Enhanced drought tolerance of OsTP1 transgenic rice plants under greenhouse conditions (2$^{nd}$ experiment)

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP1082 (construct) | 242 | 288 | 84.03 | 1.32 | 0.0340 | Y | 0.0094 | Y |
| ZH11-TC | 51 | 72 | 70.83 | 1.09 | | | | |
| DP0158 | 51 | 72 | 70.83 | 1.04 | | | | |
| DP1082.01 | 31 | 36 | 86.11 | 1.41 | 0.0123 | Y | 0.0037 | Y |
| DP1082.04 | 31 | 36 | 86.11 | 1.32 | 0.0733 | | 0.0283 | Y |
| DP1082.08 | 27 | 36 | 75.00 | 1.23 | 0.2913 | | 0.1451 | |
| DP1082.09 | 30 | 36 | 83.33 | 1.24 | 0.2614 | | 0.1273 | |
| DP1082.10 | 30 | 36 | 83.33 | 1.25 | 0.2040 | | 0.0945 | |
| DP1082.11 | 33 | 36 | 91.67 | 1.49 | 0.0016 | Y | 0.0004 | Y |
| DP1082.12 | 30 | 36 | 83.33 | 1.29 | 0.1231 | | 0.0519 | |
| DP1082.13 | 30 | 36 | 83.33 | 1.32 | 0.0733 | | 0.0283 | Y |

TABLE 13

Enhanced drought tolerance of OsACOAT1 transgenic rice plants under greenhouse conditions

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP1121 (construct) | 316 | 384 | 82.29 | 1.50 | 0.2669 | | 0.6774 | |
| ZH11-TC | 75 | 96 | 78.13 | 1.40 | | | | |
| DP0158 | 78 | 96 | 81.25 | 1.46 | | | | |
| DP1121.01 | 40 | 48 | 83.33 | 1.50 | 0.3214 | | 0.7149 | |
| DP1121.02 | 42 | 48 | 87.50 | 1.51 | 0.2622 | | 0.6206 | |
| DP1121.03 | 40 | 48 | 83.33 | 1.50 | 0.2995 | | 0.6809 | |
| DP1121.04 | 35 | 48 | 72.92 | 1.46 | 0.5220 | | 0.9888 | |
| DP1121.05 | 43 | 48 | 89.58 | 1.53 | 0.1890 | | 0.4919 | |
| DP1121.09 | 44 | 48 | 91.67 | 1.54 | 0.1821 | | 0.4788 | |
| DP1121.10 | 34 | 48 | 70.83 | 1.46 | 0.5166 | | 0.9822 | |
| DP1121.11 | 38 | 48 | 79.17 | 1.49 | 0.3552 | | 0.7654 | |

7) GH DRT Validation Results of OsDN-DTP7 (DP1176) Transgenic Rice

Eight OsDN-DTP7 transgenic lines were tested with four repeats. The plants grew to 3-leaf stage under normal conditions, then the plants were placed to dry conditions and withdrew water for 20~22 days. After recovered in water for about six days, 262 of the 384 OsDN-DTP7 transgenic rice plants survived. As shown in Table 14, OsDN-DTP7 transgenic rice plants exhibited greater survival rate and higher recovery degree than DP0158 control plants. Four OsDN-DTP7 transgenic lines showed significantly recovery degrees than DP0158 control, and three lines showed higher recover degree than ZH11-TC control. These results demonstrate that OsDN-DTP7 transgenic rice plants may improve the drought tolerance at the seedling stage.

TABLE 14

Drought sensitive assay of OsDN-DTP7 transgenic rice plants under greenhouse conditions

| Line ID | Number of survival plants | Number of total plants | Survival rate (%) | Average recovery degree | CK = ZH11-TC P value | P ≤ 0.05 | CK = DP0158 P value | P ≤ 0.05 |
|---|---|---|---|---|---|---|---|---|
| DP1176 (construct) | 262 | 384 | 68.23 | 1.29 | 0.8740 | | 0.0139 | Y |
| ZH11-TC | 67 | 96 | 69.79 | 1.27 | | | | |
| DP0158 | 53 | 96 | 55.21 | 0.99 | | | | |
| DP1176.02 | 32 | 48 | 66.67 | 1.29 | 0.8756 | | 0.0358 | Y |
| DP1176.03 | 30 | 48 | 62.50 | 1.20 | 0.6186 | | 0.1486 | |
| DP1176.04 | 34 | 48 | 70.83 | 1.33 | 0.6454 | | 0.0163 | Y |
| DP1176.05 | 39 | 48 | 81.25 | 1.38 | 0.4097 | | 0.0057 | Y |
| DP1176.06 | 39 | 48 | 81.25 | 1.41 | 0.3013 | | 0.0029 | Y |
| DP1176.07 | 31 | 48 | 64.58 | 1.26 | 0.9688 | | 0.0570 | |
| DP1176.08 | 28 | 48 | 58.33 | 1.25 | 0.9098 | | 0.0674 | |
| DP1176.12 | 29 | 48 | 60.42 | 1.16 | 0.4507 | | 0.2347 | |

Example 5

Grain Yield of Mature Transgenic Rice Plants Under Well-Watered Conditions

The over-expression transgenic rice plants and ZH11-TC and DP0158 rice plants were planted in the paddy field to measure the grain yield under the well-watered conditions. Five transgenic lines from each gene construct were choose. The $T_2$ seeds were first sterilized as described in Example 4. The germinated seeds were planted in a seedbed field. At 3-leaf stage, the seedlings were transplanted into the testing field with 4 replicates and 40 plants per replicate for each transgenic line, and the 4 replicates were planted in the same block. ZH11-TC and DP0158 seedlings were nearby the transgenic lines in the same block, and were used as controls in the statistical analysis.

The rice plants were managed by normal practice using pesticides and fertilizers. Plant phenotypes were observed and recorded during the experiments. The phenotypes include heading date, leaf rolling degree, drought sensitivity and drought tolerance. At the end of the growing season, representative plants of each transgenic line were harvested from the middle of the row per line, and grain yield per plant was measured. The grain yield data were statistically analyzed using mixed linear model.

1) OsICDH1 (DP0854) Transgenic Rice Plants Planted Under Well-Watered Conditions Five OsICDH1 transgenic rice lines were used. There was no visible different phenotype between the transgenic rice plants and the control plants. As shown in Table 15, the grain yield per plant of OsICDH1 transgenic rice was significantly greater than that of ZH11-TC and DP 0158 controls at the construct level, and all the transgenic rice lines showed greater grain yield per plant than controls at the line level. These results show that over-expression of OsICDH1 gene may improve the grain yield per plant under well-watered conditions.

TABLE 15

Grain yield analysis of OsICDH1 transgenic rice plants under well-watered conditions

| Line IDs | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0854 (Construct) | 718 | 568 | 10.20 | 3.05 | 0.015 | Y | 4.50 | 0.000 | Y |
| ZH11-TC | 134 | 106 | 7.15 | | | | | | |
| DP0158 | 149 | 111 | 5.70 | | | | | | |
| DP0854.01 | 139 | 112 | 7.37 | 0.22 | 0.843 | | 1.67 | 0.127 | |
| DP0854.03 | 136 | 103 | 11.33 | 4.18 | 0.000 | Y | 5.63 | 0.000 | Y |
| DP0854.07 | 148 | 119 | 13.22 | 6.07 | 0.000 | Y | 7.52 | 0.000 | Y |
| DP0854.08 | 146 | 117 | 10.52 | 3.36 | 0.000 | Y | 4.82 | 0.000 | Y |
| DP0854.11 | 149 | 117 | 8.58 | 1.42 | 0.137 | | 2.87 | 0.004 | Y |

2) OsANKL1 (DP0960) Transgenic Rice Plants Planted Under Well-Watered Conditions Five OsANKL1 transgenic rice lines were used. There was no visible different phenotype between the transgenic rice plants and the control plants. As shown in Table 16, the grain yield per plant of OsANKL1 transgenic rice was significantly greater than that of ZH11-TC and DP 0158 controls at the construct level, and all the transgenic rice lines showed greater grain yield per plant than controls at the line level. These results show that over-expression of OsANKL1 gene may improve the grain yield per plant under well-watered conditions.

TABLE 16

Grain yield analysis of OsANKL1 transgenic rice plants under well-watered conditions

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0960 | 652 | 517 | 10.62 | 4.62 | 0.000 | Y | 4.16 | 0.001 | Y |
| ZH11-TC | 146 | 115 | 6.00 | | | | | | |
| DP0158 | 150 | 118 | 6.46 | | | | | | |
| DP0960.01 | 135 | 106 | 12.49 | 6.49 | 0.000 | Y | 6.03 | 0.000 | Y |
| DP0960.02 | 111 | 86 | 10.84 | 4.84 | 0.000 | Y | 4.38 | 0.000 | Y |
| DP0960.07 | 130 | 111 | 12.14 | 6.14 | 0.000 | Y | 5.68 | 0.000 | Y |
| DP0960.09 | 146 | 106 | 10.93 | 4.94 | 0.000 | Y | 4.48 | 0.000 | Y |
| DP0960.13 | 130 | 108 | 6.71 | 0.71 | 0.472 | | 0.25 | 0.783 | |

3) OsMBD2 (DP0988) Transgenic Rice Plants Planted Under Well-Watered Conditions

Five OsMBD2 transgenic rice lines were used. There was no visible different phenotype between the transgenic rice plants and the control plants. As shown in Table 17, the grain yield per plant of OsMBD2 transgenic rice was significantly greater than that of ZH11-TC and DP 0158 controls at the construct level, and all the transgenic rice lines showed significantly greater grain yield per plant than controls at the line level. These results show that over-expression of OsMBD2 gene may improve the grain yield per plant under well-watered conditions.

TABLE 17

Grain yield analysis of OsMBD2 transgenic rice plants under well-watered conditions

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0988 (Construct) | 734 | 562 | 11.91 | 5.47 | 0.000 | Y | 6.87 | 0.000 | Y |
| ZH11-TC | 141 | 110 | 6.43 | | | | | | |
| DP0158 | 150 | 112 | 5.04 | | | | | | |
| DP0988.02 | 140 | 107 | 11.83 | 5.40 | 0.000 | Y | 6.80 | 0.000 | Y |

TABLE 17-continued

Grain yield analysis of OsMBD2 transgenic rice plants under well-watered conditions

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0988.07 | 146 | 109 | 11.63 | 5.20 | 0.000 | Y | 6.59 | 0.000 | Y |
| DP0988.09 | 150 | 117 | 13.60 | 7.16 | 0.000 | Y | 8.56 | 0.000 | Y |
| DP0988.11 | 148 | 114 | 12.16 | 5.73 | 0.000 | Y | 7.13 | 0.000 | Y |
| DP0988.12 | 150 | 115 | 10.31 | 3.88 | 0.000 | Y | 5.27 | 0.000 | Y |

4) OsACOAT1 (DP1121) Transgenic Rice Plants Planted Under Well-Watered Conditions Five OsACOAT1 transgenic rice lines were used. There was no visible different phenotype between the transgenic rice plants and the control plants. As shown in Table 18, the grain yield per plant of OsACOAT1 transgenic rice was significantly greater than that of ZH11-TC and DP 0158 controls at the construct level, and all the transgenic rice lines showed significantly greater grain yield per plant than controls at the line level. These results show that over-expression of OsACOAT1 gene may improve the grain yield per plant under well-watered conditions.

TABLE 18 grain yield analysis of OsACOAT1 transgenic rice plants under well-watered conditions

| Line ID | Number of survival plants | Number of harvested plants | Yield per plant (g) | CK = DP0158 | | | CK = ZH11-TC | | |
|---|---|---|---|---|---|---|---|---|---|
| | | | | Diff | P value | P ≤ 0.1 | Diff | P value | P ≤ 0.1 |
| DP1121 (Construct) | 699 | 545 | 11.98 | 5.43 | 0.000 | Y | 6.05 | 0.000 | Y |
| ZH11-TC | 105 | 79 | 6.55 | | | | | | |
| DP0158 | 122 | 92 | 5.93 | | | | | | |
| DP1121.01 | 143 | 109 | 13.44 | 6.89 | 0.000 | Y | 7.50 | 0.000 | Y |
| DP1121.02 | 150 | 115 | 10.26 | 3.71 | 0.000 | Y | 4.32 | 0.000 | Y |
| DP1121.04 | 133 | 103 | 11.79 | 5.24 | 0.000 | Y | 5.85 | 0.000 | Y |
| DP1121.06 | 124 | 99 | 11.91 | 5.36 | 0.000 | Y | 5.98 | 0.000 | Y |
| DP1121.09 | 149 | 119 | 12.52 | 5.97 | 0.000 | Y | 6.58 | 0.000 | Y |

5) OsDN-DTP7 (DP1176) Transgenic Rice Plants Planted Under Well-Watered Conditions Five OsDN-DTP7 transgenic rice lines were used. There was no visible different phenotype between the transgenic rice plants and the control plants. As shown in Table 19, the grain yield per plant of OsDN-DTP7 transgenic rice was significantly greater than that of ZH11-TC and DP 0158 controls at the construct level, and all the transgenic rice lines showed greater grain yield per plant than controls at the line level. These results show that over-expression of OsDN-DTP7 gene may improve the grain yield per plant under well-watered conditions.

TABLE 19 grain yield analysis of OsDN-DTP7 transgenic rice plants under well-watered conditions

| Line ID | Number of survival plants | Number of harvested plants | Yield per plant (g) | CK = DP0158 | | | CK = ZH11-TC | | |
|---|---|---|---|---|---|---|---|---|---|
| | | | | Diff | P value | P ≤ 0.1 | Diff | P value | P ≤ 0.1 |
| DP1176 | 715 | 549 | 10.75 | 4.74 | 0.000 | Y | 4.98 | 0.000 | Y |
| ZH11-TC | 150 | 118 | 6.01 | | | | | | |
| DP0158 | 150 | 119 | 5.77 | | | | | | |
| DP1176.02 | 125 | 93 | 10.38 | 4.37 | 0.000 | Y | 4.61 | 0.000 | Y |
| DP1176.05 | 149 | 115 | 11.81 | 5.80 | 0.000 | Y | 6.04 | 0.000 | Y |
| DP1176.06 | 142 | 105 | 11.41 | 5.41 | 0.000 | Y | 5.65 | 0.000 | Y |
| DP1176.08 | 149 | 120 | 12.59 | 6.58 | 0.000 | Y | 6.82 | 0.000 | Y |
| DP1176.12 | 150 | 116 | 7.56 | 1.55 | 0.119 | | 1.79 | 0.047 | Y |

Example 6

Field Drought Assays of Mature Transgenic Rice Plants

Flowering stage drought stress is an important problem in agriculture practice. The transgenic rice plants were further tested under field drought conditions. For the Field drought assays of mature rice plants, 12 transgenic lines from each gene construct were tested. The $T_2$ seeds were first sterilized as described in Example 4. The germinated seeds were planted in a seedbed field. At 3-leaf stage, the seedlings were transplanted into the testing field with 4 replicates and 10 plants per replicate for each transgenic line, and the 4 replicates were planted in the same block. ZH11-TC and DP0158 seedlings were nearby the transgenic lines in the same block, and were used as controls in the statistical analysis.

The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain yield per plant was measured. The grain yield data were statistically analyzed using mixed linear model. Positive transgenic lines were selected based on the analysis (P<0.1).

Field Drought Assay Results:

1) Field DRT Validation Results of OsICDH1 (DP0854) Transgenic Rice

Twelve OsICDH1 transgenic lines were tested in Hainan Province in the first experiment. Watering was stopped from initiation stage II of the main stem panicle to seed maturity to produce heavier drought stress. The soil volumetric water content decreased from 38% to 7% during heading and maturation stage (FIG. 1). 25 days after stopping watering, the main stem panicles headed out, the tiller panicles were at panicle initiation VII-VIII stage, and some rice plants exhibited phenotypes such as leaf rolling. The transgenic rice plants DP0854.01, DP0854.02, DP0854.03, DP0854.04 and DP0854.07 exhibited drought tolerance phenotypes. At the end of the planting season, the transgenic rice plants DP0854.03, DP0854.04 and DP0854.07 exhibited good seed setting rate. The grain yield per plant is shown in Table 20, the OsICDH1 transgenic rice plants showed significantly greater grain yield per plant than both ZH11-TC and DP0158 plants at the construct level. Six OsICDH1 transgenic rice lines showed significantly greater grain yield per plant than ZH11-TC plants, and seven transgenic lines showed significantly greater grain yield per plant than DP0158 plants at the line level. These results indicate that OsICDH1 transgenic rice plant had greater grain yield per plant than controls after drought stress.

TABLE 20

Grain yield analysis of OsICDH1 transgenic rice plants under field drought conditions (1$^{st}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0854 (construct) | 475 | 288 | 4.82 | 1.32 | 0.024 | Y | 1.42 | 0.015 | Y |
| ZH11-TC | 40 | 24 | 3.50 | | | | | | |
| DP0158 | 40 | 24 | 3.40 | | | | | | |
| DP0854.01 | 40 | 24 | 4.80 | 1.30 | 0.054 | Y | 1.40 | 0.038 | Y |
| DP0854.02 | 39 | 24 | 4.21 | 0.71 | 0.288 | | 0.81 | 0.226 | |
| DP0854.03 | 40 | 24 | 5.51 | 2.01 | 0.003 | Y | 2.11 | 0.002 | Y |
| DP0854.04 | 40 | 24 | 4.50 | 1.00 | 0.136 | | 1.10 | 0.101 | |
| DP0854.06 | 39 | 24 | 4.41 | 0.91 | 0.174 | | 1.01 | 0.131 | |
| DP0854.07 | 38 | 24 | 6.36 | 2.85 | 0.000 | Y | 2.96 | 0.000 | Y |
| DP0854.08 | 39 | 24 | 5.29 | 1.79 | 0.008 | Y | 1.89 | 0.005 | Y |
| DP0854.09 | 40 | 24 | 4.15 | 0.65 | 0.332 | | 0.75 | 0.265 | |
| DP0854.10 | 40 | 24 | 4.95 | 1.45 | 0.031 | Y | 1.55 | 0.021 | Y |
| DP0854.11 | 40 | 24 | 5.03 | 1.53 | 0.024 | Y | 1.63 | 0.015 | Y |
| DP0854.12 | 40 | 24 | 4.09 | 0.59 | 0.379 | | 0.69 | 0.304 | |
| DP0854.13 | 40 | 24 | 4.51 | 1.01 | 0.132 | | 1.11 | 0.100 | Y |

Figure 2:
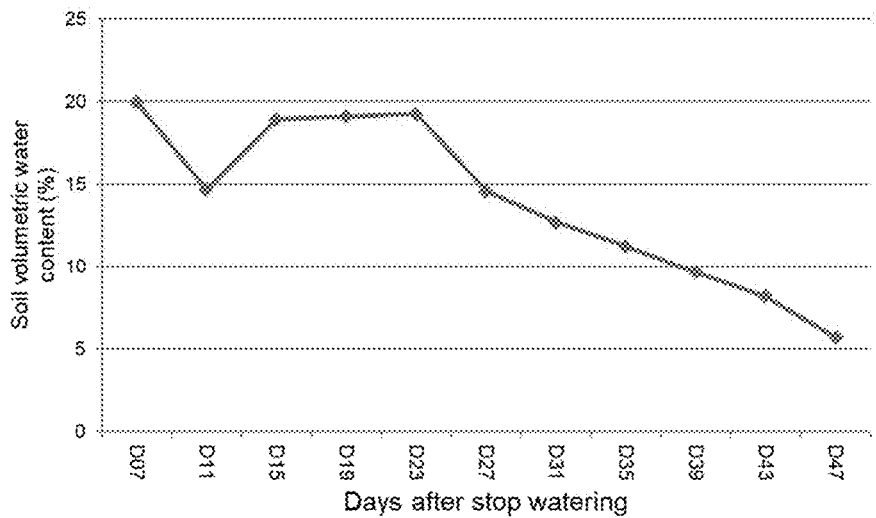
FIG. 2 shows changes of soil volumetric moisture content at different developmental stage in Hainan field in the second field experiment for drought testing OsICDH1 transgenic rice. The main stem panicle of OsICDH1 transgenic rice plants reached panicle initiation stage IV-VI stopping watering.

The second experiment was performed in Hainan province; the same twelve OsICDH1 transgenic lines were tested. When the main stem panicles reached panicle initiation stage IV-V and the tiller panicles reached panicle initiation stage II-III, watering was stopped. The soil volumetric water content decreased from 20% to 5% during panicle heading (FIG. 2). 52 days later, the main stem panicles reached milk mature stage, and the rice plants showed leaf rolling phenotype. As shown in Table 21, OsICDH1 transgenic rice exhibited greater grain yield per plant than ZH11-TC control and significantly greater grain yield per plant than DP0158 control at the construct level. Eight lines had significantly greater grain yields per plant than DP0158 control, and five lines had greater grain yield per plant than ZH11-TC control. These results further demonstrate that OsICDH1 rice plant is tolerance to drought stress, and over-expression of OsICDH1 increases the grain yield per plant after drought stress at flowering and heading stage.

TABLE 21

Grain yield analysis of OsICDH1 transgenic rice plants under field drought conditions (2$^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0854 (Construct) | 473 | 285 | 4.11 | 0.79 | 0.244 | | 1.37 | 0.040 | Y |
| ZH11-TC | 40 | 24 | 3.32 | | | | | | |
| DP0158 | 40 | 24 | 2.74 | | | | | | |
| DP0854.01 | 37 | 24 | 3.09 | −0.23 | 0.781 | | 0.35 | 0.658 | |
| DP0854.02 | 38 | 23 | 2.51 | −0.81 | 0.291 | | −0.23 | 0.757 | |
| DP0854.03 | 40 | 24 | 5.15 | 1.83 | 0.015 | Y | 2.41 | 0.001 | Y |
| DP0854.04 | 40 | 24 | 4.22 | 0.90 | 0.233 | | 1.47 | 0.049 | Y |
| DP0854.06 | 40 | 24 | 4.55 | 1.23 | 0.113 | | 1.80 | 0.018 | Y |
| DP0854.07 | 39 | 24 | 5.47 | 2.15 | 0.005 | Y | 2.73 | 0.000 | Y |
| DP0854.08 | 40 | 24 | 4.93 | 1.61 | 0.037 | Y | 2.19 | 0.003 | Y |
| DP0854.09 | 39 | 24 | 2.70 | −0.62 | 0.411 | | −0.04 | 0.955 | |
| DP0854.10 | 40 | 24 | 4.59 | 1.27 | 0.090 | Y | 1.84 | 0.012 | Y |
| DP0854.11 | 40 | 24 | 4.25 | 0.93 | 0.220 | | 1.51 | 0.046 | Y |
| DP0854.12 | 40 | 24 | 5.32 | 2.00 | 0.007 | Y | 2.58 | 0.000 | Y |
| DP0854.13 | 40 | 22 | 2.56 | −0.76 | 0.299 | | −0.18 | 0.808 | |

2) Field DRT Validation Results of OsMtN3L (DP0902) Transgenic Rice

Figure 3:
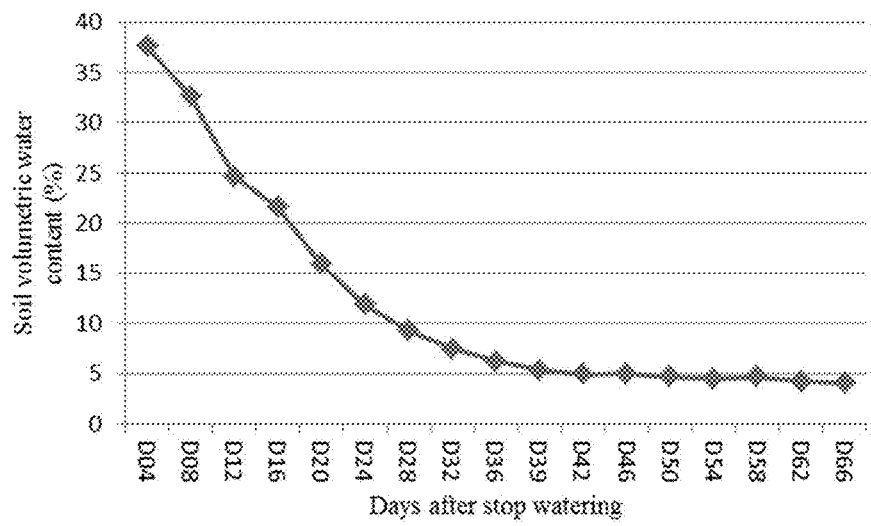
FIG. 3 shows changes of soil volumetric water content at different developmental stage for drought testing OsMtN3L transgenic rice in Hainan field. The OsMtN3L transgenic rice started heading at 36 days after stopping watering.

Twelve OsMtN3L transgenic rice plants were tested in Hainan field. ZH11-TC and DP0158 rice plants planted nearby were used as controls. When the main stem panicles reached panicle initiation stage II-IV, and the tiller panicles reached panicle initiation stage I, watering was stopped. The soil volumetric water content decreased from 43% to 5% during panicle heading and maturation stage (FIG. 3). 19 days after stopping watering, the main stem panicles reached panicle initiation stage IX, the tiller panicles reached panicle initiation stage VI-VII, and the rice plants began to show leaf roll phenotype. One transgenic line DP0902.03 showed less leaf roll degree and greener than control. At the maturation stage, four transgenic rice lines DP0902.03, DP0902.07, DP0902.11 and DP0902.12 showed better seed setting phenotype.

At the end of the growing season, about six representative plants from each transgenic line were harvested from the middle of the row per line, and grain yield per plant was measured. The grain yield per plant of OsMtN3L transgenic rice was greater than ZH11-TC control and significantly greater than DP0158 control at the construct level. Three OsMtN3L transgenic lines showed significantly greater grain yield per plants than ZH11-TC plants, and eight transgenic lines showed significantly greater grain yield per plants than DP0158 control plants. The four transgenic lines which showed better seed setting rates exhibited significantly greater grain yield per plant than DP0158 control (Table 22). These results indicate that OsMtN3L transgenic rice plant is tolerance to drought conditions, and over-expression of OsMtN3L increased drought tolerance at seedling stage and may increase the grain yield per plant after drought stress at flowering stage.

TABLE 22

Grain yield analysis of OsMtN3L transgenic rice plants under field drought conditions (1$^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0902 (construct) | 462 | 282 | 7.10 | 0.89 | 0.311 | | 2.44 | 0.006 | Y |
| ZH11-TC | 40 | 23 | 6.21 | | | | | | |
| DP0158 | 38 | 23 | 4.66 | | | | | | |
| DP0902.01 | 38 | 24 | 6.11 | −0.11 | 0.916 | | 1.44 | 0.158 | |
| DP0902.02 | 40 | 24 | 7.59 | 1.38 | 0.178 | | 2.93 | 0.004 | Y |
| DP0902.03 | 40 | 24 | 7.95 | 1.73 | 0.085 | Y | 3.28 | 0.001 | Y |
| DP0902.04 | 38 | 24 | 6.13 | −0.09 | 0.932 | | 1.46 | 0.155 | |
| DP0902.05 | 40 | 24 | 6.81 | 0.59 | 0.555 | | 2.14 | 0.036 | Y |
| DP0902.06 | 40 | 24 | 5.75 | −0.46 | 0.650 | | 1.09 | 0.282 | |
| DP0902.07 | 40 | 24 | 9.08 | 2.87 | 0.005 | Y | 4.42 | 0.000 | Y |
| DP0902.08 | 29 | 18 | 8.21 | 2.00 | 0.047 | Y | 3.55 | 0.001 | Y |
| DP0902.09 | 38 | 24 | 7.67 | 1.46 | 0.154 | | 3.00 | 0.003 | Y |
| DP0902.10 | 40 | 24 | 6.28 | 0.07 | 0.946 | | 1.62 | 0.113 | |
| DP0902.11 | 40 | 24 | 6.92 | 0.71 | 0.488 | | 2.26 | 0.028 | Y |
| DP0902.12 | 39 | 24 | 6.77 | 0.55 | 0.586 | | 2.10 | 0.034 | Y |

The second experiment was performed in Ningxia province, the twelve OsMtN3L transgenic lines were tested.

Figure 4:
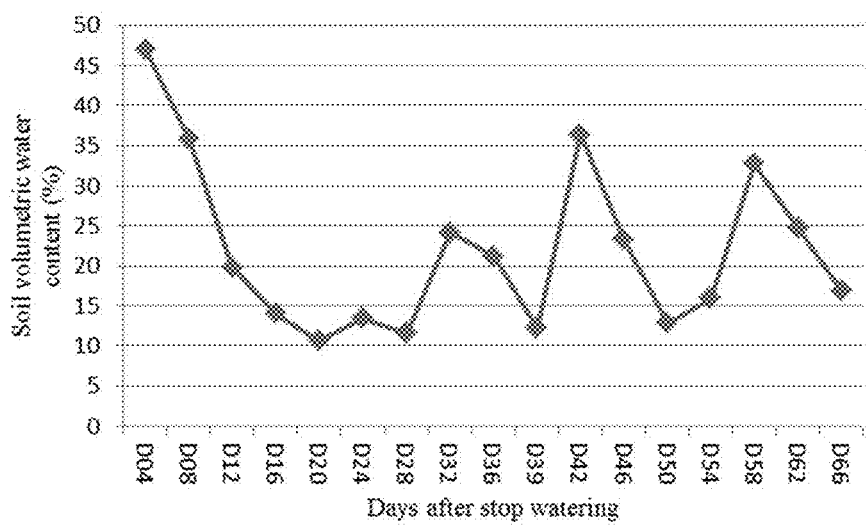
FIG. 4 shows changes of soil volumetric water content at different developmental stage for drought testing OsMtN3L transgenic rice in Ningxia field. The OsMtN3L transgenic rice started heading at 47 days after stopping watering.

When 20% of the main stem panicles reached panicle initiation stage II, watering was stopped. The soil volumetric water content decreased from 47% to 10% during panicle heading stage (FIG. 4). The rainfall resulted in variation for the soil volumetric water content during drought stress. 18 days after stopping watering, the main stem panicles reached panicle initiation stage IV-V, the tiller panicle reached panicle initiation stage III-IV, and the rice plants showed leaf rolling phenotype.

As shown in Table 23, OsMtN3L transgenic rice exhibited significantly greater grain yield per plant than both ZH11-TC and DP0158 controls at the construct level. Five OsMtN3L transgenic lines had significantly greater grain yields per plant than ZH11-TC control, and nine lines had significantly greater grain yields per plant than DP0158 control. Two transgenic lines DP0902.07 and DP0902.11 showed the greatest grain yields per plants in the two experiments. These results further demonstrate that OsMtN3L transgenic rice plant is tolerance to drought, and over-expression of OsMtN3L increases the grain yield per plant after drought stress at flowering and heading stage.

TABLE 23

Grain yield analysis of OsMtN3L transgenic rice plants under field drought conditions ($2^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0902 (construct) | 473 | 286 | 3.05 | 1.03 | 0.096 | Y | 1.71 | | Y |
| ZH11-TC | 29 | 18 | 2.02 | | | | | | |
| DP0158 | 37 | 24 | 1.33 | | | | | | |
| DP0902.01 | 40 | 24 | 2.69 | 0.67 | 0.337 | | 1.35 | 0.027 | Y |
| DP0902.02 | 40 | 23 | 2.98 | 0.96 | 0.165 | | 1.65 | 0.011 | Y |
| DP0902.04 | 39 | 24 | 3.33 | 1.31 | 0.049 | Y | 2.00 | 0.002 | Y |
| DP0902.05 | 40 | 24 | 2.63 | 0.61 | 0.359 | | 1.29 | 0.036 | Y |
| DP0902.06 | 40 | 24 | 1.82 | −0.20 | 0.776 | | 0.49 | 0.448 | |
| DP0902.07 | 37 | 24 | 4.07 | 2.05 | 0.003 | Y | 2.74 | 0.000 | Y |
| DP0902.08 | 41 | 24 | 2.33 | 0.31 | 0.657 | | 1.00 | 0.122 | |
| DP0902.09 | 38 | 24 | 2.23 | 0.20 | 0.772 | | 0.89 | 0.173 | |
| DP0902.10 | 40 | 24 | 2.67 | 0.65 | 0.356 | | 1.34 | 0.041 | Y |
| DP0902.11 | 40 | 24 | 4.82 | 2.79 | 0.000 | Y | 3.48 | 0.000 | Y |
| DP0902.13 | 39 | 23 | 3.61 | 1.59 | 0.023 | Y | 2.28 | 0.000 | Y |
| DP0902.15 | 39 | 24 | 3.39 | 1.37 | 0.030 | Y | 2.06 | 0.001 | Y |

3) Field DRT Validation Results of OsDN-DTP6 (DP0935) Transgenic Rice

Figure 5:
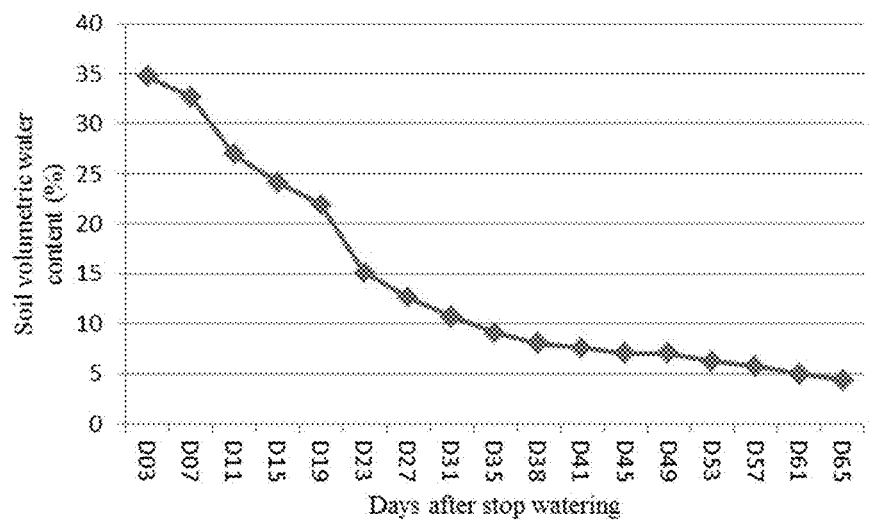
FIG. 5 shows changes of soil volumetric water content at different developmental stage for drought testing OsDN-DTP6 and OsANKL1 transgenic rice in the Hainan experiment. The OsDN-DTP6 and OsANKL1 transgenic rice plants started heading at 38 days after stopping watering.

Twelve OsDN-DTP6 transgenic lines were tested in Hainan in the first experiment. Watering was stopped when the main stem panicles reached panicle initiation II. The soil volumetric water content decreased from 35% to 5% during heading and maturation stage (FIG. 5). When the main stem panicles headed out and the tiller panicles reached panicle initiation stage VII-VIII, the rice plants showed drought stress phenotype such as leaf rolling and leaf yellow. Six transgenic lines DP0935.01, DP0935.03, DP0935.07, DP0935.14, DP0935.15 and DP0935.17 exhibited less leaf rolling degree. As shown in Table 24, the OsDN-DTP6 transgenic rice plants showed significantly greater grain yield per plant than both ZH11-TC and DP0158 controls at the construct level. Eight transgenic lines exhibited significantly greater grain yields per plant than both ZH11-TC and DP0158 controls at the line level. These results demonstrate that OsDN-DTP6 transgenic rice plant is tolerant to drought stress and over-expression of OsDN-DTP6 increased the grain yield per plant after drought stress at flowering stage.

TABLE 24

Grain yield analysis of OsDN-DTP6 transgenic rice plants under field drought conditions ($1^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0935 (construct) | 475 | 290 | 4.09 | 1.28 | 0.015 | Y | 1.37 | 0.009 | Y |
| ZH11-TC | 40 | 24 | 2.81 | | | | | | |

TABLE 24-continued

Grain yield analysis of OsDN-DTP6 transgenic rice plants under field drought conditions (1st experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0158 | 40 | 23 | 2.72 | | | | | | |
| DP0935.01 | 40 | 22 | 2.62 | −0.20 | 0.727 | | −0.10 | 0.859 | |
| DP0935.03 | 40 | 25 | 3.56 | 0.74 | 0.180 | | 0.84 | 0.136 | |
| DP0935.04 | 38 | 24 | 3.82 | 1.00 | 0.076 | Y | 1.10 | 0.045 | Y |
| DP0935.05 | 37 | 25 | 4.07 | 1.25 | 0.027 | Y | 1.35 | 0.017 | Y |
| DP0935.06 | 40 | 24 | 3.01 | 0.20 | 0.723 | | 0.29 | 0.593 | |
| DP0935.07 | 40 | 25 | 3.86 | 1.05 | 0.064 | Y | 1.15 | 0.042 | Y |
| DP0935.09 | 40 | 25 | 3.27 | 0.45 | 0.424 | | 0.55 | 0.329 | |
| DP0935.13 | 40 | 24 | 6.06 | 3.25 | 0.000 | Y | 3.35 | 0.000 | Y |
| DP0935.14 | 40 | 24 | 4.57 | 1.76 | 0.001 | Y | 1.86 | 0.001 | Y |
| DP0935.15 | 40 | 24 | 4.07 | 1.25 | 0.027 | Y | 1.35 | 0.015 | Y |
| DP0935.17 | 40 | 24 | 5.74 | 2.92 | 0.000 | Y | 3.02 | 0.000 | Y |
| DP0935.18 | 40 | 24 | 4.44 | 1.62 | 0.004 | Y | 1.72 | 0.002 | Y |

The second experiment was performed in Hainan province; the same twelve OsDN-DTP6 transgenic lines were tested. Watering was stopped when the main stem panicles reached to panicle initiation stage III-V and the tiller panicles reached to panicle initiation stage II. The soil volumetric water content decreased from 24% to 6% during heading stage (FIG. 6). 52 days after stopping watering, the main stem panicles reached milk mature stage and the rice plants started to show leaf rolling phenotype. Two transgenic lines DP0935.13 and DP0935.17 showed good seed setting at the mature stage. The OsDN-DTP6 transgenic rice plants showed greater grain yield per plant than ZH11-TC control and significantly greater grain yield per plant than DP0158 control at the construct level. Analysis at line level showed that ten OsDN-DTP6 transgenic lines showed significantly greater grain yield per plant than the DP0158 control, and four transgenic lines showed significantly greater grain yield per plant than ZH11-TC control plants (Table 25). These results further demonstrate that OsDN-DTP6 over-expressed transgenic rice plant is drought to drought stress, and over-expression of OsDN-DTP6 increased the drought tolerance and then increased the grain yield per plant.

4) Field DRT Validation Results of OsANKL1 (DP0960) Transgenic Rice

Twelve OsANKL1 transgenic rice plants were tested in Hainan field. ZH11-TC and DP0158 rice plants were used as controls. When the main stem panicles reached panicle initiation stage I-II, watering was stopped. The soil volumetric water content decreased from 35% to 5% during panicle heading and maturation stage (FIG. 5). 25 days after stopping watering, the main stem panicles headed out, the tiller panicles reached panicle initiation stage VI-VII, and the rice plants began to show leaf roll phenotype. During the drought stress, six OsANKL1 transgenic lines DP0960.01, DP0960.02, DP0960.09, DP0960.10, DP0960.11 and DP0960.12 showed drought tolerance phenotype such as less leaf rolling degree and less drying leaf than control plants. Five lines DP0960.01, DP0960.02, DP0960.07, DP0960.09 and DP0960.11 showed better seed setting at the maturation stage.

At the end of the growing season, the grain yield per plant was measured. The grain yield per plant of OsANKL1 transgenic rice was significantly greater than both ZH11-TC and DP0158 control at the construct level. Eight OsANKL1

TABLE 25

Grain yield analysis of OsDN-DTP6 transgenic rice plants under field drought conditions (2nd experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0935 | 479 | 288 | 6.64 | 1.36 | 0.167 | | 3.53 | 0.000 | Y |
| ZH11-TC | 39 | 24 | 5.28 | | | | | | |
| DP0158 | 40 | 24 | 3.10 | | | | | | |
| DP0935.01 | 40 | 24 | 4.80 | −0.48 | 0.654 | | 1.70 | 0.117 | |
| DP0935.03 | 40 | 24 | 5.99 | 0.71 | 0.515 | | 2.88 | 0.008 | Y |
| DP0935.04 | 40 | 24 | 8.53 | 3.25 | 0.003 | Y | 5.42 | 0.000 | Y |
| DP0935.05 | 40 | 24 | 6.16 | 0.89 | 0.413 | | 3.06 | 0.005 | Y |
| DP0935.06 | 40 | 24 | 4.86 | −0.42 | 0.696 | | 1.75 | 0.102 | |
| DP0935.07 | 40 | 24 | 8.45 | 3.17 | 0.003 | Y | 5.35 | 0.000 | Y |
| DP0935.09 | 40 | 24 | 5.49 | 0.21 | 0.842 | | 2.39 | 0.027 | Y |
| DP0935.13 | 40 | 24 | 9.46 | 4.18 | 0.000 | Y | 6.36 | 0.000 | Y |
| DP0935.14 | 40 | 24 | 5.90 | 0.62 | 0.564 | | 2.80 | 0.009 | Y |
| DP0935.15 | 40 | 24 | 6.50 | 1.22 | 0.264 | | 3.39 | 0.002 | Y |
| DP0935.17 | 39 | 24 | 7.44 | 2.16 | 0.044 | Y | 4.33 | 0.000 | Y |
| DP0935.18 | 40 | 24 | 6.05 | 0.77 | 0.501 | | 2.95 | 0.010 | Y | transgenic lines showed significantly greater grain yield per plants than ZH11-TC plants, and nine transgenic lines showed significantly greater grain yield per plants than DP0158 control plants (Table 26). These results indicate that OsANKL1 transgenic rice plant is tolerance to drought conditions, and over-expression of OsANKL1 increased drought tolerance at seedling stage and increased the grain yield per plant after drought stress at flowering stage.

Grain yield analysis showed that OsANKL1 transgenic rice plants exhibited significantly greater grain yield per plant than ZH11-TC and DP0158 controls at the construct level. Six OsANKL1 transgenic lines exhibited significantly greater grain yield per plant than ZH11-TC and DP0158 control at the line level (Table 27). These results further indicate that OsANKL1 transgenic rice plant gained drought tolerance and exhibited grain yield increase per plant.

TABLE 26

Grain yield analysis of OsANKL1 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0960 (construct) | | | 5.20 | 1.93 | 0.000 | Y | 2.23 | 0.000 | Y |
| ZH11-TC | 40 | 24 | 3.27 | | | | | | |
| DP0158 | 39 | 24 | 2.97 | | | | | | |
| DP0960.01 | 37 | 24 | 6.31 | 3.04 | 0.000 | Y | 3.33 | 0.000 | Y |
| DP0960.02 | 40 | 25 | 6.26 | 2.99 | 0.000 | Y | 3.28 | 0.000 | Y |
| DP0960.03 | 40 | 24 | 5.33 | 2.06 | 0.000 | Y | 2.35 | 0.000 | Y |
| DP0960.04 | 40 | 24 | 4.19 | 0.92 | 0.105 | | 1.21 | 0.029 | Y |
| DP0960.05 | 40 | 24 | 6.34 | 3.08 | 0.000 | Y | 3.37 | 0.000 | Y |
| DP0960.07 | 40 | 24 | 6.31 | 3.04 | 0.000 | Y | 3.33 | 0.000 | Y |
| DP0960.09 | 40 | 24 | 7.21 | 3.94 | 0.000 | Y | 4.23 | 0.000 | Y |
| DP0960.10 | 40 | 24 | 3.73 | 0.46 | 0.412 | | 0.76 | 0.161 | |
| DP0960.11 | 40 | 24 | 5.00 | 1.73 | 0.002 | Y | 2.03 | 0.000 | Y |
| DP0960.12 | 39 | 23 | 3.89 | 0.62 | 0.271 | | 0.92 | 0.107 | |
| DP0960.13 | 39 | 26 | 4.54 | 1.28 | 0.019 | Y | 1.57 | 0.006 | Y |
| DP0960.15 | 40 | 24 | 3.32 | 0.05 | 0.925 | | 0.35 | 0.537 | |

Figure 6:
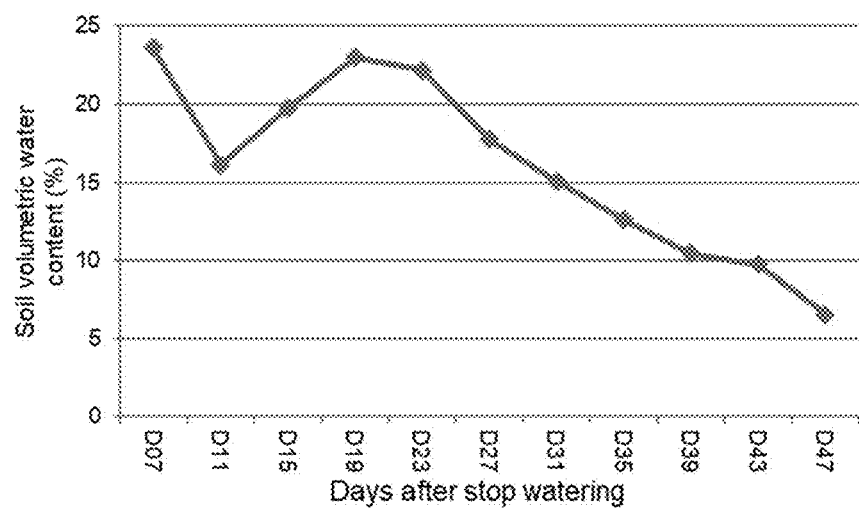
FIG. 6 shows changes of soil volumetric water content at different developmental stage for drought testing OsDN-DTP6 and OsANKL1 transgenic rice in the second experiment. The OsDN-DTP6 and OsANKL1 transgenic rice plants started heading at 32 days after stopping watering.

The same 12 OsANKL1 transgenic rice plants were tested again in Hainan field. Watering was stopped when the main stem panicles reached panicle initiation stage III-V and the tiller panicles reached panicle initiation stage II. 52 days after stopping watering, the main stem panicles reached milk mature stage, and the rice plants started to show drought stress phenotype. The soil volumetric water content decreased from 24% to 6% during heading stage (FIG. 6). Two transgenic lines DP0960.03 and DP0960.07 showed good seed setting phenotype at mature stage.

TABLE 27

Grain yield analysis of OsANKL1 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0960 (Construct) | 478 | 285 | 6.24 | 1.74 | 0.077 | Y | 2.41 | 0.014 | Y |
| ZH11-TC | 40 | 24 | 4.50 | | | | | | |
| DP0158 | 40 | 24 | 3.83 | | | | | | |
| DP0960.01 | 40 | 24 | 8.75 | 4.25 | 0.000 | Y | 4.92 | 0.000 | Y |
| DP0960.02 | 40 | 24 | 6.72 | 2.22 | 0.042 | Y | 2.89 | 0.008 | Y |
| DP0960.03 | 39 | 24 | 8.82 | 4.32 | 0.000 | Y | 4.99 | 0.000 | Y |
| DP0960.04 | 40 | 24 | 5.18 | 0.68 | 0.527 | | 1.35 | 0.211 | |
| DP0960.05 | 40 | 24 | 7.03 | 2.53 | 0.019 | Y | 3.20 | 0.003 | Y |
| DP0960.07 | 40 | 24 | 8.41 | 3.91 | 0.000 | Y | 4.58 | 0.000 | Y |
| DP0960.09 | 40 | 24 | 8.38 | 3.88 | 0.000 | Y | 4.55 | 0.000 | Y |
| DP0960.10 | 40 | 24 | 3.82 | −0.68 | 0.531 | | −0.01 | 0.996 | |
| DP0960.11 | 40 | 24 | 6.22 | 1.72 | 0.111 | | 2.39 | 0.028 | Y |
| DP0960.12 | 40 | 24 | 4.65 | 0.16 | 0.885 | | 0.83 | 0.442 | |
| DP0960.13 | 39 | 21 | 4.08 | −0.42 | 0.698 | | 0.25 | 0.815 | |
| DP0960.15 | 40 | 24 | 2.85 | −1.64 | 0.128 | | −0.97 | 0.358 | |

5) Field DRT Validation Results of OsMBD2 (DP0988) Transgenic Rice

Figure 7:
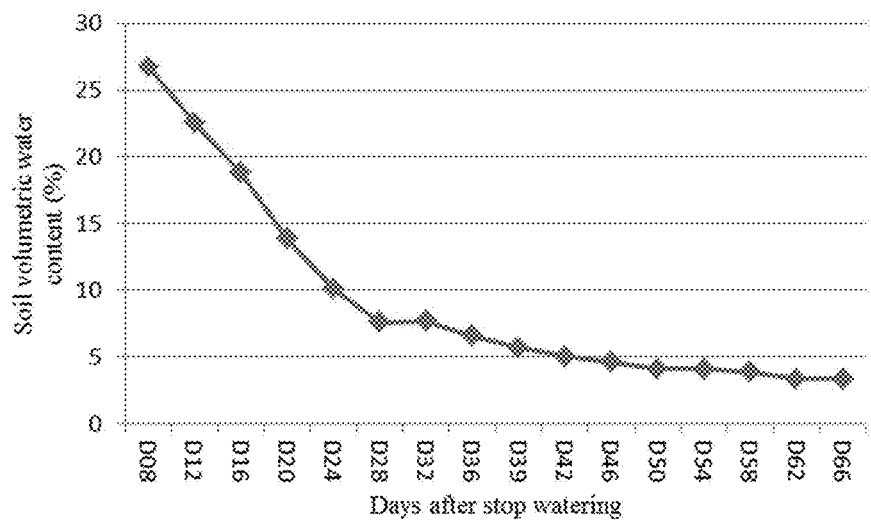
FIG. 7 shows changes of soil volumetric water content at different developmental stage for drought testing OsMBD2 transgenic rice in the Hainan experiment. The OsMBD2 transgenic rice started heading at 37 days after stopping watering.

Twelve OsMBD2 transgenic rice plants were tested in Hainan field. ZH11-TC and DP0158 rice plants planted were used as controls. When the main stem panicles reached panicle initiation stage II-III, watering was stopped. The soil volumetric water content decreased from 27% to 4% during panicle heading and maturation stage (FIG. 7). 24 days after stopping watering, the main stem panicles headed out, the tiller panicles reached panicle initiation stage VI-VII, and the rice plants began to show leaf roll phenotype. The OsMBD2 transgenic lines showed less leaf rolling degree and less drying leaf than control plants during the drought stress, or showed better seed setting at the maturation stage except transgenic lines DP0988.03, DP0988.04 and DP0988.05.

The grain yield analysis showed that the grain yield per plant of OsMBD2 transgenic rice was significantly greater than both ZH11-TC and DP0158 control at the construct level. Ten OsMBD2 transgenic lines showed significantly greater grain yields per plants than ZH11-TC plants, and all OsMBD2 transgenic lines showed significantly greater grain yields per plants than DP0158 control plants (Table 28). These results indicate that OsMBD2 transgenic rice plant is tolerance to drought conditions, and over-expression of OsMBD2 increased drought tolerance at seedling stage and increased the grain yield per plant after drought stress at flowering stage.

TABLE 28

Grain yield analysis of OsMBD2 transgenic rice plants under field drought conditions (1st experiment)

| Line ID | Number of survival plants | Number of harvested plants | Yield per plant (g) | CK = ZH11-TC | | | CK = DP0158 | | |
| --- | --- | --- | --- | --- | --- | --- | --- | --- | --- |
| | | | | Diff | P value | P ≤ 0.1 | Diff | P value | P ≤ 0.1 |
| DP0988 (construct) | 423 | 224 | 3.24 | 1.60 | 0.004 | Y | 2.09 | 0.001 | Y |
| ZH11-TC | 36 | 20 | 1.64 | | | | | | |
| DP0158 | 35 | 14 | 1.15 | | | | | | |
| DP0988.01 | 35 | 19 | 2.58 | 0.94 | 0.142 | | 1.43 | 0.044 | Y |
| DP0988.02 | 36 | 19 | 3.46 | 1.82 | 0.005 | Y | 2.31 | 0.001 | Y |
| DP0988.03 | 36 | 19 | 2.76 | 1.12 | 0.080 | Y | 1.60 | 0.022 | Y |
| DP0988.04 | 36 | 19 | 3.09 | 1.45 | 0.020 | Y | 1.94 | 0.006 | Y |
| DP0988.05 | 35 | 19 | 3.36 | 1.72 | 0.006 | Y | 2.20 | 0.002 | Y |
| DP0988.06 | 33 | 17 | 3.33 | 1.70 | 0.008 | Y | 2.18 | 0.002 | Y |
| DP0988.07 | 35 | 19 | 3.88 | 2.24 | 0.000 | Y | 2.73 | 0.000 | Y |
| DP0988.08 | 36 | 20 | 2.62 | 0.98 | 0.126 | | 1.47 | 0.039 | Y |
| DP0988.09 | 35 | 19 | 4.04 | 2.40 | 0.000 | Y | 2.89 | 0.000 | Y |
| DP0988.10 | 35 | 19 | 2.96 | 1.32 | 0.035 | Y | 1.81 | 0.011 | Y |
| DP0988.11 | 36 | 15 | 3.81 | 2.17 | 0.001 | Y | 2.65 | 0.000 | Y |
| DP0988.12 | 35 | 20 | 3.00 | 1.36 | 0.033 | Y | 1.85 | 0.009 | Y |

Figure 8:
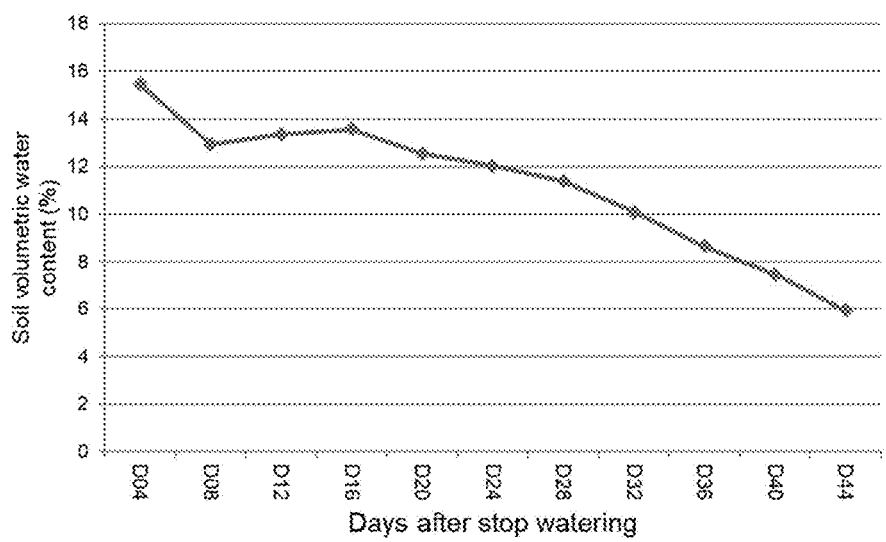
FIG. 8 shows changes of soil volumetric water content at different developmental stage for drought testing OsMBD2 transgenic rice in the second experiment. The OsMBD2 transgenic rice started heading at 33 days after stopping watering.

The same 12 OsMBD2 transgenic rice plants were tested again in Hainan field. Watering was stopped when the main stem panicles reached panicle initiation stage IV-V and the tiller panicles reached panicle initiation stage II-III. 52 days after stopping watering, the main stem panicles reached milk mature stage, and the rice plants started to show drought stress phenotype. The soil volumetric water content decreased from 16% to 6% during heading stage (FIG. 8).

Grain yield analysis showed that OsMBD2 transgenic rice plants exhibited significantly greater grain yield per plant than ZH11-TC and DP0158 controls at the construct level. All the OsMBD2 transgenic lines exhibited greater grain yields per plant than ZH11-TC and DP0158 controls at the line level (Table 29). These results further indicate that OsMBD2 transgenic rice plant gained drought tolerance and exhibited greater grain yield increase per plant.

TABLE 29

Grain yield analysis of OsMBD2 transgenic rice plants under field drought conditions (2nd experiment)

| Line ID | Number of survival plants | Number of harvested plants | Yield per plant (g) | CK = ZH11-TC | | | CK = DP0158 | | |
| --- | --- | --- | --- | --- | --- | --- | --- | --- | --- |
| | | | | Diff | P value | P ≤ 0.1 | Diff | P value | P ≤ 0.1 |
| DP0988 (Construct) | 420 | 257 | 3.68 | 1.30 | 0.075 | Y | 1.32 | 0.070 | Y |
| ZH11-TC | 40 | 24 | 2.38 | | | | | | |
| DP0158 | 33 | 19 | 2.35 | | | | | | |
| DP0988.01 | 28 | 18 | 2.50 | 0.13 | 0.885 | | 0.15 | 0.862 | |
| DP0988.02 | 29 | 18 | 3.24 | 0.86 | 0.332 | | 0.89 | 0.317 | |
| DP0988.03 | 33 | 19 | 4.30 | 1.92 | 0.029 | Y | 1.95 | 0.028 | Y |
| DP0988.04 | 33 | 19 | 3.53 | 1.16 | 0.173 | | 1.18 | 0.159 | |
| DP0988.05 | 31 | 19 | 3.74 | 1.37 | 0.124 | | 1.39 | 0.117 | |

TABLE 29-continued

Grain yield analysis of OsMBD2 transgenic rice plants under field drought conditions (2nd experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0988.06 | 37 | 23 | 4.25 | 1.87 | 0.026 | Y | 1.90 | 0.022 | Y |
| DP0988.07 | 37 | 24 | 4.85 | 2.47 | 0.004 | Y | 2.50 | 0.003 | Y |
| DP0988.08 | 40 | 24 | 3.49 | 1.11 | 0.192 | | 1.14 | 0.182 | |
| DP0988.09 | 37 | 24 | 3.97 | 1.60 | 0.058 | Y | 1.62 | 0.054 | Y |
| DP0988.10 | 40 | 24 | 3.17 | 0.79 | 0.348 | | 0.82 | 0.337 | |
| DP0988.11 | 35 | 21 | 3.33 | 0.96 | 0.255 | | 0.98 | 0.247 | |
| DP0988.12 | 40 | 24 | 3.72 | 1.34 | 0.115 | | 1.37 | 0.104 | |

6) Field DRT Validation Results of OsTP1 (DP1082) Transgenic Rice

Figure 9:
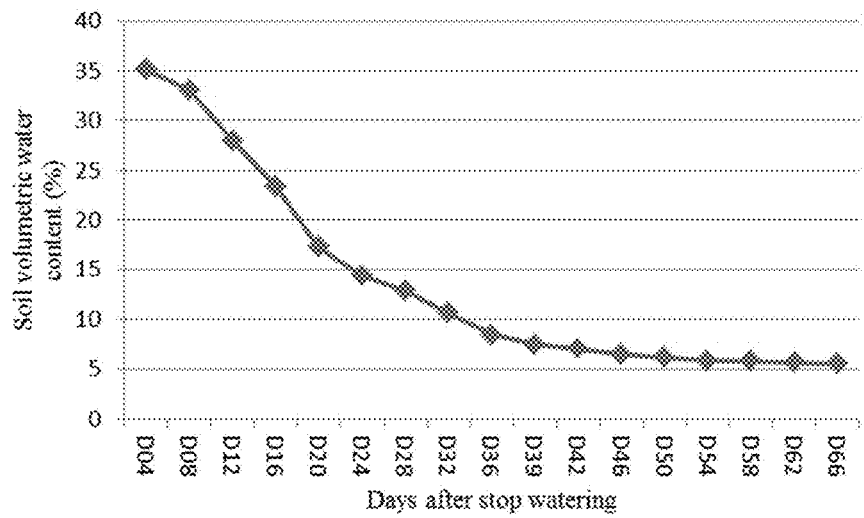
FIG. 9 shows changes of soil volumetric water content at different developmental stage for drought testing OsTP1 and OsACOAT1 transgenic rice in the Hainan experiment. The OsTP1 and OsACOAT1 transgenic rice started heading at 37 days after stopping watering.

Twelve OsTP1 transgenic lines were tested in Hainan field. Watering was stopped from panicle initiation stage II of the main stem panicles to produce heavier drought stress. The soil volumetric moisture content decreased from about 35% to 5% during the heading and maturation stages (FIG. 9). Two OsTP1 transgenic lines DP1082.03 and DP1082.06 showed greener leaf and less leaf roll degree compared with the ZH11-TC and DP0158 controls planted nearby. DP1082.04, DP1082.10, DP1082.11 and DP1082.12 showed better seed setting rate at the maturation stage.

The grain yield per plant of OsTP1 transgenic rice was more than ZH11-TC and significantly more than DP0158 control at the construct level. Five OsTP1 transgenic lines showed significantly greater grain yields per plant than ZH11-TC control and eight lines showed significantly greater grain yields per plant than DP0158 control at the line level (Table 30). These results demonstrate that OsTP1 transgenic rice plants had improved drought tolerance at seedling stage and improve the grain yield per plant after drought stress.

The same twelve OsTP1 transgenic lines were tested again in Ningxia field. Watering was stopped when 10% of the main stem panicles reached panicle initiation stage II. The soil volumetric water content decreased from 45% to 5% during heading stage (FIG. 10). 26 days after stopping watering, the rainfall changed the soil volumetric water content in the field. Three lines DP1082.03, DP1082.11 and DP1082.12 showed better seeds setting phenotype. The grain yield analysis showed that OsTP1 transgenic rice had lower grain yield per plant than ZH11-TC but significantly greater grain yield per plant than DP0158 control plants (Table 31). These results demonstrate that OsTP1 over-expressed transgenic rice plant obtained drought tolerance at seedling stage and over-expression of OsTP1 may improve the drought tolerance.

TABLE 30

Grain yield analysis of OsTP1 transgenic rice plants under field drought conditions (1st experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP1082 (construct) | 473 | 288 | 5.94 | 1.02 | 0.154 | | 2.13 | 0.003 | Y |
| ZH11-TC | 40 | 24 | 4.91 | | | | | | |
| DP0158 | 40 | 24 | 3.81 | | | | | | |
| DP1082.01 | 39 | 24 | 4.64 | −0.27 | 0.731 | | 0.83 | 0.274 | |
| DP1082.03 | 40 | 24 | 7.31 | 2.40 | 0.002 | Y | 3.50 | 0.000 | Y |
| DP1082.04 | 40 | 24 | 6.28 | 1.37 | 0.083 | Y | 2.47 | 0.002 | Y |
| DP1082.05 | 40 | 24 | 4.62 | −0.30 | 0.704 | | 0.80 | 0.306 | |
| DP1082.06 | 38 | 24 | 5.78 | 0.86 | 0.261 | | 1.96 | 0.012 | Y |
| DP1082.08 | 40 | 24 | 5.64 | 0.73 | 0.340 | | 1.83 | 0.019 | Y |
| DP1082.09 | 37 | 24 | 5.08 | 0.16 | 0.837 | | 1.26 | 0.108 | |
| DP1082.10 | 40 | 24 | 7.20 | 2.28 | 0.004 | Y | 3.39 | 0.000 | Y |
| DP1082.11 | 40 | 24 | 7.31 | 2.39 | 0.003 | Y | 3.49 | 0.000 | Y |
| DP1082.12 | 40 | 24 | 7.65 | 2.73 | 0.001 | Y | 3.83 | 0.000 | Y |
| DP1082.13 | 39 | 24 | 4.57 | −0.35 | 0.680 | | 0.76 | 0.363 | |
| DP1082.15 | 40 | 24 | 5.20 | 0.29 | 0.714 | | 1.39 | 0.076 | Y |

TABLE 31

Grain yield analysis of OsTP1 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1082 (construct) | 477 | 283 | 4.51 | −1.50 | 0.046 |   | 1.70 | 0.024 | Y |
| ZH11-TC | 41 | 23 | 6.00 |   |   |   |   |   |   |
| DP0158 | 39 | 24 | 2.81 |   |   |   |   |   |   |
| DP1082.01 | 40 | 24 | 3.80 | −2.20 | 0.010 |   | 0.99 | 0.246 |   |
| DP1082.03 | 39 | 23 | 5.22 | −0.79 | 0.382 |   | 2.40 | 0.008 | Y |
| DP1082.04 | 40 | 23 | 3.78 | −2.23 | 0.009 |   | 0.96 | 0.260 |   |
| DP1082.05 | 40 | 24 | 4.18 | −1.83 | 0.032 |   | 1.37 | 0.109 |   |
| DP1082.06 | 40 | 24 | 4.31 | −1.70 | 0.046 |   | 1.49 | 0.081 | Y |
| DP1082.08 | 41 | 22 | 4.64 | −1.37 | 0.109 |   | 1.82 | 0.033 | Y |
| DP1082.09 | 39 | 24 | 3.47 | −2.54 | 0.003 |   | 0.66 | 0.442 |   |
| DP1082.10 | 40 | 24 | 5.11 | −0.90 | 0.293 |   | 2.29 | 0.007 | Y |
| DP1082.11 | 40 | 24 | 6.08 | 0.08 | 0.927 |   | 3.27 | 0.000 | Y |
| DP1082.12 | 40 | 24 | 4.58 | −1.43 | 0.095 |   | 1.77 | 0.039 | Y |
| DP1082.13 | 39 | 23 | 3.10 | −2.91 | 0.001 |   | 0.28 | 0.741 |   |
| DP1082.15 | 39 | 24 | 5.85 | −0.15 | 0.861 |   | 3.04 | 0.000 | Y |

7) Field DRT Validation Results of OsACOAT1 (DP1121) Transgenic Rice

Twelve OsACOAT1 transgenic lines were tested in Hainan Province in the first experiment. Watering was stopped from initiation stage II of main stem panicles to seed maturity to produce heavier drought stress. The soil volumetric water content decreased from 35% to 5% during heading and maturation stage (FIG. 9). 26 days after stopping watering, the main stem panicles headed out, the tiller panicles were at panicle initiation VII-VIII stage, and some rice plants exhibited phenotypes such as leaf rolling. The transgenic rice plants DP1121.06 and DP1121.08 exhibited drought tolerance phenotypes such as greener leaf and less leaf rolling degree. At the end of the planting season, the transgenic rice plants DP1121.01, DP1121.02, DP1121.04, DP1121.06, DP1121.08 and DP1121.09 exhibited good seed setting rate.

The grain yield per plant is shown in Table 32, the OsACOAT1 transgenic rice plants showed significantly greater grain yield per plant than both ZH11-TC and DP0158 plants at the construct level. Seven OsACOAT1 transgenic rice lines showed significantly greater grain yields per plant than both ZH11-TC and DP0158 plants at the line level. These results demonstrate that OsACOAT1 rice plant had greater grain yield per plant than control after drought stress.

TABLE 32

Grain yield analysis of OsACOAT1 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1121 (construct) | 478 | 288 | 6.69 | 1.82 | 0.010 | Y | 1.96 | 0.005 | Y |
| ZH11-TC | 40 | 24 | 4.87 |   |   |   |   |   |   |
| DP0158 | 40 | 24 | 4.73 |   |   |   |   |   |   |
| DP1121.01 | 40 | 24 | 7.96 | 3.09 | 0.000 | Y | 3.23 | 0.000 | Y |
| DP1121.02 | 40 | 24 | 7.72 | 2.85 | 0.000 | Y | 2.99 | 0.000 | Y |
| DP1121.03 | 40 | 24 | 7.28 | 2.40 | 0.002 | Y | 2.55 | 0.001 | Y |
| DP1121.04 | 40 | 24 | 8.85 | 3.97 | 0.000 | Y | 4.12 | 0.000 | Y |
| DP1121.05 | 40 | 24 | 3.44 | −1.44 | 0.067 |   | −1.29 | 0.099 |   |
| DP1121.06 | 40 | 24 | 8.71 | 3.83 | 0.000 | Y | 3.98 | 0.000 | Y |
| DP1121.07 | 39 | 24 | 4.53 | −0.35 | 0.636 |   | −0.21 | 0.791 |   |
| DP1121.08 | 39 | 24 | 7.21 | 2.33 | 0.003 | Y | 2.48 | 0.001 | Y |
| DP1121.09 | 40 | 24 | 7.79 | 2.91 | 0.000 | Y | 3.06 | 0.000 | Y |
| DP1121.10 | 40 | 24 | 5.78 | 0.91 | 0.233 |   | 1.05 | 0.174 |   |
| DP1121.11 | 40 | 24 | 5.73 | 0.85 | 0.273 |   | 1.00 | 0.185 |   |
| DP1121.12 | 40 | 24 | 5.30 | 0.43 | 0.586 |   | 0.57 | 0.449 |   |

Figure 10:
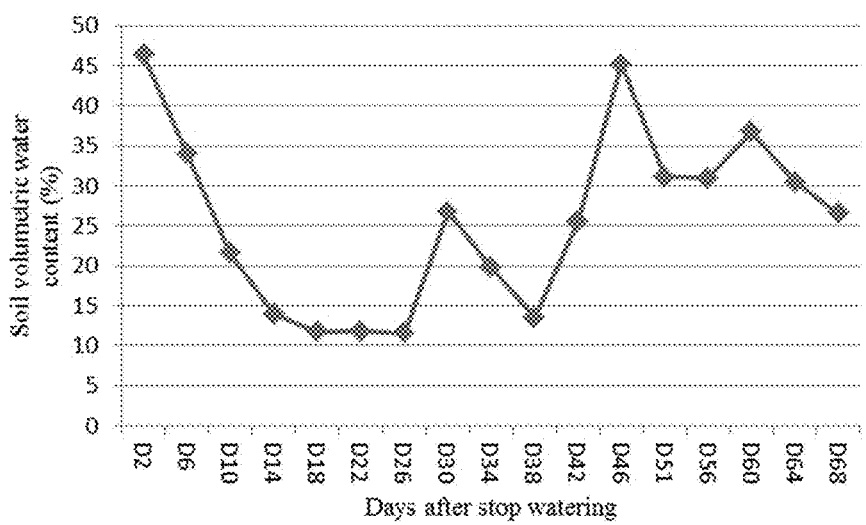
FIG. 10 shows changes of soil volumetric water content at different developmental stage for drought testing OsTP1 and OsACOAT1 transgenic rice in the Ningxia experiment. The OsTP1 and OsACOAT1 transgenic rice started heading at 44 days after stopping watering.

The second experiment was performed in Ningxia province; the same twelve OsACOAT1 transgenic lines were tested. When 10% of the main stem panicles reached panicle initiation stage II, watering was stopped. The soil volumetric water content decreased from 45% to 10% during panicle heading (FIG. 10). The rainfall resulted in variation for the soil volumetric water content during drought stress. 16 days later, the main stem panicles reached panicle initiation stage IV-V, the tiller panicles reached panicle initiation stage III-IV, and the rice plants showed leaf rolling phenotype. One line DP1121.06 showed drought tolerance phenotype during drought stress, and two lines DP1121.01 and DP1121.04 showed better seed setting phenotype at the maturation stage.

As shown in Table 33, OsACOAT1 transgenic rice exhibited significantly greater grain yield per plant than DP0158 control, but lower grain yield per plants than ZH11-TC control at the construct level. Five lines had significantly greater grain yields per plant than DP0158 control, and one line had significantly greater grain yield per plant than ZH11-TC control.

These results demonstrate that OsACOAT1 rice plant is tolerance to drought, and over-expression of OsACOAT1 increases the grain yield per plant after drought stress at flowering and heading stage.

8) Field DRT Validation Results of OsDN-DTP7 (DP1176) Transgenic Rice

Figure 11:
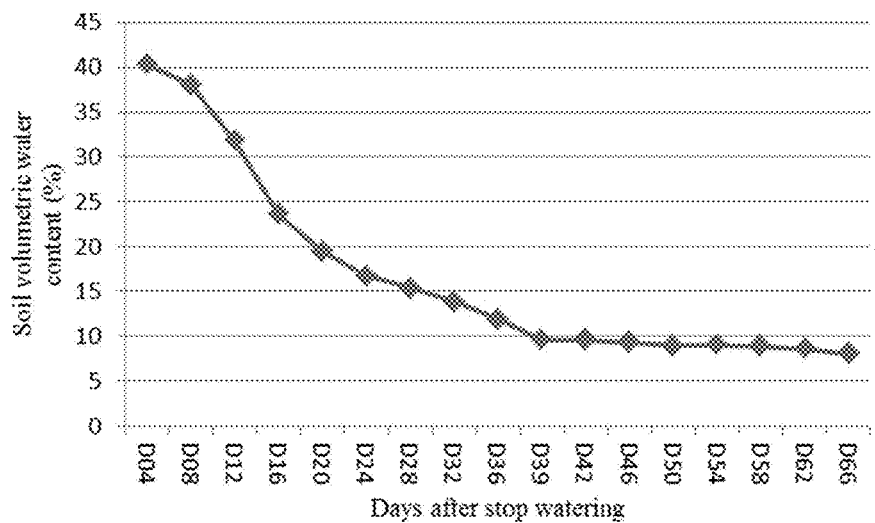
FIG. 11 shows changes of soil volumetric water content at different developmental stage for drought testing OsDN-DTP7 transgenic rice in the Hainan experiment. The OsDN-DTP7 transgenic rice started heading at 35 days after stopping watering.

Twelve OsDN-DTP7 transgenic lines were tested in Hainan Province in the first experiment. Watering was stopped from initiation stage II of main stem panicles to seed maturity to produce heavier drought stress. The soil volumetric water content decreased from 40% to 7% during heading and maturation stage (FIG. 11). 19 days after stopping watering, the main stem panicles were at panicle initiation VIII stage, the tiller panicles were at panicle initiation V-VI stage, and some rice plants exhibited phenotypes such as leaf rolling. The transgenic rice plants DP1176.02, DP1176.04 and DP1176.10 exhibited drought tolerance phenotypes such as greener leaf and less leaf rolling degree. At the end of the planting season, the transgenic rice plants DP1176.02, DP1176.05, DP1176.06 and DP1176.08 exhibited good seed setting rate.

The grain yield per plant is shown in Table 34, the OsDN-DTP7 transgenic rice plants showed greater grain yield per plant than ZH11-TC plants and significantly greater grain yield per plant than DP0158 plants at the construct level. Five OsDN-DTP7 transgenic rice lines showed significantly greater grain yields per plant than ZH11-TC and six transgenic lines showed significantly greater grain yields per plant than DP0158 plants at the line level. These results demonstrate that OsDN-DTP7 rice plant had greater grain yield per plant than control after drought stress.

TABLE 33

Grain yield analysis of OsACOAT1 transgenic rice plants under field drought conditions (2$^{nd}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP1121 (construct) | 468 | 285 | 4.39 | −0.76 | 0.313 | | 1.37 | | Y |
| ZH11-TC | 40 | 24 | 5.15 | | | | | | |
| DP0158 | 41 | 21 | 3.02 | | | | | | |
| DP1121.01 | 40 | 24 | 6.54 | 1.39 | 0.103 | | 3.52 | 0.000 | Y |
| DP1121.02 | 39 | 24 | 3.67 | −1.48 | 0.081 | | 0.65 | 0.445 | |
| DP1121.03 | 41 | 24 | 4.32 | −0.83 | 0.329 | | 1.30 | 0.126 | |
| DP1121.04 | 39 | 24 | 6.84 | 1.69 | 0.047 | Y | 3.82 | 0.000 | Y |
| DP1121.05 | 40 | 23 | 2.54 | −2.62 | 0.002 | | −0.48 | 0.571 | |
| DP1121.06 | 38 | 24 | 5.69 | 0.54 | 0.527 | | 2.67 | 0.002 | Y |
| DP1121.07 | 38 | 24 | 3.39 | −1.76 | 0.039 | | 0.37 | 0.667 | |
| DP1121.08 | 41 | 24 | 4.58 | −0.57 | 0.506 | | 1.56 | 0.067 | Y |
| DP1121.09 | 39 | 24 | 3.68 | −1.47 | 0.084 | | 0.66 | 0.442 | |
| DP1121.10 | 39 | 24 | 3.90 | −1.25 | 0.142 | | 0.88 | 0.306 | |
| DP1121.11 | 34 | 22 | 4.54 | −0.61 | 0.474 | | 1.52 | 0.076 | Y |
| DP1121.12 | 40 | 24 | 3.04 | −2.11 | 0.013 | | 0.02 | 0.980 | |

TABLE 34

Grain yield analysis of OsDN-DTP7 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1176 (construct) | 472 | 287 | 6.45 | 0.33 | 0.713 | | 1.62 | 0.071 | Y |
| ZH11-TC | 39 | 23 | 6.12 | | | | | | |
| DP0158 | 37 | 23 | 4.83 | | | | | | |
| DP1176.01 | 40 | 24 | 5.65 | −0.48 | 0.628 | | 0.82 | 0.405 | |
| DP1176.02 | 40 | 24 | 8.04 | 1.92 | 0.049 | Y | 3.21 | 0.001 | Y |
| DP1176.03 | 40 | 24 | 5.29 | −0.83 | 0.383 | | 0.46 | 0.637 | |
| DP1176.04 | 39 | 24 | 2.94 | −3.18 | 0.001 | | −1.89 | 0.054 | |
| DP1176.05 | 38 | 23 | 8.28 | 2.16 | 0.027 | Y | 3.45 | 0.000 | Y |
| DP1176.06 | 39 | 24 | 8.05 | 1.93 | 0.048 | Y | 3.22 | 0.001 | Y |
| DP1176.07 | 39 | 24 | 7.41 | 1.29 | 0.187 | | 2.58 | 0.008 | Y |
| DP1176.08 | 40 | 25 | 9.14 | 3.02 | 0.002 | Y | 4.31 | 0.000 | Y |
| DP1176.09 | 40 | 24 | 5.82 | −0.30 | 0.755 | | 0.99 | 0.311 | |
| DP1176.10 | 39 | 24 | 3.12 | −3.00 | 0.002 | | −1.71 | 0.083 | |
| DP1176.11 | 39 | 24 | 5.75 | −0.37 | 0.702 | | 0.92 | 0.347 | |
| DP1176.12 | 39 | 23 | 7.90 | 1.78 | 0.062 | Y | 3.07 | 0.001 | Y |

Figure 12:
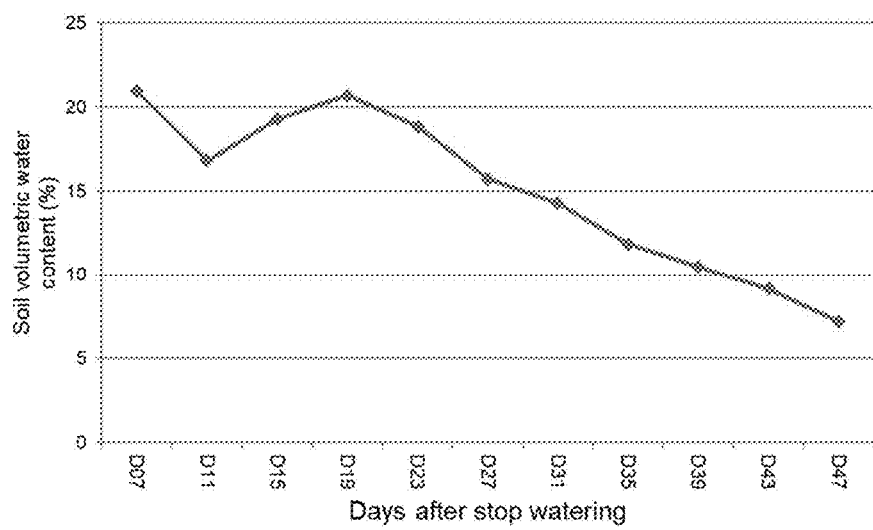
FIG. 12 shows changes of soil volumetric water content at different developmental stage for drought testing OsDN-DTP7 transgenic rice in the second experiment. The OsDN-DTP7 transgenic rice started heading at 26 days after stopping watering.

The second experiment was performed in Hainan province; the same twelve OsDN-DTP7 transgenic lines were tested. Watering was stopped when the main stem panicles reached initiation stage V-VI and the tiller panicles reached panicle initiation stage II-III. 52 days after stopping watering, the main stem panicles reached milk mature stage, and the rice plants started to show drought stress phenotype. The soil volumetric water content decreased from 22% to 7% during heading and maturation stage (FIG. 12). At the end of the planting season, the transgenic rice plants DP1176.02 and DP1176.08 exhibited good seed setting phenotype.

The grain yield per plant is shown in Table 35, the OsDN-DTP7 transgenic rice plants showed significantly greater grain yield per plant than ZH11-TC plants and greater grain yield per plant than DP0158 plants at the construct level. Five OsDN-DTP7 transgenic rice lines showed significantly greater grain yields per plant than ZH11-TC and four transgenic lines showed significantly greater grain yields per plant than DP0158 plants at the line level. These results demonstrate that OsDN-DTP7 rice plant had greater grain yield per plant than control after drought stress.

TABLE 35

Grain yield analysis of OsDN-DTP7 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1176 (construct) | 479 | 288 | 5.77 | 1.92 | 0.053 | Y | 0.93 | 0.348 | |
| ZH11-TC | 39 | 24 | 3.85 | | | | | | |
| DP0158 | 40 | 24 | 4.84 | | | | | | |
| DP1176.01 | 40 | 24 | 3.84 | −0.01 | 0.990 | | −1.00 | 0.339 | |
| DP1176.02 | 40 | 24 | 9.46 | 5.61 | 0.000 | Y | 4.63 | 0.000 | Y |
| DP1176.03 | 40 | 24 | 4.85 | 1.00 | 0.338 | | 0.02 | 0.988 | |
| DP1176.04 | 40 | 24 | 2.46 | −1.39 | 0.193 | | −2.37 | 0.026 | |
| DP1176.05 | 40 | 24 | 9.18 | 5.33 | 0.000 | Y | 4.34 | 0.000 | Y |
| DP1176.06 | 40 | 24 | 9.01 | 5.16 | 0.000 | Y | 4.18 | 0.000 | Y |
| DP1176.07 | 39 | 24 | 6.35 | 2.50 | 0.018 | Y | 1.51 | 0.153 | |
| DP1176.08 | 40 | 24 | 10.04 | 6.18 | 0.000 | Y | 5.20 | 0.000 | Y |
| DP1176.09 | 40 | 24 | 3.51 | −0.34 | 0.747 | | −1.33 | 0.210 | |
| DP1176.10 | 40 | 24 | 1.80 | −2.05 | 0.054 | | −3.04 | 0.004 | |
| DP1176.11 | 40 | 24 | 4.35 | 0.50 | 0.636 | | −0.49 | 0.641 | |
| DP1176.12 | 40 | 24 | 4.39 | 0.54 | 0.607 | | −0.45 | 0.669 | |

Example 7

Laboratory Paraquat Assays of Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant transgenic rice plants was tested.

Paraquat Assay Methods:

Transgenic rice plants from ten transgenic lines were tested by paraquat assay. Tissue-cultured Zhonghua 11 plants (ZH11-TC) and empty vector transgenic plants (DP0158) were used as controls. $T_2$ transgenic seeds were sterilized and germinated as described in Example 4, and this assay was carried out in growth room with temperature at 28~30° C. and humidity 30%. The germinated seeds were placed in a tube with a hole at the bottom, and water cultured at 30° C. for 5 days till one-leaf and one-terminal bud stage. Uniform seedlings about 3.5~4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 μM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS® PROC GLIMMIX".

Paraquat Assay Results:

1) Paraquat Validation Results of OsICDH1 (DP0854) Transgenic Rice

In the first experiment, after paraquat solution treated for seven days, 398 of the 600 OsICDH1 transgenic seedlings (66%) kept green and showed tolerant phenotype, while 72 of the 180 (40%) seedlings from ZH11-TC showed tolerant phenotype, and 105 of the 180 (58%) DP0158 seedlings showed tolerant phenotype. The tolerance rate of all screened OsICDH1 transgenic seedlings was significantly greater than ZH11-TC and DP0158 controls at the construct level.

Further analysis at transgenic line level indicates that nine OsICDH1 transgenic lines had significantly greater tolerance rates than ZH11-TC control and three lines had significantly greater tolerance rates than DP0158 control (Table 36). These results demonstrate that OsICDH1 transgenic rice plants had enhanced paraquat tolerance compared to both controls of ZH11-TC and DP0158 rice plants at construct and transgenic line level at seedling stages. OsICDH1 functions in enhancing paraquat tolerance or antioxidative ability of transgenic plants.

TABLE 36

Paraquat tolerance assay of OsICDH1 transgenic rice plants (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0854 (Construct) | 398 | 600 | 66 | 0.0000 | Y | 0.0421 | Y |
| ZH11-TC | 72 | 180 | 40 | | | | |
| DP0158 | 105 | 180 | 58 | | | | |
| DP0854.01 | 47 | 60 | 78 | 0.0000 | Y | 0.0082 | Y |
| DP0854.02 | 44 | 60 | 73 | 0.0000 | Y | 0.0441 | Y |
| DP0854.03 | 42 | 60 | 70 | 0.0002 | Y | 0.1150 | |
| DP0854.04 | 43 | 60 | 72 | 0.0001 | Y | 0.0725 | |
| DP0854.07 | 35 | 60 | 58 | 0.0170 | Y | 1.0000 | |
| DP0854.08 | 36 | 60 | 60 | 0.0097 | Y | 0.8211 | |
| DP0854.09 | 45 | 60 | 75 | 0.0000 | Y | 0.0260 | Y |
| DP0854.10 | 37 | 60 | 62 | 0.0054 | Y | 0.6508 | |
| DP0854.11 | 32 | 60 | 53 | 0.0773 | | 0.5008 | |
| DP0854.12 | 37 | 60 | 62 | 0.0054 | Y | 0.6508 | |

In the second experiment, ten same OsICDH1 transgenic lines were tested. Seven days later, 424 of the 600 OsICDH1 transgenic seedlings (71%) kept green and showed tolerant phenotype, while 104 of the 180 (58%) seedlings from ZH11-TC showed tolerant phenotype, and 114 of the 180 (63%) DP0158 seedlings showed tolerant phenotype. The tolerance rate of all screened OsICDH1 transgenic seedlings was significantly greater than ZH11-TC control at the construct level.

Further analysis at transgenic line level indicates that four OsICDH1 transgenic lines had significantly greater tolerance rates than ZH11-TC control and one line had significantly greater tolerance rates than DP0158 control (Table 37). These results further demonstrate that OsICDH1 functions in enhancing paraquat tolerance or antioxidative ability of transgenic plants.

TABLE 37

Paraquat tolerance assay of OsICDH1 transgenic rice plants (2$^{nd}$ experiment)

| Line ID | Number of tolerant seedlings | Number of total seedlings | Tolerant rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0854 (Construct) | 424 | 600 | 71 | 0.0015 | Y | 0.0563 | |
| ZH11-TC | 104 | 180 | 58 | | | | |
| DP0158 | 114 | 180 | 63 | | | | |
| DP0854.01 | 43 | 60 | 72 | 0.0612 | | 0.2438 | |
| DP0854.02 | 45 | 60 | 75 | 0.0214 | Y | 0.1037 | |
| DP0854.03 | 33 | 60 | 55 | 0.7066 | | 0.2544 | |
| DP0854.04 | 44 | 60 | 73 | 0.0368 | Y | 0.1624 | |
| DP0854.07 | 47 | 60 | 78 | 0.0066 | Y | 0.0377 | Y |
| DP0854.08 | 43 | 60 | 72 | 0.0612 | | 0.2438 | |
| DP0854.09 | 45 | 60 | 75 | 0.0214 | Y | 0.1037 | |
| DP0854.10 | 40 | 60 | 67 | 0.2273 | | 0.6415 | |
| DP0854.11 | 43 | 60 | 72 | 0.0612 | | 0.2438 | |
| DP0854.12 | 41 | 60 | 68 | 0.1521 | | 0.4835 | |

2) Paraquat Validation Results of OsMtN3L (DP0902) Transgenic Rice

In the first experiment, after paraquat solution treated for seven days, 219 of the 600 OsMtN3L transgenic seedlings (37%) kept green and showed tolerant phenotype, while 48 of the 168 (29%) seedlings from ZH11-TC showed tolerant phenotype, and 58 of the 180 (32%) DP0158 seedlings showed tolerant phenotype. The tolerance rate of all screened OsMtN3L transgenic seedlings was greater than ZH11-TC and DP0158 controls at the construct level.

Further analysis at transgenic line level indicates that four OsMtN3L transgenic lines had significantly greater tolerance rates compared with ZH11-TC and DP0158 controls (Table 38). These results demonstrate that OsMtN3L transgenic rice plants had enhanced paraquat tolerance compared to both controls of ZH11-TC and DP0158 rice plants at construct and transgenic line level at seedling stages. OsMtN3L functions in enhancing paraquat tolerance or antioxidative ability of transgenic plants.

In the second experiment, the same ten OsMtN3L transgenic lines were tested. Seven days later, 465 of the 600 OsMtN3L transgenic seedlings (78%) kept green and showed tolerant phenotype, while 122 of the 180 (68%) seedlings from ZH11-TC showed tolerant phenotype, and 117 of the 180 (65%) DP0158 seedlings showed tolerant phenotype. The tolerance rate of all screened OsMtN3L transgenic seedlings was significantly greater than ZH11-TC and DP0158 controls at the construct level.

Further analysis at transgenic line level indicates that all the ten OsMtN3L transgenic lines had greater tolerance rates compared with ZH11-TC and DP0158 controls (Table 39). These results demonstrate that OsMtN3L transgenic rice plants had enhanced paraquat tolerance compared to both controls of ZH11-TC and DP0158 rice plants at construct and transgenic line level at seedling stages. OsMtN3L play a role in enhancing paraquat tolerance or antioxidative ability of transgenic plants.

TABLE 38

Paraquat tolerance assay of OsMtN3L transgenic rice plants (1$^{st}$ experiment)

| Line ID | Number of tolerant seedlings | Number of total seedlings | Tolerant rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0902 (construct) | 219 | 600 | 37 | 0.1702 | | 0.5523 | |
| ZH11-TC | 48 | 168 | 29 | | | | |
| DP0158 | 58 | 180 | 32 | | | | |
| DP0902.01 | 8 | 60 | 13 | 0.0225 | | 0.0077 | |
| DP0902.02 | 15 | 60 | 25 | 0.5679 | | 0.2947 | |
| DP0902.03 | 16 | 60 | 27 | 0.7464 | | 0.4204 | |
| DP0902.04 | 10 | 60 | 17 | 0.0706 | | 0.0258 | |
| DP0902.05 | 22 | 60 | 37 | 0.2638 | | 0.5267 | |
| DP0902.06 | 37 | 60 | 62 | 0.0000 | Y | 0.0002 | Y |
| DP0902.07 | 38 | 60 | 63 | 0.0000 | Y | 0.0000 | Y |
| DP0902.08 | 15 | 60 | 25 | 0.5679 | | 0.2947 | |
| DP0902.09 | 28 | 60 | 47 | 0.0152 | Y | 0.0476 | Y |
| DP0902.10 | 30 | 60 | 50 | 0.0047 | Y | 0.0164 | Y |

TABLE 39

Paraquat tolerance assay of OsMtN3L transgenic rice plants (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0902 (Construct) | 465 | 600 | 78 | 0.0094 | Y | 0.0012 | Y |
| ZH11-TC | 122 | 180 | 68 | | | | |
| DP0158 | 117 | 180 | 65 | | | | |
| DP0902.01 | 47 | 60 | 78 | 0.1284 | | 0.0616 | |
| DP0902.02 | 47 | 60 | 78 | 0.1284 | | 0.0616 | |
| DP0902.03 | 50 | 60 | 83 | 0.0266 | Y | 0.0114 | Y |
| DP0902.04 | 46 | 60 | 77 | 0.1999 | | 0.1010 | |
| DP0902.05 | 47 | 60 | 78 | 0.1284 | | 0.0616 | |
| DP0902.06 | 46 | 60 | 77 | 0.1999 | | 0.1010 | |
| DP0902.07 | 48 | 60 | 80 | 0.0789 | | 0.0362 | Y |
| DP0902.08 | 43 | 60 | 72 | 0.5758 | | 0.3473 | |
| DP0902.09 | 44 | 60 | 73 | 0.4234 | | 0.2402 | |
| DP0902.10 | 47 | 60 | 78 | 0.1284 | | 0.0616 | |

3) Paraquat Validation Results of OsDN-DTP6 (DP0935) Transgenic Rice

In the first experiment, 321 of the 600 transgenic seedlings (54%) kept green and showed tolerant phenotype after treated with 0.8 μM paraquat solutions for 7 days, while 68 of the 180 (38%) seedlings from ZH11-TC showed tolerant phenotype and 80 of the 180 (44%) seedlings from DP0158 showed tolerant phenotype. The tolerance rate of OsDN-DTP6 transgenic seedlings was significantly higher than ZH11-TC and DP0158 controls. Analysis at transgenic line level is displayed in Table 40. Seven OsDN-DTP6 transgenic lines had significantly higher tolerance rates than either ZH11-TC or DP0158 controls, and the tolerance rates of four lines were more than 60%. These results show that over-expression OsDN-DTP6 gene increased the paraquat tolerance or antioxidative ability of the transgenic plants.

In the second experiment, the same ten OsDN-DTP6 transgenic lines were tested. 449 of the 600 transgenic seedlings (75%) kept green and showed tolerant phenotype after treated with 0.8 μM paraquat solutions for 7 days, while 115 of the 180 (64%) seedlings from ZH11-TC showed tolerant phenotype and 104 of the 180 (58%) seedlings from DP0158 showed tolerant phenotype. The tolerance rate of OsDN-DTP6 transgenic seedlings was significantly higher than ZH11-TC and DP0158 controls.

Further analysis at transgenic line level is displayed in Table 41. Four OsDN-DTP6 transgenic lines had significantly higher tolerance rates than either ZH11-TC or DP0158 controls, and the tolerance rates of nine lines were more than 70%. These results show that over-expression OsDN-DTP6 gene increased the paraquat tolerance. OsDN-DTP6 plays a role in enhancing paraquat tolerance or antioxidative ability of the transgenic plants.

TABLE 40

Paraquat tolerance assay of OsDN-DTP6 transgenic rice plants (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0935 (construct) | 321 | 600 | 54 | 0.0004 | Y | 0.0312 | Y |
| ZH11-TC | 68 | 180 | 38 | | | | |
| DP0158 | 80 | 180 | 44 | | | | |
| DP0935.01 | 42 | 60 | 70 | 0.0000 | Y | 0.0012 | Y |
| DP0935.03 | 47 | 60 | 78 | 0.0000 | Y | 0.0000 | Y |
| DP0935.04 | 35 | 60 | 58 | 0.0072 | Y | 0.0657 | |
| DP0935.05 | 31 | 60 | 52 | 0.0622 | | 0.3312 | |
| DP0935.06 | 21 | 60 | 35 | 0.6976 | | 0.2010 | |
| DP0935.07 | 39 | 60 | 65 | 0.0006 | Y | 0.0078 | Y |
| DP0935.09 | 37 | 60 | 62 | 0.0021 | Y | 0.0240 | Y |
| DP0935.13 | 18 | 60 | 30 | 0.2776 | | 0.0528 | |
| DP0935.14 | 29 | 60 | 48 | 0.1519 | | 0.5993 | |
| DP0935.15 | 22 | 60 | 37 | 0.8774 | | 0.2922 | |

TABLE 41

Paraquat tolerance assay of OsDN-DTP6 transgenic rice plants (2$^{nd}$ experiment)

| Line ID | Number of tolerant seedlings | Number of total seedlings | Tolerant rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0935 (Construct) | 449 | 600 | 75 | 0.0039 | Y | 0.0000 | Y |
| ZH11-TC | 115 | 180 | 64 | | | | |
| DP0158 | 104 | 180 | 58 | | | | |
| DP0935.01 | 43 | 60 | 72 | 0.2767 | | 0.0623 | |
| DP0935.03 | 43 | 60 | 72 | 0.2767 | | 0.0623 | |
| DP0935.04 | 37 | 60 | 62 | 0.7581 | | 0.5982 | |
| DP0935.05 | 43 | 60 | 72 | 0.2767 | | 0.0623 | |
| DP0935.06 | 49 | 60 | 82 | 0.0146 | Y | 0.0020 | Y |
| DP0935.07 | 47 | 60 | 78 | 0.0451 | Y | 0.0069 | Y |
| DP0935.09 | 47 | 60 | 78 | 0.0451 | Y | 0.0069 | Y |
| DP0935.13 | 51 | 60 | 85 | 0.0043 | Y | 0.0006 | Y |
| DP0935.14 | 43 | 60 | 72 | 0.2767 | | 0.0623 | |
| DP0935.15 | 46 | 60 | 77 | 0.0753 | | 0.0124 | Y |

4) Paraquat Validation Results of OsANKL1 (DP0960) Transgenic Rice

In the first experiment, 348 of the 600 OsANKL1 transgenic seedlings (58%) kept green and showed tolerant phenotype after treated with paraquat solution, whereas only 75 of the 180 (42%) ZH11-TC seedlings, and 94 of the 180 (52%) DP0158 seedlings showed tolerant phenotype. The tolerance rate of OsANKL1 transgenic plants was significantly higher than that of the ZH11-TC control and higher than that of DP0158 control at the construct level. The analysis at transgenic line level is displayed in Table 42. Seven lines had greater tolerance rates than either ZH11-TC or DP0158 seedlings, which further demonstrates that OsANKL1 transgenic rice plants had enhanced paraquat tolerance at construct and transgenic line level at seedling stages. Over-expression of OsANKL1 gene improved the paraquat tolerance of the transgenic plants.

In the second experiment, 418 of the 600 OsANKL1 transgenic seedlings (70%) kept green and showed tolerant phenotype after treated with paraquat solution, whereas only 114 of the 180 (63%) ZH11-TC seedlings, and 114 of the 180 (63%) DP0158 seedlings showed tolerant phenotype. The tolerance rate of OsANKL1 transgenic plants was higher than that of the ZH11-TC control and DP0158 control at the construct level. The analysis at transgenic line level is displayed in Table 43. Seven lines had greater tolerance rates than either ZH11-TC or DP0158 seedlings, these results further demonstrates that OsANKL1 transgenic rice plants had enhanced paraquat tolerance at construct and transgenic line level at seedling stages. Over-expression of OsANKL1 gene improved the paraquat tolerance of the transgenic plants.

TABLE 42

Paraquat tolerance assay of OsANKL1 transgenic rice plants (1$^{st}$ experiment)

| Line ID | Number of tolerant seedlings | Number of total seedlings | Tolerant rate (%) | CK = ZH11-TC P value | CK = ZH11-TC P ≤ 0.05 | CK = DP0158 P value | CK = DP0158 P ≤ 0.05 |
|---|---|---|---|---|---|---|---|
| DP0960 (construct) | 348 | 600 | 58 | 0.0002 | Y | 0.1470 | |
| ZH11-TC | 75 | 180 | 42 | | | | |
| DP0158 | 94 | 180 | 52 | | | | |
| DP0960.01 | 18 | 60 | 30 | 0.1152 | | 0.0046 | |
| DP0960.02 | 20 | 60 | 33 | 0.2588 | | 0.0148 | |
| DP0960.03 | 30 | 60 | 50 | 0.2650 | | 0.7670 | |
| DP0960.04 | 31 | 60 | 52 | 0.1829 | | 0.9413 | |
| DP0960.05 | 37 | 60 | 62 | 0.0100 | Y | 0.2091 | |
| DP0960.07 | 45 | 60 | 75 | 0.0000 | Y | 0.0035 | Y |
| DP0960.09 | 39 | 60 | 65 | 0.0030 | Y | 0.0912 | |
| DP0960.10 | 41 | 60 | 68 | 0.0009 | Y | 0.0347 | Y |
| DP0960.11 | 43 | 60 | 72 | 0.0002 | Y | 0.0117 | Y |
| DP0960.12 | 44 | 60 | 73 | 0.0001 | Y | 0.0065 | Y |

TABLE 43

Paraquat tolerance assay of OsANKL1 transgenic rice plants (2nd experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0960 (Construct) | 418 | 600 | 70 | 0.0830 | | 0.0832 | |
| ZH11-TC | 114 | 180 | 63 | | | | |
| DP0158 | 114 | 180 | 63 | | | | |
| DP0960.01 | 41 | 60 | 68 | 0.4858 | | 0.4857 | |
| DP0960.02 | 34 | 60 | 57 | 0.3624 | | 0.3624 | |
| DP0960.03 | 45 | 60 | 75 | 0.1051 | | 0.1051 | |
| DP0960.04 | 48 | 60 | 80 | 0.0221 | Y | 0.0220 | Y |
| DP0960.05 | 46 | 60 | 77 | 0.0647 | | 0.0647 | |
| DP0960.07 | 45 | 60 | 75 | 0.1051 | | 0.1051 | |
| DP0960.09 | 36 | 60 | 60 | 0.6465 | | 0.6466 | |
| DP0960.10 | 39 | 60 | 65 | 0.8163 | | 0.8162 | |
| DP0960.11 | 36 | 60 | 60 | 0.6465 | | 0.6466 | |
| DP0960.12 | 48 | 60 | 80 | 0.0221 | Y | 0.0221 | Y |

5) Paraquat Validation Results of OsMBD2 (DP0988) Transgenic Rice

In the first experiment, 295 of the 600 OsMBD2 transgenic seedlings (49%) kept green and showed tolerant phenotype after treated with paraquat solutions, whereas 99 of the 180 (55%) ZH11-TC seedlings showed tolerant phenotype, and 90 of the 180 (50%) DP0158 seedlings showed tolerant phenotype. The tolerance rate of OsMBD2 transgenic seedlings was low than that of the ZH11-TC and DP0158 controls at the construct level. Table 44 illustrates the analysis at line level. One OsMBD2 transgenic line showed significantly greater tolerance rate than ZH11-TC control and two transgenic lines showed significantly greater tolerance rates than DP0158 control. The OsMBD2 transgenic lines didn't show better paraquat tolerance.

In the second experiment, 263 of the 600 OsMBD2 transgenic seedlings (44%) kept green and showed tolerant phenotype after treated with paraquat solutions, whereas 80 of the 180 (44%) ZH11-TC seedlings showed tolerant phenotype, and 88 of the 180 (49%) DP0158 seedlings showed tolerant phenotype. The tolerance rate of OsMBD2 transgenic seedlings was like that of the ZH11-TC and DP0158 controls at the construct level. Analysis at transgenic line level shows that eight lines had lower tolerance rates than ZH11-TC or DP0158 controls (Table 45). Only two transgenic lines showed significantly tolerance rates than ZH11-TC control. These results also showed that OsMBD2 transgenic rice didn't exhibit better paraquat tolerance or antioxidative activity.

TABLE 44

Paraquat tolerance assay of OsMBD2 transgenic rice plants (1st experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0988 (construct) | 295 | 600 | 49 | 0.1833 | | 0.8587 | |
| ZH11-TC | 99 | 180 | 55 | | | | |
| DP0158 | 90 | 180 | 50 | | | | |
| DP0988.01 | 25 | 60 | 42 | 0.0785 | | 0.2661 | |
| DP0988.02 | 24 | 60 | 40 | 0.0489 | | 0.1833 | |
| DP0988.03 | 30 | 60 | 50 | 0.5024 | | 0.9999 | |
| DP0988.04 | 14 | 60 | 23 | 0.0001 | | 0.0008 | |
| DP0988.05 | 23 | 60 | 38 | 0.0295 | | 0.1218 | |
| DP0988.06 | 28 | 60 | 47 | 0.2660 | | 0.6546 | |
| DP0988.07 | 39 | 60 | 65 | 0.1794 | | 0.0486 | Y |
| DP0988.12 | 34 | 60 | 57 | 0.8213 | | 0.3727 | |
| DP0988.14 | 34 | 60 | 57 | 0.6522 | | 0.2663 | |
| DP0988.15 | 44 | 60 | 73 | 0.0157 | Y | 0.0029 | Y |

TABLE 45

Paraquat tolerance assay of OsMBD2 transgenic rice plants (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP0988 (construct) | 263 | 600 | 44 | 0.8423 | | 0.2195 | |
| ZH11-TC | 80 | 180 | 44 | | | | |
| DP0158 | 88 | 180 | 49 | | | | |
| DP0988.01 | 25 | 60 | 42 | 0.7085 | | 0.3361 | |
| DP0988.02 | 18 | 60 | 30 | 0.0549 | | 0.0143 | |
| DP0988.03 | 24 | 60 | 40 | 0.5497 | | 0.2375 | |
| DP0988.04 | 24 | 60 | 40 | 0.5497 | | 0.2375 | |
| DP0988.05 | 18 | 60 | 30 | 0.0549 | | 0.0143 | |
| DP0988.06 | 42 | 60 | 70 | 0.0013 | Y | 0.0068 | Y |
| DP0988.07 | 28 | 60 | 47 | 0.7655 | | 0.7664 | |
| DP0988.08 | 38 | 60 | 63 | 0.0147 | Y | 0.0584 | |
| DP0988.09 | 29 | 60 | 48 | 0.6023 | | 0.9408 | |
| DP0988.10 | 17 | 60 | 28 | 0.0330 | | 0.0080 | |

6) Paraquat Validation Results of OsTP1 (DP1082) Transgenic Rice

In the first experiment, after cultured in paraquat solutions for 7 days, 371 of the 600 OsTP1 transgenic seedlings (62%) kept green and showed tolerant phenotype, 103 of the 180 (57%) ZH11-TC seedlings showed tolerant phenotype, and 108 of the 180 (60%) DP0158 seedlings showed tolerant phenotype. The tolerance rate of OsTP1 transgenic seedlings was higher than that of the ZH11-TC and DP0158 controls at the construct level. Analysis at the transgenic line level is shown in Table 46. Five OsTP1 transgenic lines showed higher tolerance rates than either ZH11-TC or DP0158 control. These results demonstrate that OsTP1 over-expressed transgenic rice plants may enhance paraquat tolerance at construct and transgenic line level at seedling stages.

In the second experiment, the same ten OsTP1 transgenic lines were tested. After cultured in paraquat solutions for 7 days, 465 of the 588 OsTP1 transgenic seedlings (79%) kept green and showed tolerant phenotype, 135 of the 192 (70%) ZH11-TC seedlings showed tolerant phenotype, and 119 of the 180 (66%) DP0158 seedlings showed tolerant phenotype. The tolerance rate of OsTP1 transgenic seedlings was significantly higher than that of the ZH11-TC and DP0158 controls at the construct level.

Further analysis at the transgenic line level is shown in Table 47. Four OsTP1 transgenic lines showed significantly higher tolerance rates than ZH11-TC control and six lines showed significantly higher tolerance rates than DP0158 control. These results demonstrate that OsTP1 over-expressed transgenic rice plants enhance paraquat tolerance at construct and transgenic line level at seedling stages. OsTP1 functions in enhancing paraquat tolerance or the antioxidative activity.

TABLE 46

Paraquat tolerance assay of OsTP1 transgenic rice plants (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP1082 (construct) | 371 | 600 | 62 | 0.2219 | | 0.5707 | |
| ZH11-TC | 103 | 180 | 57 | | | | |
| DP0158 | 108 | 180 | 60 | | | | |
| DP1082.01 | 30 | 60 | 50 | 0.3348 | | 0.1813 | |
| DP1082.03 | 35 | 60 | 58 | 0.8802 | | 0.8210 | |
| DP1082.04 | 36 | 60 | 60 | 0.7069 | | 0.9996 | |
| DP1082.05 | 42 | 60 | 70 | 0.0865 | | 0.1725 | |
| DP1082.06 | 47 | 60 | 78 | 0.0057 | Y | 0.0141 | Y |
| DP1082.08 | 38 | 60 | 63 | 0.4087 | | 0.6484 | |
| DP1082.09 | 28 | 60 | 47 | 0.1617 | | 0.0776 | |
| DP1082.10 | 43 | 60 | 72 | 0.0534 | | 0.1122 | |
| DP1082.11 | 41 | 60 | 68 | 0.1349 | | 0.2549 | |
| DP1082.12 | 31 | 60 | 52 | 0.4569 | | 0.2633 | |

TABLE 47

Paraquat tolerance assay of OsTP1 transgenic rice plants (2<sup>nd</sup> experiment)

| Line ID | Number tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP1082 (Construct) | 465 | 588 | 79 | 0.0085 |   | 0.0004 | Y |
| ZH11-TC | 135 | 192 | 70 |   |   |   |   |
| DP0158 | 119 | 180 | 66 |   |   |   |   |
| DP1082.01 | 30 | 48 | 63 | 0.3171 |   | 0.6606 |   |
| DP1082.03 | 49 | 60 | 82 | 0.0905 |   | 0.0284 | Y |
| DP1082.04 | 51 | 60 | 85 | 0.0301 | Y | 0.0087 | Y |
| DP1082.05 | 42 | 60 | 70 | 0.9692 |   | 0.5789 |   |
| DP1082.06 | 53 | 60 | 88 | 0.0090 | Y | 0.0025 | Y |
| DP1082.08 | 47 | 60 | 78 | 0.2296 |   | 0.0827 |   |
| DP1082.09 | 52 | 60 | 87 | 0.0166 | Y | 0.0047 | Y |
| DP1082.10 | 49 | 60 | 82 | 0.0905 |   | 0.0284 | Y |
| DP1082.11 | 41 | 60 | 68 | 0.7771 |   | 0.7508 |   |
| DP1082.12 | 51 | 60 | 85 | 0.0301 | Y | 0.0087 | Y |

7) Paraquat Validation Results of OsACOAT1 (DP1121) Transgenic Rice

In the first experiment, after cultured in paraquat solutions for 7 days, 441 of the 600 OsACOAT1 over-expressed transgenic seedlings (74%) kept green and showed tolerant phenotype, while 113 of the 180 (63%) ZH11-TC seedlings showed tolerant phenotype, and 118 of the 180 (66%) DP0158 seedlings showed tolerant phenotype. The tolerance rate of OsACOAT1 transgenic seedlings was significantly higher than both of ZH11-TC and DP0158 controls at the construct level. Analysis at transgenic line level is shown in Table 36. Seven OsACOAT1 transgenic lines had higher tolerance rates than either ZH11-TC or DP0158 controls and three lines showed the significantly higher tolerance rates than either ZH11-TC or DP0158 controls (Table 48). These results demonstrate that OsACOAT1 over-expressed transgenic rice plants had enhanced paraquat tolerance at construct and transgenic line level at seedling stages.

In the second experiment, after cultured in paraquat solutions for 7 days, 453 of the 600 OsACOAT1 over-expressed transgenic seedlings (76%) kept green and showed tolerant phenotype, while 115 of the 180 (64%) ZH11-TC seedlings showed tolerant phenotype, and 112 of the 180 (62%) DP0158 seedlings showed tolerant phenotype. The tolerance rate of OsACOAT1 transgenic seedlings was significantly higher than both of ZH11-TC and DP0158 controls at the construct level. Analysis at transgenic line level is shown in Table 49. Seven OsACOAT1 transgenic lines had significantly higher tolerance rates than either ZH11-TC or DP0158 controls. These results demonstrate that OsACOAT1 over-expressed transgenic rice plants had enhanced paraquat tolerance at construct and transgenic line level at seedling stages. OsACOAT1 gene plays a role in the improvement of paraquat tolerance or antioxidative activity of transgenic plants.

TABLE 48

Paraquat tolerance assay of OsACOAT1 transgenic rice plants (1<sup>st</sup> experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP1121 (construct) | 441 | 600 | 74 | 0.0023 | Y | 0.0152 | Y |
| ZH11-TC | 113 | 180 | 63 |   |   |   |   |
| DP0158 | 118 | 180 | 66 |   |   |   |   |
| DP1121.01 | 50 | 60 | 83 | 0.0055 | Y | 0.0133 | Y |
| DP1121.02 | 40 | 60 | 67 | 0.5884 |   | 0.8752 |   |
| DP1121.03 | 52 | 60 | 87 | 0.0016 | Y | 0.0039 | Y |
| DP1121.04 | 55 | 60 | 92 | 0.0003 | Y | 0.0007 | Y |
| DP1121.05 | 42 | 60 | 70 | 0.3146 |   | 0.5286 |   |
| DP1121.06 | 37 | 60 | 62 | 0.8773 |   | 0.5861 |   |
| DP1121.07 | 44 | 60 | 73 | 0.1426 |   | 0.2698 |   |
| DP1121.08 | 38 | 60 | 63 | 0.9388 |   | 0.7549 |   |
| DP1121.09 | 44 | 60 | 73 | 0.1426 |   | 0.2698 |   |
| DP1121.10 | 39 | 60 | 65 | 0.7559 |   | 0.9393 |   |

TABLE 49

Paraquat tolerance assay of OsACOAT1 transgenic rice plants (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP1121 (Construct) | 453 | 600 | 76 | 0.0014 | Y | 0.0004 | Y |
| ZH11-TC | 115 | 180 | 64 | | | | |
| DP0158 | 112 | 180 | 62 | | | | |
| DP1121.01 | 47 | 60 | 78 | 0.0449 | Y | 0.0275 | Y |
| DP1121.02 | 50 | 60 | 83 | 0.0080 | Y | 0.0047 | Y |
| DP1121.03 | 47 | 60 | 78 | 0.0449 | Y | 0.0275 | Y |
| DP1121.04 | 52 | 60 | 87 | 0.0023 | Y | 0.0013 | Y |
| DP1121.05 | 49 | 60 | 82 | 0.0145 | Y | 0.0086 | Y |
| DP1121.06 | 36 | 60 | 60 | 0.5907 | | 0.7599 | |
| DP1121.07 | 36 | 60 | 60 | 0.5907 | | 0.7599 | |
| DP1121.08 | 49 | 60 | 82 | 0.0145 | Y | 0.0086 | Y |
| DP1121.09 | 38 | 60 | 63 | 0.9384 | | 0.8778 | |
| DP1121.10 | 49 | 60 | 82 | 0.0146 | Y | 0.0086 | Y |

8) Paraquat Validation Results of OsDN-DTP7 (DP1176) Transgenic Rice

In the first experiment, after cultured in paraquat solutions for 7 days, 447 of the 600 OsDN-DTP7 over-expressed transgenic seedlings (75%) kept green and showed tolerant phenotype, while only 113 of the 180 (63%) ZH11-TC seedlings showed tolerant phenotype, and 112 of the 180 (62%) DP0158 seedlings showed tolerant phenotype. The tolerance rate of OsDN-DTP7 transgenic seedlings was significantly higher than ZH11-TC and DP0158 controls at the construct level. Analysis at transgenic line level is shown in Table 50. Eight OsDN-DTP7 transgenic lines had higher tolerance rates than ZH11-TC control and nine transgenic lines had higher tolerance rates than DP0158 control. These results demonstrate that OsDN-DTP7 over-expressed transgenic rice plants had enhanced paraquat tolerance at construct and transgenic line level at seedling stages.

In the second experiment, after cultured in paraquat solutions for 7 days, 427 of the 600 OsDN-DTP7 over-expressed transgenic seedlings (71%) kept green and showed tolerant phenotype, while only 100 of the 180 (56%) ZH11-TC seedlings showed tolerant phenotype, and 116 of the 180 (64%) DP0158 seedlings showed tolerant phenotype. The tolerance rate of OsDN-DTP7 transgenic seedlings was significantly higher than ZH11-TC and higher than DP0158 control at the construct level. Analysis at transgenic line level is shown in Table 51. Nine OsDN-DTP7 transgenic lines had higher tolerance rates than ZH11-TC and DP0158 controls. These results demonstrate that OsDN-DTP7 over-expressed transgenic rice plants had enhanced paraquat tolerance at construct and transgenic line level at seedling stages. OsDN-DTP7 gene plays a role in the improvement of paraquat tolerance or antioxidative activity of transgenic plants.

TABLE 50

Paraquat tolerance assay of OsDN-DTP7 transgenic rice plants (1$^{st}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP1176 (construct) | 447 | 600 | 75 | 0.0016 | Y | 0.0010 | Y |
| ZH11-TC | 113 | 180 | 63 | | | | |
| DP0158 | 112 | 180 | 62 | | | | |
| DP1176.01 | 48 | 60 | 80 | 0.0186 | Y | 0.0157 | Y |
| DP1176.02 | 46 | 60 | 77 | 0.0555 | | 0.0475 | Y |
| DP1176.03 | 46 | 60 | 77 | 0.0555 | | 0.0475 | Y |
| DP1176.04 | 51 | 60 | 85 | 0.0030 | Y | 0.0025 | Y |
| DP1176.05 | 49 | 60 | 82 | 0.0103 | Y | 0.0087 | Y |
| DP1176.06 | 42 | 60 | 70 | 0.3159 | | 0.2818 | |
| DP1176.07 | 48 | 60 | 80 | 0.0186 | Y | 0.0157 | Y |
| DP1176.08 | 49 | 60 | 82 | 0.0103 | Y | 0.0087 | Y |
| DP1176.09 | 30 | 60 | 50 | 0.0870 | | 0.1017 | |
| DP1176.10 | 38 | 60 | 63 | 0.9387 | | 0.8781 | |

TABLE 51

Paraquat tolerance assay of OsDN-DTP7 transgenic rice plants (2$^{nd}$ experiment)

| Line ID | Number of tolerant seedlings | Number of total seedlings | Tolerant rate (%) | CK = ZH11-TC P value | P ≤ 0.05 | CK = DP0158 P value | P ≤ 0.05 |
|---|---|---|---|---|---|---|---|
| DP1176 (Construct) | 427 | 600 | 71 | 0.0003 | Y | 0.1290 | |
| ZH11-TC | 100 | 180 | 56 | | | | |
| DP0158 | 116 | 180 | 64 | | | | |
| DP1176.01 | 50 | 60 | 83 | 0.0006 | Y | 0.0202 | Y |
| DP1176.02 | 44 | 60 | 73 | 0.0192 | Y | 0.2347 | |
| DP1176.03 | 46 | 60 | 77 | 0.0060 | Y | 0.0996 | |
| DP1176.04 | 41 | 60 | 68 | 0.0883 | | 0.6204 | |
| DP1176.05 | 40 | 60 | 67 | 0.1633 | | 0.9375 | |
| DP1176.06 | 46 | 60 | 77 | 0.0060 | Y | 0.0996 | |
| DP1176.07 | 43 | 60 | 72 | 0.0330 | Y | 0.3383 | |
| DP1176.08 | 39 | 60 | 65 | 0.2054 | | 0.9718 | |
| DP1176.09 | 38 | 60 | 63 | 0.2961 | | 0.8470 | |
| DP1176.10 | 40 | 60 | 67 | 0.1372 | | 0.7911 | |

Example 8

Flowering Trait Observation for the OsMBD2 Transgenic Rice

The $T_2$ generation OsMBD2 transgenic plants were planted in Ningxia field (Ningxia, 38° 36'N, 106° 23'E, altitude 1106.3 m). The phenotype was recorded during the plant growth.

Method:

$T_2$ transgenic seeds were sterilized by 800 ppm carbendazol for 8 h at 32° C. and washed 3~5 times with distilled water, then soaked in water for 16 h at 32° C., germinated for 18 h at 35~37° C. in an incubator. The germinated seeds were planted in a seedbed field, and at 3-leaf stage, the seedlings were transplanted into field. Ten plants from each transgenic line were planted in one row, and ZH11-WT (Zhonghua 11 wild type), ZH11-TC (tissue cultured Zhonghua 11) and DP0158 (transformed with empty vector DP0158) were planted nearby the transgenic lines in the same block, and were used as controls.

The rice plants were managed by normal practice using pesticides and fertilizers. Plant phenotypes were observed and recorded during the experiments.

Heading date and maturity date were recorded. The heading date is the date when 50% young panicles head out the sheath of flag leaf for one plant in one row. The maturity date is the date when 90% glume, grain spikelet axis or vice glume become yellow from appearance, which is the best harvest period. If the heading date of the transgenic rice plants are earlier than that of the control plants (Zhonghua 11, ZH11-TC or DP0158 plants), the transgenic rice line is thought to be early heading plants and the gene play a role in regulating the flowering time of plants.

The plant height, effective panicle number and grain yield per plant were measured. The plant height is the length from the surface of the field to the top of the highest panicle or leaf and was measured before harvest. At the end of the season, some representative plants of each transgenic line were harvested from the middle of the row per line. The panicles first were cut and stored in one bag, and then the stems were cut above the earth and put in another bag. The effective panicle number per plant was obtained by counting, and the grain yield per plant was measured. The plant height, effective panicle number and grain yield data were statistically analyzed using mixed linear model by ASReml program.

Results:

The 12 OsMBD2 transgenic rice plants were tested in Ningxia field. At the beginning, the plants were managed by normal practice. When the main stem panicles reached panicle initiation stage I, watering was stopped. The rice plants suffered the drought stress. The heading date of the OsMBD2 transgenic rice lines were recorded. On August 16, eight transgenic rice lines exhibited 50% young panicles out the sheath of the flag leaf, while the ZH11-TC and DP0158 control plants exhibited 50% young panicles on August 26. Some OsMBD2 transgenic lines showed 10 days earlier heading date than the control plants, and these earlier heading transgenic rice plants also matured earlier than the controls for about 10 days. The OsMBD2 transgenic rice plants also showed better seed setting phenotype except the transgenic lines DP0988.01, DP0988.07, DP0988.08 and DP0988.12. Grain yield analysis showed all the OsMBD2 transgenic lines exhibited greater grain yields per plant than DP0158 control at the line level and three transgenic lines showed greater grain yields per plant than ZH11-TC plants (Table 52). These results indicate that OsMBD2 gene may regulate the heading date and/or flowering time in the transgenic rice plants, and OsMBD2 transgenic rice plant exhibited greater grain yield increase per plant after drought stress.

TABLE 52

Flowering trait and grain yield of OsMBD2 transgenic rice plants in Ningxia (1$^{st}$ experiment)

| Line ID | Days to heading date (d) | Diff of heading date | Days to maturity date (d) | Grain yield per plant (g) |
|---|---|---|---|---|
| ZH11-TC | 132 | / | 179 | 7.13 |
| DP0158 | 132 | 0 | 179 | 1.56 |
| DP0988.01 | 132 | 0 | 179 | 3.52 |
| DP0988.02 | 122 | 10 | 169 | 8.02 |
| DP0988.03 | 122 | 10 | 169 | 7.04 |
| DP0988.04 | 122 | 10 | 169 | 5.92 |
| DP0988.05 | 122 | 10 | 169 | 6.97 |
| DP0988.06 | 122 | 10 | 169 | 5.64 |
| DP0988.07 | 132 | 0 | 179 | 3.74 |
| DP0988.08 | 132 | 0 | 179 | 4.34 |

TABLE 52-continued

Flowering trait and grain yield of OsMBD2 transgenic rice plants in Ningxia (1st experiment)

| Line ID | Days to heading date (d) | Diff of heading date | Days to maturity date (d) | Grain yield per plant (g) |
|---|---|---|---|---|
| DP0988.09 | 122 | 10 | 169 | 8.20 |
| DP0988.10 | 122 | 10 | 169 | 4.68 |
| DP0988.11 | 122 | 10 | 169 | 10.09 |
| DP0988.12 | 132 | 0 | 179 | 4.73 |

Five OsMBD2 transgenic rice lines were choose and tested in Ningxia, and ZH11-TC and DP0158 seedling were used as controls. These seeds were sowed on April 14, and transplanted in field on May 15. At the beginning, the plants were managed by normal practice. When the main stem panicles reached panicle initiation stage I, watering was stopped. The rice plants suffered the drought stress. Four OsMBD2 transgenic rice lines showed 7~8 days earlier heading date and good seed setting phenotype compared to ZH1-TC and DP0158 rice plants. The earlier heading plants also matured earlier than the controls. Grain yield analysis showed that the grain yield per plant of four transgenic lines greater than either ZH11-TC and DP0158 rice plants (Table 53).

TABLE 53

Flowering trait and grain yield of OsMBD2 transgenic rice plants in Ningxia (2nd experiment)

| Line ID | Days to heading date (d) | Diff of heading date | Days to maturity date (d) | Grain yield per plant (g) |
|---|---|---|---|---|
| ZH11-TC | 120 | / | 157 | 5.09 |
| DP0158 | 120 | 0 | 157 | 2.41 |
| DP0988.02 | 113 | 7 | 149 | 5.30 |
| DP0988.09 | 113 | 7 | 149 | 5.83 |
| DP0988.10 | 111 | 9 | 149 | 5.45 |
| DP0988.11 | 112 | 8 | 149 | 6.24 |
| DP0988.12 | 120 | 0 | 157 | 5.09 |

The five OsMBD2 transgenic rice lines were also planted in the paddy field in Ningxia, and ZH11-TC and DP0158 seedling were used as controls. These seeds were sowed on April 14, and transplanted in field on May 15. All the five OsMBD2 transgenic rice lines showed 6~11 days earlier heading date and good seed setting phenotype compared to ZH1-TC and DP0158 rice plants. The earlier heading plants also matured earlier than the controls. Grain yield analysis showed that the grain yield per plant of four transgenic lines lower than ZH11-TC and DP0158 rice plants (Table 54).

The expression levels of OsMBD2 gene in the transgenic rice plants was shown in FIG. 13 and described in Example 3. The expression levels in DP0988.07, DP0988.08 and DP0988.12 were lower than in other rice lines, and the days of heading date of DP0988.07, DP0988.08 and DP0988.12 were longer than other rice lines. These results demonstrated the expression levels of OsMBD2 gene affect the heading date or flowering time in the transgenic rice plants.

TABLE 54

Flowering trait and grain yield of OsMBD2 transgenic rice plants in Ningxia (3rd experiment)

| Line ID | Days to heading date (d) | Diff of heading date | Days to maturity date (d) | Grain yield per plant (g) |
|---|---|---|---|---|
| ZH11-TC | 118 | / | 157 | 27.49 |
| DP0158 | 118 | 0 | 157 | 27.07 |
| DP0988.02 | 109 | 9 | 148 | 25.37 |
| DP0988.09 | 109 | 9 | 148 | 25.37 |
| DP0988.10 | 107 | 11 | 148 | 21.31 |
| DP0988.11 | 107 | 11 | 148 | 24.34 |
| DP0988.12 | 112 | 6 | 151 | 27.68 |

Example 9

Field Low Nitrogen Tolerance Assays of Mature Transgenic Rice Plants

Field low nitrogen tolerance assays were carried out in Beijing. One nitrogen level: N-0 (using fertilizer without nitrogen) was set in the experiment. Seed germination and seedling cultivation were performed as described in Example 4. The germinated seeds were planted in a seedbed field. At 3-leaf stage, the seedlings were transplanted into the testing field with 4 replicates and 10 plants per replicate for each transgenic line, and the 4 replicates were planted in the same block. The ZH11-TC and DP0158 plants were planted nearby the transgenic lines in the same block, and were used as controls in the statistical analysis.

The rice plants were managed by normal practice using pesticides, but applying phosphorous fertilizer and potassium fertilizer for N-0 treatment.

At the end of the season, six representative plants of each transgenic line were harvested from the middle of the row per line and grain yield per plant was measured. The grain yield per plant data were statistically analyzed using mixed linear model by ASReml program. Positive transgenic lines are selected based on the analysis (P<0.1).

1) Field NUE Validation Results of OsMtN3L (DP0902) Transgenic Rice

The OsMtN3L transgenic rice and its controls were planted in the paddy field without using nitrogen in the full growth period. The OsMtN3L transgenic rice plants grew thickly and better than their controls during vegetative stage. The grain yield per plant of OsMtN3L transgenic rice plants were measured. Table 55 shows that OsMtN3L transgenic rice exhibited significantly greater grain yield per plant than ZH11-TC control and greater grain yield per plant than DP0158 control at the construct level; and ten lines showed greater grain yield per plant than either ZH11-TC or DP0158 control at the transgenic line level under low nitrogen conditions. These results demonstrate that OsMtN3L transgenic rice obtained low nitrogen tolerance, and over-expression of OsMtN3L improves the grain yield of transgenic plants under low nitrogen conditions. OsMtN3L gene plays a role in enhancing low nitrogen tolerance and/or NUE.

TABLE 55

Grain yield analysis of OsMtN3L transgenic rice under field low nitrogen condition

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0902 (Construct) | 480 | 288 | 36.49 | 4.16 | 0.057 | Y | 2.23 | 0.310 | |
| ZH11-TC | 40 | 24 | 32.33 | | | | | | |
| DP0158 | 40 | 24 | 34.26 | | | | | | |
| DP0902.01 | 40 | 24 | 35.24 | 2.91 | 0.255 | | 0.98 | 0.702 | |
| DP0902.02 | 40 | 24 | 36.56 | 4.23 | 0.096 | Y | 2.30 | 0.370 | |
| DP0902.03 | 40 | 24 | 33.92 | 1.59 | 0.533 | | −0.34 | 0.893 | |
| DP0902.04 | 40 | 24 | 39.32 | 6.99 | 0.006 | Y | 5.06 | 0.048 | Y |
| DP0902.05 | 40 | 24 | 35.67 | 3.34 | 0.191 | | 1.41 | 0.581 | |
| DP0902.06 | 40 | 24 | 36.61 | 4.28 | 0.091 | Y | 2.35 | 0.350 | |
| DP0902.07 | 40 | 24 | 36.71 | 4.38 | 0.086 | Y | 2.45 | 0.339 | |
| DP0902.08 | 40 | 24 | 40.42 | 8.09 | 0.002 | Y | 6.16 | 0.016 | Y |
| DP0902.09 | 40 | 24 | 33.87 | 1.54 | 0.548 | | −0.39 | 0.879 | |
| DP0902.10 | 40 | 24 | 38.12 | 5.79 | 0.023 | Y | 3.86 | 0.131 | |
| DP0902.11 | 40 | 24 | 36.96 | 4.63 | 0.068 | Y | 2.70 | 0.289 | |
| DP0902.12 | 40 | 24 | 34.45 | 2.12 | 0.403 | | 0.19 | 0.940 | |

2) Field NUE Validation Results of OsANKL1 (DP0960) Transgenic Rice

The OsANKL1 transgenic rice and its controls were planted in the paddy field without using nitrogen in the full growth period. The OsANKL1 transgenic rice plants grew thickly and better than their controls during vegetative stage. The grain yield per plant of OsANKL1 transgenic rice plants were measured at the end the growth period. Table 56 shows that OsANKL1 transgenic rice exhibited greater grain yield per plant than ZH11-TC control and slightly greater grain yield per plant than DP0158 control at the construct level; and six lines showed greater grain yield per plant than either ZH11-TC or DP0158 control at the transgenic line level under low nitrogen conditions. These results demonstrate that OsANKL1 transgenic rice obtained low nitrogen tolerance, and over-expression of OsANKL1 improves the grain yield of transgenic plants under low nitrogen conditions. OsANKL1 gene plays a role in enhancing low nitrogen tolerance and/or NUE.

Example 10

Laboratory Chlorate Assays of Transgenic Rice Plants

Nitrate is a major source of inorganic nitrogen utilized by higher plants. Chlorate is a nitrate analog which can be absorb, transported by the same system with nitrogen and reduced to a toxic compound (chlorite) by nitrate reductase (NR) in plants. $T_0$ further confirm the nitrogen use efficiency, chlorate solution is selected to treat seedlings, and seedlings which are sensitive to chlorate will be considered to have better nitrogen use efficiency or low nitrogen tolerance.

Laboratory Chlorate Assay Method:

About ten transgenic lines from a construct were selected and tested by chlorate solution. ZH11-TC transgenic plants were used as control.

$T_2$ transgenic seeds were sterilized and germinated as description in Example 4, and this assay was performed in culture room kept temperature at 28-30° C. and humidity

TABLE 56

Grain yield analysis of OsANKL1 (DP0960) transgenic rice under field low nitrogen condition

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0960 (Construct) | 480 | 230 | 34.29 | 3.15 | 0.194 | | 0.3 | 0.9 | |
| ZH11-TC | 40 | 21 | 31.14 | | | | | | |
| DP0158 | 40 | 22 | 33.98 | | | | | | |
| DP0960.01 | 40 | 16 | 36.51 | 5.37 | 0.055 | Y | 2.53 | 0.370 | |
| DP0960.02 | 40 | 18 | 37.58 | 6.44 | 0.021 | Y | 3.59 | 0.202 | |
| DP0960.03 | 40 | 20 | 31.67 | 0.53 | 0.851 | | −2.32 | 0.411 | |
| DP0960.04 | 40 | 17 | 32.13 | 0.99 | 0.725 | | −1.85 | 0.508 | |
| DP0960.05 | 40 | 20 | 33.5 | 2.36 | 0.404 | | −0.49 | 0.862 | |
| DP0960.07 | 40 | 20 | 38.57 | 5.43 | 0.052 | Y | 2.59 | 0.358 | |
| DP0960.09 | 40 | 20 | 35.87 | 4.53 | 0.108 | | 1.68 | 0.547 | |
| DP0960.10 | 40 | 20 | 33.95 | 2.81 | 0.319 | | −0.04 | 0.99 | |
| DP0960.11 | 40 | 20 | 32.9 | 1.76 | 0.533 | | −1.09 | 0.699 | |
| DP0960.12 | 40 | 20 | 34.17 | 3.03 | 0.283 | | 0.18 | 0.948 | |
| DP0960.13 | 40 | 18 | 34.61 | 3.47 | 0.218 | | 0.63 | 0.823 | |
| DP0960.15 | 40 | 21 | 32.22 | 1.08 | 0.699 | | −1.76 | 0.529 | | around 30%. The germinated seeds were placed in a tube with a hole at the bottom, and water cultured at 30° C. for 6 days till one-leaf and one-terminal bud stage. Uniform seedlings about 5.5 cm in height were selected for chlorate screening. Randomized block design was used in this experiment. There are five blocks in one screened container. Each transgenic line was placed in one row (12 plants/line), and ZH11-TC seedlings were placed in 3 rows (3*12 plants) randomly in one block. Then the seedlings were treated with 0.4 mM chlorate in concentration for 3-5 days at 10 h day/14 h night, the treated seedlings first encountered night and absorb the chlorate solution which was changed at the third day. After treated for 5 days, the seedlings were then cultured in 1/10 Hoagland's solution for 4 days. The seedlings with withered leaves and totally without green are counted as sensitive; while the seedlings only with necrosed leaves or stem, or bleached leaves are not considered to be sensitive seedlings.

Sensitive rate was used as a parameter to for this assay, which is the percentage of the number of sensitive plants over the total plant number.

The data was analyzed at construct level (all transgenic plants compared to the control) and transgenic line level (different transgenic lines compared to the control) using a statistic model of "Y seg+line (seg)+rep+error" with random effect of "rep" and Statistic Method of "SAS Proc Glimmix".

Chlorate Assay Results:

Chlorate Validation Results of OsANKL1 (DP0960) Transgenic Rice

For OsANKL1 transgenic seedlings, in the first experiment, after treated with 0.4 mM chlorate solution for 5 days and cultured in 1/10 Hoagland solution for 4 days, 369 of the 600 (62%) transgenic seedlings died, whereas 70 of the 180 (39%) ZH11-TC seedlings died. The sensitive rate of OsANKL1 transgenic seedlings was significantly higher than that of the ZH11-TC control (P value=0.0000), indicating the OsANKL1 transgenic seedlings had increased chlorate sensitivity.

Further analysis at transgenic line level demonstrated that all the ten transgenic lines had higher sensitive rates than ZH11-TC control, and seven lines showed significantly higher chlorate sensitive rates than ZH11-TC seedlings as illustrated in Table 57. These results strongly demonstrate that OsANKL1 transgenic rice plants had enhanced chlorate sensitivity compared with ZH11-TC seedlings at the construct and the transgenic line level at seedling stages.

TABLE 57

Chlorate sensitive assay of OsANKL1 transgenic rice seedlings (1st experiment)

| Line ID | Number of Dead seedlings | Number of total seedlings | Sensitive rate (%) | CK = ZH11-TC P value | P ≤ 0.05 |
|---|---|---|---|---|---|
| DP0960 (Construct) | 369 | 600 | 62 | 0.0000 | Y |
| ZH-TC | 70 | 180 | 39 | | |
| DP0960.01 | 31 | 60 | 52 | 0.0890 | |
| DP0960.02 | 31 | 60 | 52 | 0.0890 | |
| DP0960.05 | 48 | 60 | 80 | 0.0000 | Y |
| DP0960.07 | 37 | 60 | 62 | 0.0036 | Y |
| DP0960.09 | 41 | 60 | 68 | 0.0003 | Y |
| DP0960.10 | 30 | 60 | 50 | 0.1370 | |
| DP0960.11 | 36 | 60 | 60 | 0.0065 | Y |
| DP0960.12 | 40 | 60 | 67 | 0.0005 | Y |
| DP0960.13 | 34 | 60 | 57 | 0.0201 | Y |
| DP0960.15 | 41 | 60 | 68 | 0.0003 | Y |

In the second experiment, after treated with 0.4 mM chlorate solution for 5 days and cultured in 1/10 Hoagland solution for 4 days, 216 of the 600 (36%) transgenic seedlings died, whereas 33 of the 180 (18%) ZH11-TC seedlings died. The sensitive rate of OsANKL1 transgenic seedlings was significantly higher than ZH11-TC control, indicating that the OsANKL1 transgenic seedlings had increased chlorate sensitivity.

Analysis at transgenic line level demonstrated that eight transgenic lines exhibited significantly higher sensitive rates than ZH11-TC control (Table 58). All these results demonstrate that OsANKL1 transgenic rice plants obtained enhanced chlorate sensitivity at seedling stages. Over-expression of OsANKL1 increases the chlorate sensitivity of transgenic plants.

TABLE 58

Chlorate sensitive assay of OsANKL1 transgenic rice seedlings (2nd experiment)

| Line ID | Number of Dead seedlings | Number of total seedlings | Sensitive rate (%) | CK = ZH11-TC P value | P ≤ 0.05 |
|---|---|---|---|---|---|
| DP0960 (Construct) | 216 | 600 | 36 | 0.0000 | Y |
| ZH11-TC | 33 | 180 | 18 | | |
| DP0960.01 | 20 | 60 | 33 | 0.0192 | Y |
| DP0960.02 | 19 | 60 | 32 | 0.0350 | Y |
| DP0960.05 | 19 | 60 | 32 | 0.0350 | Y |
| DP0960.07 | 14 | 60 | 23 | 0.4002 | |
| DP0960.09 | 20 | 60 | 33 | 0.0192 | Y |
| DP0960.10 | 13 | 60 | 22 | 0.5707 | |
| DP0960.11 | 28 | 60 | 47 | 0.0000 | Y |
| DP0960.12 | 36 | 60 | 60 | 0.0000 | Y |
| DP0960.13 | 23 | 60 | 38 | 0.0027 | Y |
| DP0960.15. | 24 | 60 | 40 | 0.0014 | Y |

Example 11

Transformation and Evaluation of Maize with Rice Drought Tolerance Genes

Maize plants can be transformed to over-express *Oryza sativa* drought tolerance genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

Example 12

Laboratory Drought Screening of Rice Drought Tolerance Genes in *Arabidopsis*

To understand whether rice drought tolerance genes can improve dicot plants' drought tolerance, or other traits, the rice drought tolerance gene over-expression vectors were transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

A 16.8-kb T-DNA based binary vector which is called pBC-yellow was used in this experiment. This vector contains the RD29a promoter driving expression of the gene for ZS-Yellow, which confers yellow fluorescence to transformed seed. The rice drought tolerance genes were cloned as described in Example 1, and constructed in the Gateway vector. Then using the INVITROGEN™ GATEWAY® technology, an LR Recombination Reaction was performed on the entry clone containing the directionally cloned PCR product and the pBC-yellow vector, and the over-expression vectors were obtained.

$T_2$ seeds were used for lab drought assay. *Arabidopsis* drought screening is a soil-based water withdrawal assay performed in a growth chamber with conditions of light intensity 145 µMol, temperature 22° C. day/20° C. night and humidity 60%. The transgenic seeds were sorted by COPAS™ (Complex Object Parametric Analyzer and Sorter, a seed sorter, Union Biometrica), and were stratified by putting in 0.1% agarose solution, and placing at 4° C. for 3 days. Wild-type *Arabidopsis* were used as control and stratified as above. 36 plants each for over-expression transgenic *Arabidopsis* and wild-type were planted equidistantly and alternatively to each other in a zig-zag fashion. The soil composition was 3 parts peat moss, 2 parts vermiculite and 1 part perlite. Apart from these, fertilizers and fungicides were added to the soil in the following concentrations: NPK (Nitrogen, Phosphorus, Potassium)-1 gm/kg soil, Micronutrients-0.5 gm/kg soil, Fungicide-0.5 gm/kg soil. Plants were thinned to 9 plants per pot (72 plants per flat), and were well watered for the first 12 days, then saturated with 1 L of deionized water for 30 min with excess water drained off completely. The plants were imaged between days 28 and 36 after germination using an imaging device and data were analyzed. The flats were rotated each day from the second day after sowing till the last day of imaging. The files generated in the imaging device were converted into XLS files and put in a Stan's format and sent to ESL for generating Stan's score for the experimental lines. Rate of decay or wilting under drought conditions is used as tested parameter. The cut-off Score=1.5.

What is claimed is:

1. A method of increasing drought tolerance and/or enhancing grain yield in a plant, the method comprising:
   (a) expressing in a plant a polynucleotide encoding a polypeptide comprising an amino acid sequence of at least 95% sequence identity to SEQ ID NO: 16 operably linked to at least one heterologous regulatory element, wherein the expression level of the polynucleotide is increased compared to that of a control plant; and
   (b) selecting a plant of part (a) comprising the polynucleotide operably linked to the regulatory element for increased drought tolerance and/or enhanced yield as compared to a control plant not comprising the polynucleotide operably linked to the regulatory element.

2. The method of claim 1, wherein the expression of the polynucleotide is increased by:
   expressing in the plant a recombinant DNA construct comprising the polynucleotide sequence operably linked to the at least one heterologous regulatory element.

* * * * *

SEQUENCE LISTING

```
<160> NUMBER OF SEQ ID NOS: 57

<210> SEQ ID NO 1
<211> LENGTH: 11934
<212> TYPE: DNA
<213> ORGANISM: Artificial Sequence
<220> FEATURE:
<223> OTHER INFORMATION: The nucleotide sequence of vector DP0158

<400> SEQUENCE: 1
gaattctcta gtcccgatct agtaacatag atgacaccgc gcgcgataat ttatcctagt      60
ttgcgcgcta tattttgttt tctatcgcgt attaaatgta taattgcggg actctaatca     120 taaaaccca tctcataaat aacgtcatgc attacatgtt aattattaca tgcttaacgt     180
aattcaacag aaattatatg ataatcatcg caagaccggc aacaggattc aatcttaaga     240
aacgcggccg cttcagttgt ggcccagctt ggaggtcgac tcgcgaggat ctctgcagag     300
agatagattt gtagagagag actggtgatt tcagcgtgtc ctctccaaat gaaatgaact     360
tccttatata gaggaagggt cttgcgaagg atagtgggat tgtgcgtcat cccttacgtc     420
agtggagata tcacatcaat ccacttgctt tgaagacgtg gttggaacgt cttctttttc     480
cacgatgctc ctcgtgggtg ggggtccatc tttgggacca ctgtcggcag aggcatcttg     540
aacgatagcc tttcctttat cgcaatgatg gcatttgtag gtgccacctt cctttttctac     600 tgtccttttg atgaagtgac agatagctgg gcaatggaat ccgaggaggt ttcccgatat     660
```

```
tacccttttgt tgaaaagtct caatagccct ttggtcttct gagactgtat ctttgatatt    720
cttggagtag acgagagtgt cgtgctccac catgttcaca tcaatccact tgctttgaag    780
acgtggttgg aacgtcttct ttttccacga tgctcctcgt gggtgggggt ccatctttgg    840
gaccactgtc ggcagaggca tcttgaacga tagccttttcc tttatcgcaa tgatggcatt    900
tgtaggtgcc accttccttt tctactgtcc ttttgatgaa gtgacagata gctgggcaat    960
ggaatccgag gaggtttccc gatattaccc tttgttgaaa agtctcaata gcccttggt    1020
cttctgagac tgtatctttg atattcttgg agtagacgag agtgtcgtgc tccaccatgt    1080
tgccaagctg ctctaagctt tggcggccgc attcgcaaaa cacacctaga ctagatttgt    1140
tttgctaacc caattgatat taattatata tgattaatat ttatatgtat atggatttgg    1200
ttaatgaaat gcatctggtt catcaaagaa ttataaagac acgtgacatt catttaggat    1260
aagaaatatg gatgatctct ttctctttta ttcagataac tagtaattac ataacaca    1320
caactttgat gcccacatta tagtgattag catgtcacta tgtgtgcatc ctttttatttc    1380
atacattaat taagttggcc aatccagaag atggacaagt ctaggttaac catgtggtac    1440
ctacgcgttc gaatatccat gggccgctac aggaacaggt ggtggcggcc ctcggtgcgc    1500
tcgtactgct ccacgatggt gtagtcctcg ttgtgggagg tgatgtccag cttggcgtcc    1560
acgtagtagt agccgggcag ctgcacgggc ttcttggcca tgtagatgga cttgaactcc    1620
accaggtagt ggccgccgtc cttcagcttc agggccttgt gggtctcgcc cttcagcacg    1680
ccgtcgcggg ggtacaggcg ctcggtggag gcctcccagc ccatggtctt cttctgcatc    1740
acggggccgt cggaggggaa gttcacgccg atgaacttca ccttgtagat gaagcagccg    1800
tcctgcaggg aggagtcctg ggtcacggtc gccacgccgc cgtcctcgaa gttcatcacg    1860
cgctcccact gaagccctc ggggaaggac agcttcttgt agtcgggat gtcggcgggg    1920
tgcttcacgt acaccttgga gccgtactgg aactgggggg acaggatgtc ccaggcgaag    1980
ggcagggggc cgcccttcgt caccttcagc ttcacggtgt tgtggccctc gtaggggcgg    2040
ccctcgccct cgccctcgat ctcgaactcg tggccgttca cggtgccctc catgcgcacc    2100
ttgaagcgca tgaactcggt gatgacgttc tcggaggagg ccatggtggc gaggatctac    2160
tcggctacac tcacacgctc gctctcgcag ttgcaggtgt aagtttctag ctagggcact    2220
cacggggtac gtatttgtag ccagccacgc acggtctgag ctcgccatgt gccgccatgc    2280
atgcggggcc acgtcgccag cgtacgcggc catcgtcgct gacgaaggta gcgcattcaa    2340
gtccggtcgg tagaggtcag ctgggtcgtt cgccgatggt agttgccgcc cggactcagt    2400
gggcggtagg cgaaggctag caagcagacg actccattca tgcgcatcat ccaaaggtga    2460
tgcaaagcct tccaaacgcg attgtctcat gatgtttccg tctcttgtta cgaggagtac    2520
aatttttttct tatacacgaa cgttactttta tgtcacatttt ccatgccatg aacaccttgg    2580
cttcaaataa gtgagtgttt ttttttcacat tctgtggcat aaacagaatt tctagagtgg    2640
catttgtgat acattgtgaa agctaagagt ggtaaaagta aaataaaatt gttttgcttt    2700
tgccgcggaa tggaaattat ttgtcaaaac ctaagagtgg caaaactgaa atgtcaaaac    2760
ctagagtgac ataaacaaaa tttacccatc actaaatgag cacaaaatat ttcaccacaa    2820
tggaggtatg tgaggtccga tgtactacta gagctcatcg gaaaagcatc ctcttgatga    2880
gtaaacctct tgaagtactg taccaccaca tttttatttat cctcatcggc ttatttttag    2940
gccacggtta ttctcacgaa gagacggtta acccttctcg tagactacac atcgagatcc    3000
actagttcta gagcggccag cttcgaagct tggcactggc cgtcgtttta caacgtcgtg    3060
```

```
actgggaaaa ccctggcgtt acccaactta atcgccttgc agcacatccc cctttcgcca   3120
gctggcgtaa tagcgaagag gcccgcaccg atcgccttc  ccaacagttg cgcagcctga   3180
atggcgaatg ctagagcagc ttgagcttgg atcagattgt cgtttcccgc cttcagttta   3240
aactatcagt gtttgacagg atatattggc gggtaaacct aagagaaaag agcgtttatt   3300
agaataatcg gatatttaaa agggcgtgaa aaggtttatc cgttcgtcca tttgtatgtg   3360
catgccaacc acagggttcc cctcgggatc aaagtacttt gatccaaccc ctccgctgct   3420
atagtgcagt cggcttctga cgttcagtgc agccgtcttc tgaaaacgac atgtcgcaca   3480
agtcctaagt tacgcgacag gctgccgccc tgcccttttc ctggcgtttt cttgtcgcgt   3540
gttttagtcg cataaagtag aatacttgcg actagaaccg gagacattac gccatgaaca   3600
agagcgccgc cgctggcctg ctgggctatg cccgcgtcag caccgacgac caggacttga   3660
ccaaccaacg ggccgaactg cacgcggccg gctgcaccaa gctgttttcc gagaagatca   3720
ccggcaccag gcgcgaccgc ccggagctgg ccaggatgct tgaccaccta cgccctggcg   3780
acgttgtgac agtgaccagg ctagaccgcc tggcccgcag cacccgcgac ctactggaca   3840
ttgccgagcg catccaggag gccggcgcgg gcctgcgtag cctggcagag ccgtgggccg   3900
acaccaccac gccggccggc cgcatggtgt tgaccgtgtt cgccggcatt gccgagttcg   3960
agcgttccct aatcatcgac cgcacccgga gcgggcgcga ggccgccaag gcccgaggcg   4020
tgaagtttgg cccccgccct accctcaccc cggcacagat cgcgcacgcc cgcgagctga   4080
tcgaccagga aggccgcacc gtgaaagagg cggctgcact gcttggcgtg catcgctcga   4140
ccctgtaccg cgcacttgag cgcagcgagg aagtgacgcc caccgaggcc aggcggcgcg   4200
gtgccttccg tgaggacgca ttgaccgagg ccgacgccct ggcggccgcc gagaatgaac   4260
gccaagagga caagcatga  aaccgcacca ggacggccag gacgaaccgt ttttcattac   4320
cgaagagatc gaggcggaga tgatcgcggc cgggtacgtg ttcgagccgc ccgcgcacgt   4380
ctcaaccgtg cggctgcatg aaatcctggc cggtttgtct gatgccaagc tggcggcctg   4440
gccggccagc ttggccgctg aagaaaccga gcgccgccgt ctaaaaaggt gatgtgtatt   4500
tgagtaaaac agcttgcgtc atgcggtcgc tgcgtatatg atgcgatgag taaataaaca   4560
aatacgcaag gggaacgcat gaaggttatc gctgtactta accagaaagg cgggtcaggc   4620
aagacgacca tcgcaaccca tctagcccgc gccctgcaac tcgccggggc cgatgttctg   4680
ttagtcgatt ccgatcccca gggcagtgcc cgcgattggg cggccgtgcg gaagatcaa   4740
ccgctaaccg ttgtcggcat cgaccgcccg acgattgacc gcgacgtgaa ggccatcggc   4800
cggcgcgact tcgtagtgat cgacggagcg ccccaggcgg cggacttggc tgtgtccgcg   4860
atcaaggcag ccgacttcgt gctgattccg gtgcagccaa gccttacga  catatgggcc   4920
accgccgacc tggtggagct ggttaagcag cgcattgagg tcacggatgg aaggctacaa   4980
gcggcctttg tcgtgtcgcg ggcgatcaaa ggcacgcgca tcggcggtga ggttgccgag   5040
gcgctggccg gtacgagct  gcccattctt gagtcccgta tcacgcagcg cgtgagctac   5100
ccaggcactg ccgccgccgg cacaaccgtt cttgaatcag aacccgaggg cgacgctgcc   5160
cgcgaggtcc aggcgctggc cgctgaaatt aaatcaaaac tcatttgagt taatgaggta   5220
aagagaaaat gagcaaaagc acaaacacgc taagtgccgg ccgtccgagc gcacgcagca   5280
gcaaggctgc aacgttggcc agcctggcag acacgccagc catgaagcgg gtcaactttc   5340
agttgccggc ggaggatcac accaagctga agatgtacgc ggtacgccaa ggcaagacca   5400
```

```
ttaccgagct gctatctgaa tacatcgcgc agctaccaga gtaaatgagc aaatgaataa      5460
atgagtagat gaattttagc ggctaaagga ggcggcatgg aaaatcaaga acaaccaggc      5520
accgacgccg tggaatgccc catgtgtgga ggaacgggcg gttggccagg cgtaagcggc      5580
tgggttgtct gccggccctg caatggcact ggaaccccca agcccgagga atcggcgtga      5640
cggtcgcaaa ccatccggcc cggtacaaat cggcgcggcg ctgggtgatg acctggtgga      5700
gaagttgaag gccgcgcagg ccgcccagcg gcaacgcatc gaggcagaag cacgccccgg      5760
tgaatcgtgg caagcggccg ctgatcgaat ccgcaaagaa tcccggcaac cgccggcagc      5820
cggtgcgccg tcgattagga agccgcccaa gggcgacgag caaccagatt ttttcgttcc      5880
gatgctctat gacgtgggca cccgcgatag tcgcagcatc atggacgtgg ccgttttccg      5940
tctgtcgaag cgtgaccgac gagctggcga ggtgatccgc tacgagcttc agacgggca      6000 cgtagaggtt ccgcagggc cggccggcat ggccagtgtg tgggattacg acctggtact      6060
gatggcggtt tccatctaa ccgaatccat gaaccgatac cgggaaggga agggagacaa      6120
gcccggccgc gtgttccgtc cacacgttgc ggacgtactc aagttctgcc ggcgagccga      6180
tggcggaaag cagaaagacg acctggtaga aacctgcatt cggttaaaca ccacgcacgt      6240
tgccatgcag cgtacgaaga aggccaagaa cggccgcctg gtgacggtat ccagggtga      6300 agccttgatt agccgctaca agatcgtaaa gagcgaaacc gggcggccgg agtacatcga      6360
gatcgagcta gctgattgga tgtaccgcga gatcacagaa ggcaagaacc cggacgtgct      6420
gacggttcac cccgattact ttttgatcga tcccggcatc ggccgttttc tctaccgcct      6480
ggcacgccgc gccgcaggca aggcagaagc cagatggttg ttcaagacga tctacgaacg      6540
cagtggcagc gccggagagt tcaagaagtt ctgtttcacc gtgcgcaagc tgatcgggtc      6600
aaatgacctg ccggagtacg atttgaagga ggaggcgggg caggctggcc cgatcctagt      6660
catgcgctac cgcaacctga tcgagggcga agcatccgcc ggttcctaat gtacggagca      6720
gatgctaggg caaattgccc tagcagggga aaaaggtcga aaaggtctct ttcctgtgga      6780
tagcacgtac attgggaacc caaagccgta cattgggaac cggaacccgt acattgggaa      6840
cccaaagccg tacattggga accggtcaca catgtaagtg actgatataa aagagaaaaa      6900
aggcgatttt tccgcctaaa actctttaaa acttattaaa actcttaaaa cccgcctggc      6960
ctgtgcataa ctgtctggcc agcgcacagc cgaagagctg caaaaagcgc ctacccttcg      7020
gtcgctgcgc tccctacgcc ccgccgcttc gcgtcggcct atcgcggccg ctggccgctc      7080
aaaaatggct ggcctacggc caggcaatct accaggcgc ggacaagccg cgccgtcgcc      7140
actcgaccgc cggcgcccac atcaaggcac cctgcctcgc gcgtttcggt gatgacggtg      7200
aaaacctctg acacatgcag ctcccggaga cggtcacagc ttgtctgtaa gcggatgccg      7260
ggagcagaca gcccgtcag ggcgcgtcag cgggtgttgg cgggtgtcgg ggcgcagcca      7320
tgacccagtc acgtagcgat agcggagtgt atactggctt aactatgcgg catcagagca      7380
gattgtactg agagtgcacc atatgcggtg tgaaataccg cacagatgcg taaggagaaa      7440
ataccgcatc aggcgctctt ccgcttcctc gctcactgac tcgctgcgct cggtcgttcg      7500
gctgcggcga gcggtatcag ctcactcaaa ggcggtaata cggttatcca cagaatcagg      7560
ggataacgca ggaaagaaca tgtgagcaaa aggccagcaa aaggccagga accgtaaaaa      7620
ggccgcgttg ctggcgtttt tccataggct ccgcccccct gacgagcatc acaaaaatcg      7680
acgctcaagt cagaggtggc gaaacccgac aggactataa agataccagg cgtttccccc      7740
tggaagctcc ctcgtgcgct ctcctgttcc gaccctgccg cttaccggat acctgtccgc      7800
```

```
ctttctccct tcgggaagcg tggcgctttc tcatagctca cgctgtaggt atctcagttc    7860
ggtgtaggtc gttcgctcca agctgggctg tgtgcacgaa ccccccgttc agcccgaccg    7920
ctgcgcctta tccggtaact atcgtcttga gtccaacccg gtaagacacg acttatcgcc    7980
actggcagca gccactggta acaggattag cagagcgagg tatgtaggcg gtgctacaga    8040
gttcttgaag tggtggccta actacggcta cactagaagg acagtatttg gtatctgcgc    8100
tctgctgaag ccagttacct tcggaaaaag agttggtagc tcttgatccg gcaaacaaac    8160
caccgctggt agcggtggtt ttttttgttt gcaagcagca gattacgcgc agaaaaaagg    8220
atctcaagaa gatcctttga tcttttctac ggggtctgac gctcagtgga acgaaaactc    8280
acgttaaggg attttggtca tgcattctag gtactaaaac aattcatcca gtaaatata    8340 atattttatt ttctcccaat caggcttgat ccccagtaag tcaaaaaata gctcgacata    8400
ctgttcttcc ccgatatcct ccctgatcga ccggacgcag aaggcaatgt cataccactt    8460
gtccgccctg ccgcttctcc caagatcaat aaagccactt actttgccat ctttcacaaa    8520
gatgttgctg tctcccaggt cgccgtggga aaagacaagt tcctcttcgg cttttccgt    8580 ctttaaaaaa tcatacagct cgcgcggatc tttaaatgga gtgtcttctt cccagttttc    8640
gcaatccaca tcggccagat cgttattcag taagtaatcc aattcggcta agcggctgtc    8700
taagctattc gtatagggac aatccgatat gtcgatggag tgaaagagcc tgatgcactc    8760
cgcatacagc tcgataatct tttcagggct ttgttcatct tcatactctt ccgagcaaag    8820
gacgccatcg gcctcactca tgagcagatt gctccagcca tcatgccgtt caaagtgcag    8880
gacctttgga acaggcagct ttccttccag ccatagcatc atgtccttt cccgttccac    8940 atcataggtg gtcccttat accggctgtc cgtcattttt aaatataggt tttcattttc    9000
tcccaccagc ttatatacct tagcaggaga cattccttcc gtatctttta cgcagcggta    9060 ttttcgatc agtttttca attccggtga tattctcatt ttagccattt attatttcct    9120
tcctcttttc tacagtattt aaagataccc caagaagcta attataacaa gacgaactcc    9180
aattcactgt tccttgcatt ctaaaacctt aaataccaga aaacagcttt ttcaaagttg    9240
ttttcaaagt tggcgtataa catagtatcg acggagccga ttttgaaacc gcggtgatca    9300
caggcagcaa cgctctgtca tcgttacaat caacatgcta ccctccgcga gatcatccgt    9360
gtttcaaacc cggcagctta gttgccgttc ttccgaatag catcggtaac atgagcaaag    9420
tctgccgcct tacaacggct ctcccgctga cgccgtcccg gactgatggg ctgcctgtat    9480
cgagtggtga ttttgtgccg agctgccggt cggggagctg ttggctggct ggtggcagga    9540
tatattgtgg tgtaaacaaa ttgacgctta gacaacttaa taacacattg cggacgtttt    9600
taatgtactg aattaacgcc gaattaattc ggggatctg gattttagta ctggattttg    9660
gttttaggaa ttagaaattt tattgataga agtatttac aaatacaaat acatactaag    9720
ggtttcttat atgctcaaca catgagcgaa accctatagg aacccaatt cccttatctg    9780 ggaactactc acacattatt atggagaaac tcgagcttgt cgatcgacag atccggtcgg    9840
catctactct atttctttgc cctcggacga gtgctgggc gtcggtttcc actatcggcg    9900
agtacttcta cacagccatc ggtccagacg gccgcgcttc tgcgggcgat ttgtgtacgc    9960
ccgacagtcc cggctccgga tcggacgatt gcgtcgcatc gaccctgcgc ccaagctgca    10020
tcatcgaaat tgccgtcaac caagctctga tagagttggt caagaccaat gcggagcata    10080
tacgcccgga gtcgtggcga tcctgcaagc tccggatgcc tccgctcgaa gtagcgcgtc    10140
```

```
tgctgctcca tacaagccaa ccacggcctc cagaagaaga tgttggcgac ctcgtattgg   10200
gaatccccga acatcgcctc gctccagtca atgaccgctg ttatgcggcc attgtccgtc   10260
aggacattgt tggagccgaa atccgcgtgc acgaggtgcc ggacttcggg gcagtcctcg   10320
gcccaaagca tcagctcatc gagagcctgc gcgacgacg cactgacggt gtcgtccatc   10380
acagtttgcc agtgatacac atggggatca gcaatcgcgc atatgaaatc acgccatgta   10440
gtgtattgac cgattccttg cggtccgaat gggccgaacc cgctcgtctg gctaagatcg   10500
gccgcagcga tcgcatccat agcctccgcg accggttgta aacagcggg cagttcggtt   10560 tcaggcaggt cttgcaacgt gacaccctgt gcacggcggg agatgcaata ggtcaggctc   10620 tcgctaaaact ccccaatgtc aagcacttcc ggaatcggga gcgcggccga tgcaaagtgc   10680
cgataaacat aacgatcttt gtagaaacca tcggcgcagc tatttacccg caggacatat   10740
ccacgccctc ctacatcgaa gctgaaagca cgagattctt cgccctccga gagctgcatc   10800
aggtcggaga cgctgtcgaa cttttcgatc agaaacttct cgacagacgt cgcggtgagt   10860
tcaggctttt tcatatctca ttgccccccg ggatctgcga aagctcgaga gagatagatt   10920
tgtagagaga gactggtgat ttcagcgtgt cctctccaaa tgaaatgaac ttccttatat   10980
agaggaaggt cttgcgaagg atagtgggat tgtgcgtcat cccttacgtc agtggagata   11040
tcacatcaat ccacttgctt tgaagacgtg gttggaacgt cttctttttc cacgatgctc   11100
ctcgtgggtg ggggtccatc tttgggacca ctgtcggcag aggcatcttg aacgatagcc   11160
tttcctttat cgcaatgatg gcatttgtag gtgccacctt cctttctac tgtccttttg   11220 atgaagtgac agatagctgg gcaatggaat ccgaggaggt tcccgatat taccctttgt   11280 tgaaaagtct caatagccct ttggtcttct gagactgtat cttgatatt cttggagtag   11340 acgagagtgt cgtgctccac catgttatca catcaatcca cttgctttga agacgtggtt   11400
ggaacgtctt ctttttccac gatgctcctc gtgggtgggg gtccatcttt gggaccactg   11460
tcggcagagg catcttgaac gatagccttt cctttatcgc aatgatggca tttgtaggt   11520 ccaccttcct tttctactgt cctttgatg aagtgacaga tagctgggca atggaatccg   11580
aggaggtttc ccgatattac cctttgttga aaagtctcaa tagccctttg gtcttctgag   11640
actgtatctt tgatattctt ggagtagacg agagtgtcgt gctccaccat gttggcaagc   11700
tgctctagcc aatacgcaaa ccgcctctcc ccgcgcgttg gccgattcat taatgcagct   11760
ggcacgacag gtttcccgac tggaaagcgg gcagtgagcg caacgcaatt aatgtgagtt   11820
agctcactca ttaggcaccc caggctttac actttatgct tccggctcgt atgttgtgtg   11880
gaattgtgag cggataacaa tttcacacag gaaacagcta tgaccatgat tacg         11934
```

<210> SEQ ID NO 2
<211> LENGTH: 1349
<212> TYPE: DNA
<213> ORGANISM: Oryza sativa

<400> SEQUENCE: 2

```
gactccgacg accagaagct accggcgacg cgagcggaga agcgcggagg ggaggggcg      60 cgcgccgcca tggcgttcga gaagatcgtc gtggccaacc ccgtcgtcga gatgacggt    120 gatgagatga ctcgagttat ttggaaatgg atcaaagata agcttatatt ccctttcttg   180
gacttggaca taaaatacta tgacttaggt ctacctaatc gtgacgctac tggggacaaa   240
gttacaatag agagtgcaga agcgacccta aagtataatg tagccatcaa atgtgcaact   300
ataactccag atgaaggacg cgtgaaagag tttaatttaa gtgcaatgtg aagagtcca    360
```

```
aatgggacaa taaggaacat tttgaatgga actgttttcc gagaaccaat catctgcaag      420
aatattcctc ggcttgtacc tgggtggata aagcccatat gcattggacg acatgcattt      480
ggtgatcaat accgagcaac agatacagtt attaaaggtc ctgggaagtt gaagttagta      540
tttgatggca gagaggaaca aatagagttg gatgtgttca actttactgg tgctggtgga      600
gtagccttgt ctatgtataa tactgacgag tctatttggg cattcgctga agcttccatg      660
aacatggctt accagaaaag atggccactt tatcttagca ccaaaaacac gatcctcaaa      720
aaatacgatg aaggtttaa agatatattt caggagaact atgaaacaaa atggagagcc        780
aagtttgatg atgcaggaat atggtacgaa catcggctga ttgatgatat ggtggcctat      840
gcccttaaga gtgaaggtgg ctatgtttgg gcttgcaaga actatgatgg agatgtgcag      900
agcgatctaa ttgctcaagg ttttggatcg ctaggtctaa tgacatcagt tctggtgtgc      960
cctgatggta gaaccattga agctgaagct gctcatggta cagtcacacg ccattacaga     1020
gttcaccaaa aaggaggcga aactagtaca aatagcattg cttcaatatt tgcttggaca     1080
accggactag gacatagggc aaagctcgat gacaataaaa gactgttaga ttttgtacaa     1140
aaacttgaag ctgcttgtgt gggaacagtg gaatctggaa agatgacaaa ggatctagct     1200
cttcttgtac atgggccaaa tgttagccga gataagtatc ttaacactgt tgagttcatc     1260
gatgctgttg ctgaggattt aagaacaaga ttgtcagtaa catccaagtt atgaaggaat     1320
gaatagggca acggcagggg acatgttag                                        1349

<210> SEQ ID NO 3
<211> LENGTH: 1245
<212> TYPE: DNA
<213> ORGANISM: Oryza sativa

<400> SEQUENCE: 3
atggcgttcg agaagatcgt cgtggccaac cccgtcgtcg agatggacgg tgatgagatg       60
actcgagtta tttggaaatg gatcaaagat aagcttatat tcccttttctt ggacttggac     120 ataaaatact atgacttagg tctacctaat cgtgacgcta ctggggacaa agttacaata      180
gagagtgcag aagcgaccct aaagtataat gtagccatca aatgtgcaac tataactcca      240
gatgaaggac gcgtgaaaga gtttaattta agtgcaatgt ggaagagtcc aaatgggaca      300
ataaggaaca ttttgaatgg aactgttttc cgagaaccaa tcatctgcaa gaatattcct      360
cggcttgtac ctgggtggat aaagcccata tgcattggac gacatgcatt tggtgatcaa      420
taccgagcaa cagatacagt tattaaaggt cctgggaagt tgaagttagt atttgatggc      480
agagaggaac aaatagagtt ggatgtgttc aactttactg gtgctggtgg agtagccttg      540
tctatgtata tactgacga gtctatttgg gcattcgctg aagcttccat gaacatggct       600
taccagaaaa gatggccact ttatcttagc accaaaaaca cgatcctcaa aaaatacgat      660
ggaaggttta agatatatt tcaggagaac tatgaaacaa atggagagc caagtttgat        720 gatgcaggaa tatggtacga acatcggctg attgatgata tggtggccta tgcccttaag      780
agtgaaggtg gctatgtttg gcttgcaag aactatgatg gagatgtgca gagcgatcta       840
attgctcaag gttttggatc gctaggtcta atgacatcag ttctggtgtg ccctgatggt      900
agaaccattg aagctgaagc tgctcatggt acagtcacac gccattacag agttcaccaa      960
aaaggaggcg aaactagtac aaatagcatt gcttcaatat ttgcttggac aaccggacta     1020
ggacataggg caaagctcga tgacaataaa agactgttag attttgtaca aaaacttgaa     1080
```

-continued

```
gctgcttgtg tgggaacagt ggaatctgga aagatgacaa aggatctagc tcttcttgta    1140
catgggccaa atgttagccg agataagtat cttaacactg ttgagttcat cgatgctgtt    1200
gctgaggatt taagaacaag attgtcagta acatccaagt tatga                    1245
```

<210> SEQ ID NO 4
<211> LENGTH: 414
<212> TYPE: PRT
<213> ORGANISM: Oryza sativa

<400> SEQUENCE: 4

```
Met Ala Phe Glu Lys Ile Val Ala Asn Pro Val Val Glu Met Asp
1               5                   10                  15

Gly Asp Glu Met Thr Arg Val Ile Trp Lys Trp Ile Lys Asp Lys Leu
                20                  25                  30

Ile Phe Pro Phe Leu Asp Leu Asp Ile Lys Tyr Tyr Asp Leu Gly Leu
                35                  40                  45

Pro Asn Arg Asp Ala Thr Gly Asp Lys Val Thr Ile Glu Ser Ala Glu
50                      55                  60

Ala Thr Leu Lys Tyr Asn Val Ala Ile Lys Cys Ala Thr Ile Thr Pro
65                  70                  75                  80

Asp Glu Gly Arg Val Lys Glu Phe Asn Leu Ser Ala Met Trp Lys Ser
                85                  90                  95

Pro Asn Gly Thr Ile Arg Asn Ile Leu Asn Gly Thr Val Phe Arg Glu
                100                 105                 110

Pro Ile Ile Cys Lys Asn Ile Pro Arg Leu Val Pro Gly Trp Ile Lys
                115                 120                 125

Pro Ile Cys Ile Gly Arg His Ala Phe Gly Asp Gln Tyr Arg Ala Thr
130                     135                 140

Asp Thr Val Ile Lys Gly Pro Gly Lys Leu Lys Leu Val Phe Asp Gly
145                 150                 155                 160

Arg Glu Glu Gln Ile Glu Leu Asp Val Phe Asn Phe Thr Gly Ala Gly
                165                 170                 175

Gly Val Ala Leu Ser Met Tyr Asn Thr Asp Glu Ser Ile Trp Ala Phe
                180                 185                 190

Ala Glu Ala Ser Met Asn Met Ala Tyr Gln Lys Arg Trp Pro Leu Tyr
                195                 200                 205

Leu Ser Thr Lys Asn Thr Ile Leu Lys Lys Tyr Asp Gly Arg Phe Lys
210                 215                 220

Asp Ile Phe Gln Glu Asn Tyr Glu Thr Lys Trp Arg Ala Lys Phe Asp
225                 230                 235                 240

Asp Ala Gly Ile Trp Tyr Glu His Arg Leu Ile Asp Asp Met Val Ala
                245                 250                 255

Tyr Ala Leu Lys Ser Glu Gly Gly Tyr Val Trp Ala Cys Lys Asn Tyr
                260                 265                 270

Asp Gly Asp Val Gln Ser Asp Leu Ile Ala Gln Gly Phe Gly Ser Leu
                275                 280                 285

Gly Leu Met Thr Ser Val Leu Val Cys Pro Asp Gly Arg Thr Ile Glu
290                     295                 300

Ala Glu Ala Ala His Gly Thr Val Thr Arg His Tyr Arg Val His Gln
305                 310                 315                 320

Lys Gly Gly Glu Thr Ser Thr Asn Ser Ile Ala Ser Ile Phe Ala Trp
                325                 330                 335

Thr Thr Gly Leu Gly His Arg Ala Lys Leu Asp Asp Asn Lys Arg Leu
                340                 345                 350
```

Leu Asp Phe Val Gln Lys Leu Glu Ala Ala Cys Val Gly Thr Val Glu
        355                 360                 365

Ser Gly Lys Met Thr Lys Asp Leu Ala Leu Leu Val His Gly Pro Asn
    370                 375                 380

Val Ser Arg Asp Lys Tyr Leu Asn Thr Val Glu Phe Ile Asp Ala Val
385                 390                 395                 400

Ala Glu Asp Leu Arg Thr Arg Leu Ser Val Thr Ser Lys Leu
                405                 410

<210> SEQ ID NO 5
<211> LENGTH: 631
<212> TYPE: DNA
<213> ORGANISM: Oryza sativa

<400> SEQUENCE: 5
cactgacatg tggccttcct tcttcctccc ccctctctcc cttctctctc tttctctccc      60
cttcttcccc ttctgtcgac acgcgggatg caacaagag cgagcagcgg cgggcggcga     120
ggccggagct gcggcggtgg gcgggagggc ggcgagatcg agcggcggcg cgctgcgacg     180
gcgagggagc tgcgctcggc gggagagcaa gcggcgaagg aaaaggaccc ccaccctaga     240
caccgcccag cctggagctg cgctcggcgg cgagagcgag cggcggcgac aagtgtaagc     300
acacgttcgg tttgtttttt ttcttgtttc tttgattcgt agccgaagtt cataactgaa     360
ttttccttgt ttcaggacga cgtttaagag gatcctgaag gccaaatcga ccgagcgatt     420
cgatgggctc ccttacctgt tctcgctgct gaactgcctc atctgcctgt ggtatggact     480
tccctgggtc gccaatggca ggctgctcgt caccaccgtc aacggcaccg gagcggtgtt     540
ccagctcgcc tacatttgtc tcttcatctt ctacgcggac agcaagaaga cgagcgtaat     600
tcttcccatc ctgcacctaa ttttgtctta g                                   631

<210> SEQ ID NO 6
<211> LENGTH: 543
<212> TYPE: DNA
<213> ORGANISM: Oryza sativa

<400> SEQUENCE: 6
atgtggcctt ccttcttcct cccccctctc tcccttctct ctctttctct cccccttcttc      60 cccttctgtc gacacgcggg atggcaacaa gagcgagcag cggcgggcgg cgaggccgga     120
gctgcggcgg tgggcgggag ggcggcgaga tcgagcggcg gcgcgctgcg acggcgaggg     180
agctgcgctc ggcgggagag caagcggcga aggaaaagga cccccaccct agacaccgcc     240
cagcctggag ctgcgctcgg cggcgagagc gagcggcggc gacaagtgac gacgtttaag     300
aggatcctga aggccaaatc gaccgagcga ttcgatgggc tcccttacct gttctcgctg     360
ctgaactgcc tcatctgcct gtggtatgga cttccctggg tcgccaatgg caggctgctc     420
gtcaccaccg tcaacggcac cggagcggtg ttccagctcg cctacatttg tctcttcatc     480
ttctacgcgg acagcaagaa gacgagcgta attcttccca cctgcacct aattttgtct     540 tag                                                                   543

<210> SEQ ID NO 7
<211> LENGTH: 180
<212> TYPE: PRT
<213> ORGANISM: Oryza sativa

<400> SEQUENCE: 7

Met Trp Pro Ser Phe Phe Leu Pro Pro Leu Ser Leu Leu Ser Leu Ser
1               5                   10                  15

Leu Pro Phe Phe Pro Phe Cys Arg His Ala Gly Trp Gln Gln Glu Arg
            20                  25                  30

Ala Ala Ala Gly Gly Glu Ala Gly Ala Ala Val Gly Gly Arg Ala
        35                  40                  45

Ala Arg Ser Ser Gly Gly Ala Leu Arg Arg Arg Gly Ser Cys Ala Arg
    50                  55                  60

Arg Glu Ser Lys Arg Arg Lys Arg Thr Pro Thr Leu Asp Thr Ala
65              70                  75                  80

Gln Pro Gly Ala Ala Leu Gly Gly Glu Ser Glu Arg Arg Gln Val
            85                  90                  95

Thr Thr Phe Lys Arg Ile Leu Lys Ala Lys Ser Thr Glu Arg Phe Asp
            100                 105                 110

Gly Leu Pro Tyr Leu Phe Ser Leu Leu Asn Cys Leu Ile Cys Leu Trp
            115                 120                 125

Tyr Gly Leu Pro Trp Val Ala Asn Gly Arg Leu Leu Val Thr Thr Val
    130                 135                 140

Asn Gly Thr Gly Ala Val Phe Gln Leu Ala Tyr Ile Cys Leu Phe Ile
145             150                 155                 160

Phe Tyr Ala Asp Ser Lys Lys Thr Ser Val Ile Leu Pro Ile Leu His
                165                 170                 175

Leu Ile Leu Ser
            180

<210> SEQ ID NO 8
<211> LENGTH: 1459
<212> TYPE: DNA
<213> ORGANISM: Oryza sativa

<400> SEQUENCE: 8
gctgcaaagg aggaagagaa agagtgttga ccgggggaga agagaggaga agccgggaag      60
agggccggga tggcgtcgag caacggagag caacctccag aatcgccgaa ggaagcaaat     120
gctgcgcctg tagcagccaa gcttgccatg cgtcagggc gcgatggatg tgagaggctc     180
aaggatctgg tgagtaggga agacgatgct actacgatgg ttgtggccat ggcgacaagc     240
aagaacgtgg acgacacaag acgacctccc cctccccgtg taattatgga tcccagctc     300
ctcatggctg cacggaatgg agcttgccag tctcttgaga gcctagcttc tcctcggcca     360
tgaggtgcgt tgtcaaacct tgcctgaatc ccatctaatc atctacttgc ccgaaccaga     420
tgagggagct ccgaccacag atccaattga agatcaggct gaaggaatct ctgcgactga     480
tcagcaagcc tctggtgctg tatattcgct ctcgctcctg gagggactga ctcttgactc     540
ggaccagaac tccgcgctgc atgtggtggc agcctccggt gacagccagg cgtatgtgga     600
gtgtgcgcgg atggtgtacg accaggcgag gcacctactc ggcgcggcca acaacaacgg     660
cgacacgccc ctgcactgcg ccgctgcagc tgggaaccac tcctcgcgct ggctgctgct     720
gcgcctgcgc gtgacagcag cggtgcagcg agggtggatg accaggagct cctagcaagg     780
aggaagaaca aggtcggtga gacggctttg cacggggcgg tccgtgctgg ccacagcaaa     840
gtggtggagg tcctcatgaa ggaggatccg ggactggccg gcgttgatcg gcacgacggc     900
acgtcaccgc tgtaccttgc cgtttcgttg ggacgcttcg agattgcgtg ggatctgctt     960
gatatgagct ctaggaaatt atcttactcc ggaccagatg gtcagaatgt cttgcacgtc    1020
gcagtacaac accccaagg tatgcgccac attaccgtac tctctttgtt gccccttccat    1080

-continued

```
tacatcagta ataacaaaat aattatgttt gttttaaaag atcaattaaa tccaactcat    1140
tatatattca acaatgcaca gcaccgttaa acaacctgta aataaagctg tatcgaaaat    1200
tatggttttg aggatatcat ctaattaaga ttgtttgtat aaaaaggaag agattcgtga    1260 tcccctata tatatactga ggcaaagact tttttttta gtacagatta attaatttgg     1320
gtctcttact ccttttatga taataactct attttatct tggatttgta tatacttttg    1380
gatataaaga gcataggtag gaagtagacc taatcgacta tctcgtcaac atgtttgggt   1440
atgggtttgt tgcgatctc                                                1459

<210> SEQ ID NO 9
<211> LENGTH: 699
<212> TYPE: DNA
<213> ORGANISM: Oryza sativa

<400> SEQUENCE: 9
atggcgtcga gcaacggaga gcaacctcca gaatcgccga aggaagcaaa tgctgcgcct     60
gtagcagcca agcttgccat ggcgtcaggg cgcgatggat gtgagaggct caaggatctg    120
atgagggagc tccgaccaca gatccaattg aagatcaggc tgaaggaatc tctgcgactg    180
atcagcaagc ctctgccagg cgtatgtgga gtgtgcgcgg atggtgtacg accaggcgag    240
gcacctactc ggcgcggcca acaacaacgg cgacacgccc ctgcactgcg ccgctgcagc    300
tgggaaccac tcctcgcgct ggctgctgct gcgcctgcgc gtgacagcag cggtgcagcg    360
agggtggatg accaggagct cctagcaagg aggaagaaca aggtcggtga dacggctttg    420
cacggggcgg tccgtgctgg ccacagcaaa gtggtggagg tcctcatgaa ggaggatccg    480
ggactggccg cgttgatcg gcacgacggc acgtcaccgc tgtaccttgc cgtttcgttg     540
ggacgcttcg agattgcgtg ggatctgctt gatatgagct ctaggaaatt atcttactcc    600
ggaccagatg gtcagaatgt cttgcacgtc gcagtacaac acccccaaga tcaattaaat    660
ccaactcatt atatattcaa caatgcacag caccgttaa                          699

<210> SEQ ID NO 10
<211> LENGTH: 232
<212> TYPE: PRT
<213> ORGANISM: Oryza sativa

<400> SEQUENCE: 10

Met Ala Ser Ser Asn Gly Glu Gln Pro Pro Glu Ser Pro Lys Glu Ala
1               5                   10                  15

Asn Ala Ala Pro Val Ala Ala Lys Leu Ala Met Ala Ser Gly Arg Asp
                20                  25                  30

Gly Cys Glu Arg Leu Lys Asp Leu Met Arg Glu Leu Arg Pro Gln Ile
            35                  40                  45

Gln Leu Lys Ile Arg Leu Lys Glu Ser Leu Arg Leu Ile Ser Lys Pro
        50                  55                  60

Leu Pro Gly Val Cys Gly Val Cys Ala Asp Gly Val Arg Pro Gly Glu
65                  70                  75                  80

Ala Pro Thr Arg Arg Gly Gln Gln Gln Arg His Ala Pro Ala Leu
                85                  90                  95

Arg Arg Cys Ser Trp Glu Pro Leu Leu Ala Leu Ala Ala Ala Ala Pro
            100                 105                 110

Ala Arg Asp Ser Ser Gly Ala Ala Arg Val Asp Gln Glu Leu Leu
        115                 120                 125
```

```
Ala Arg Arg Lys Asn Lys Val Gly Glu Thr Ala Leu His Gly Ala Val
        130                 135                 140

Arg Ala Gly His Ser Lys Val Val Glu Val Leu Met Lys Glu Asp Pro
145                 150                 155                 160

Gly Leu Ala Gly Val Asp Arg His Asp Gly Thr Ser Pro Leu Tyr Leu
                165                 170                 175

Ala Val Ser Leu Gly Arg Phe Glu Ile Ala Trp Asp Leu Leu Asp Met
            180                 185                 190

Ser Ser Arg Lys Leu Ser Tyr Ser Gly Pro Asp Gly Gln Asn Val Leu
        195                 200                 205

His Val Ala Val Gln His Pro Gln Asp Gln Leu Asn Pro Thr His Tyr
    210                 215                 220

Ile Phe Asn Asn Ala Gln His Arg
225                 230

<210> SEQ ID NO 11
<211> LENGTH: 2829
<212> TYPE: DNA
<213> ORGANISM: Oryza sativa

<400> SEQUENCE: 11
caagtacctg taaattgaaa cctgcagaca ctctggaagt aggcagattc acattgtgtc      60
agcggtcgcc ggtcggacga tgtccagggc aaacagtcga cagacaaagg cacaaagctg     120
tgaagggctg aatgctgaag ggatcgccgg cggcccagcg tggggtgaac ttgcagaggc     180
gccgtggagg gcgcagggcg atggaggcgg attggcggag actgccgccg gtagaggaga     240
ggagacgaga agactggaac tcggacggtc gcgtatgccc gacgattcga tcagaaactt     300
gtatacatgt atatggtata cctaatacat acctaggtct tctgggcccc tacttttcct     360
gggccctagg ccatcgcact tcttgccgta gcccagagcc ggccctgaaa agaggagat      420 acaagtgcac gtgagggaga gggagagggg agggattaca ttctgtttat aatctaatct     480
aatctaatgg tctaaaacaa tgagcccacc aatttaaatg aaaaaaattg agggctagat     540
gtttctaatc tattgaatg ccacttggtg gtttagaagc gtttacgaaa atgccacatt      600
ggcatgagaa cgcttgtagt atgtttaatg gacttgttca agataaagtg gtataattca     660
aatatcataa aatttggtgt tatatatgaa aaatgtcatg tttaagagtg ccatatgtta     720
attttggcag tgcagttgga tgctgaaagc cgacagagag aaaattaaat caaagatgac     780
cttttgttag ggatcgatgt ggaagaacat gactgtatta ctgtaataga agtttattaa     840
ataatcttaa catcttagag atatttcatt ctagagatct tatgtctcca gttggttgta     900
ggtagattgg acgtccagta tttctatgct aacatggccc tccgctattg caaggaaccc     960
taggaagatt gattaattta gttttctaaa tttgattttg gttccatttg cccttttgggc   1020 ttgcttaact gatggtatca cctgctgcag cactgtctgt actgttagag aagtgcaaga    1080
atgtcgaggt caatgtacag caagaagacc aacaaaggag tattcctctt ctcttgtacc    1140
tcactagtca aagtgacaaa aatgggagca ctcctcttca ctttgctgca tcgttgaaaa    1200
ctagtattga aggtttcaca tcgagattat gtgaacattt tcgcccgaaa caaagcccaa    1260
caacattgct tcttggactc aatgaatctg ctatatatca gccagacaac agaggatcat    1320
atcctatact tgttgctgcc tccaatggga tactcaaggt tgtcataacc ttgctcaaaa    1380
ggtatccaga ttgtgccact ttgcgtgaca tccaaggaag aactttcttc catgttgccg    1440
tggagaagaa gcggcgtaat atcgttgcat atgtgtgtga aaggccagga ttttctccta    1500
```

```
tcttgaatat gcaggacagc catgggata ctgctctaca ccttgctgtc aaagccggtg      1560 tttttttcaat tttcagctcg ttgttccgga ataggtaggt ttgcctgaat ttatcaaatg    1620
aggatggttt gacacctcgt gatctttcgt ggattatgat acctgcgagg ttgtactcta     1680
aaaaggtaat cgttctctgc cttttctgac cataattatc ccatataata cactacagag     1740
gccgagttta gttccaaact tattctttaa acttccagct tttccatcac atcgaaactt     1800
tcctacatac acaaactttc aacttttccg tcacatcgtt ccaatttcaa tcaaacttcc     1860
aattttagcg tgaactaaac acctagag ttgatgatac tatacctatt taactaggct       1920
accacatgtt aatctttcag aacccacgat atatgataag tcaactatta gcactttctg     1980
gaggtactgt tggttacagt cgccaggacc acttcttcga aaaatacagc aagaaaagag     2040
acgaagtaat cgattcaaac gatatgacaa gtgcggcaca ggttctcggc atttcttcag     2100
cgcttatagc aaccgtgaca tttgcagctg cattcacgtt gcctggaggt tacagagcag     2160
atgaccacac tgatggtggt acaccaacac ttgctgggag ctaccctttt gacgcgttca     2220
ttatctcgaa cagcctagca ttcatttgct ctttgctagc taccgtgagt ctgctctact     2280
ctgggataca atcgagggac atctccatcc ggcgcaggta ctacgcgttc tctatgctct     2340
tgatgcagag ttcaactacg agcttcactg ttgccttcgc catgggaatg tacctggtgc     2400
tagctcctgt tactcttaat gcagcagtgt ctgtctgcat catagcattt gtttctctgc     2460
tacctggaaa tatggaaatc ggggtatccc tagctatcgc aaaacattg aggattagat     2520 tgggaatttg ggcagcgatg tcccaagcaa ggccagttct cctgttcacg tggaaaagag     2580
tttggtcctg cataattatc tttggattgc ctggattgat gaagattcat agaaccaaaa    2640
tggcttgatt ggcgtgtcac cttttttcttgcattgatgt actttcttaa tatatccttt      2700
attcggagtg ttagaagtac atttacacaa catcgtgtat gacagctttg ctgttaccc     2760 tctgcattt aacgtagaat atacctacga tcttaggcag aagatgaaag agggaattc      2820 agagtgtgg                                                              2829
```

<210> SEQ ID NO 12
<211> LENGTH: 1389
<212> TYPE: DNA
<213> ORGANISM: Oryza sativa

<400> SEQUENCE: 12

```
atgtccaggg caaacagtcg acagacaaag gcacaaagct gtgaagggct gaatgctgaa      60
gggatcgccg gcggcccagc gtggggtgaa cttgcagagg cgccgtggag ggcgcagggc     120
gatggaggcg gattggcgga gactgccgcc gcactgtctg tactgttaga gaagtgcaag     180
aatgtcgagg tcaatgtaca gcaagaagac caacaaagga gtattcctct tctcttgtac     240
ctcactagtc aaagtgacaa aaatgggagc actcctcttc actttgctgc atcgttgaaa     300
actagtattg aaggtttcac atcgagatta tgtgaacatt ttcgcccgaa acaaagccca     360
acaacattgc ttcttggact caatgaatct gctatatatc agccagacaa cagaggatca     420
tatcctatac ttgttgctgc ctccaatggg atactcaagg ttgtcataac cttgctcaaa    480
aggtatccag attgtgccac tttgcgtgac atccaaggaa gaactttctt ccatgttgcc    540
gtggagaaga agcggcgtaa tatcgttgca tatgtgtgtg aaaggccagg attttctcct   600
atcttgaata tgcaggacag ccatggggat actgctctac accttgctgt caaagccggc    660
taccacatgt taatctttca gaacccacga tatatgataa gtcaactatt agcactttct    720
ggaggtactg ttggttacag tcgccaggac cacttcttcg aaaaatacag caagaaaaga    780
```

-continued

```
gacgaagtaa tcgattcaaa cgatatgaca agtgcggcac aggttctcgg catttcttca    840
gcgcttatag caaccgtgac atttgcagct gcattcacgt tgcctggagg ttacagagca    900
gatgaccaca ctgatggtgg tacaccaaca cttgctggga gctacccttt tgacgcgttc    960
attatctcga acagcctagc attcatttgc tctttgctag ctaccgtgag tctgctctac   1020
tctgggatac aatcgaggga catctccatc cggcgcaggt actacgcgtt ctctatgctc   1080
ttgatgcaga gttcaactac gagcttcact gttgccttcg ccatgggaat gtacctggtg   1140
ctagctcctg ttactcttaa tgcagcagtg tctgtctgca tcatagcatt tgtttctctg   1200
ctacctggaa atatggaaat cggggtatcc ctagctatcg caaacacatt gaggattaga   1260
ttgggaattt gggcagcgat gtcccaagca aggccagttc tcctgttcac gtggaaaaga   1320
gtttggtcct gcataattat ctttggattg cctggattga tgaagattca tagaaccaaa   1380
atggcttga                                                          1389
```

<210> SEQ ID NO 13
<211> LENGTH: 462
<212> TYPE: PRT
<213> ORGANISM: Oryza sativa

<400> SEQUENCE: 13

```
Met Ser Arg Ala Asn Ser Arg Gln Thr Lys Ala Gln Ser Cys Glu Gly
 1               5                  10                  15

Leu Asn Ala Glu Gly Ile Ala Gly Gly Pro Ala Trp Gly Glu Leu Ala
            20                  25                  30

Glu Ala Pro Trp Arg Ala Gln Gly Asp Gly Gly Leu Ala Glu Thr
        35                  40                  45

Ala Ala Ala Leu Ser Val Leu Leu Glu Lys Cys Lys Asn Val Glu Val
    50                  55                  60

Asn Val Gln Gln Glu Asp Gln Gln Arg Ser Ile Pro Leu Leu Leu Tyr
65                  70                  75                  80

Leu Thr Ser Gln Ser Asp Lys Asn Gly Ser Thr Pro Leu His Phe Ala
                85                  90                  95

Ala Ser Leu Lys Thr Ser Ile Glu Gly Phe Thr Ser Arg Leu Cys Glu
            100                 105                 110

His Phe Arg Pro Lys Gln Ser Pro Thr Thr Leu Leu Leu Gly Leu Asn
        115                 120                 125

Glu Ser Ala Ile Tyr Gln Pro Asp Asn Arg Gly Ser Tyr Pro Ile Leu
    130                 135                 140

Val Ala Ala Ser Asn Gly Ile Leu Lys Val Val Ile Thr Leu Leu Lys
145                 150                 155                 160

Arg Tyr Pro Asp Cys Ala Thr Leu Arg Asp Ile Gln Gly Arg Thr Phe
                165                 170                 175

Phe His Val Ala Val Glu Lys Lys Arg Arg Asn Ile Val Ala Tyr Val
            180                 185                 190

Cys Glu Arg Pro Gly Phe Ser Pro Ile Leu Asn Met Gln Asp Ser His
        195                 200                 205

Gly Asp Thr Ala Leu His Leu Ala Val Lys Ala Gly Tyr His Met Leu
    210                 215                 220

Ile Phe Gln Asn Pro Arg Tyr Met Ile Ser Gln Leu Leu Ala Leu Ser
225                 230                 235                 240

Gly Gly Thr Val Gly Tyr Ser Arg Gln Asp His Phe Phe Glu Lys Tyr
                245                 250                 255
```

Ser Lys Lys Arg Asp Glu Val Ile Asp Ser Asn Asp Met Thr Ser Ala
                260                 265                 270

Ala Gln Val Leu Gly Ile Ser Ser Ala Leu Ile Ala Thr Val Thr Phe
            275                 280                 285

Ala Ala Ala Phe Thr Leu Pro Gly Gly Tyr Arg Ala Asp Asp His Thr
        290                 295                 300

Asp Gly Gly Thr Pro Thr Leu Ala Gly Ser Tyr Pro Phe Asp Ala Phe
305                 310                 315                 320

Ile Ile Ser Asn Ser Leu Ala Phe Ile Cys Ser Leu Leu Ala Thr Val
                325                 330                 335

Ser Leu Leu Tyr Ser Gly Ile Gln Ser Arg Asp Ile Ser Ile Arg Arg
            340                 345                 350

Arg Tyr Tyr Ala Phe Ser Met Leu Leu Met Gln Ser Ser Thr Thr Ser
        355                 360                 365

Phe Thr Val Ala Phe Ala Met Gly Met Tyr Leu Val Leu Ala Pro Val
370                 375                 380

Thr Leu Asn Ala Ala Val Ser Val Cys Ile Ile Ala Phe Val Ser Leu
385                 390                 395                 400

Leu Pro Gly Asn Met Glu Ile Gly Val Ser Leu Ala Ile Ala Asn Thr
            405                 410                 415

Leu Arg Ile Arg Leu Gly Ile Trp Ala Ala Met Ser Gln Ala Arg Pro
        420                 425                 430

Val Leu Leu Phe Thr Trp Lys Arg Val Trp Ser Cys Ile Ile Ile Phe
            435                 440                 445

Gly Leu Pro Gly Leu Met Lys Ile His Arg Thr Lys Met Ala
    450                 455                 460

<210> SEQ ID NO 14
<211> LENGTH: 4979
<212> TYPE: DNA
<213> ORGANISM: Oryza sativa

<400> SEQUENCE: 14
ccctgtttag aactccatcc tatagatcga tcaaggtagt taagctagct tgcacagcga      60
tgaggcggcg atcgaggaga gaacgggacg tcggtcacca gcagcggtgg aggagcttgc     120
acgctggtgc tgctgctccg gggagtagag gccgtagcgg cgagtgtcgc cggcgtgggg     180 gcggcggcg cgcgggtggg aggtcgggga cgaacatggc ggtctagggt tttaattttg      240
ttttggaatg gggaatcgag aggttgacga cgtgggtgg ttggagttgg agtaggaggg      300
ggaacgcgag gtcgcgaaat atgggccggg ccgggcccat ctcctcctcc tatatggatt     360
ccgaatgggc cttccagaat acaaatggat ctggtggaag gcccagcaca gcaccaaaat     420
agaacacatt gaccttttt ttctctcttt ttggcaaaaa cattgacttt gttgagtta      480 tggagtacta tcatgttttg tcagatttta aattgggctc aaaatatttc aacttcgctc     540
aaaaagaaaa cggaacaggc tataggcata ggatggagcg tagtttggc cacaccgcaa      600 ctcccctctt taagttagat ttaggagtta aaactctact aaatgcactc ttaaattaga     660
ctttaatcgc acatatacgt actagcatat agtgcctagc tagctactcg aggtttggtt     720
tattttggga cgaatggcgt atatctagat ttataatact attatgtgtc acatttcgta     780
cgaggttgat ttattttaaa accatgggtg taatatgccc agtaaagcca ccacggctcg     840
cccataactc catattcttt atgaccggcc tctgctatga taaacataat ctagaggttc     900
acctcaagat ttggcttcat acagcatatc cgggcatttg agatactctc ttcggttttt    960

```
aatagatgac actattaact tttgaacaca tgtttgatta ttcgttttat ttaaaaattt    1020
tatacaaata tataagatac tctctccgtt ttagattata agttgtttta actttggtaa    1080
aggcaaatta gtttaaattt gaccaagttt gtagaaaaag ttaattaaat tttcatctca    1140
agaaaaaata ttatgaaaac atatttaata aaactaattt agtgttgtaa atattactat    1200
atttgtctac aaacttgatc aaacatgaag tagtttaagt ttaaccaaag tcaaaataac    1260
ttataatatg aaataaaggg agcataaatc atgcttaaat tactttgaat gataaaacaa    1320
ctcacaacaa aaaaaatata attacgtaaa ttttcttaaa taaaacgaat agtcaaacat    1380
gtgacaaaat aacaacgaca tcatctatta aaaaaaatac ttcagtacct ttatataatt    1440
atacaaaagt tttaaattag taaatgatca aatgatttac aaaaaatcta acatcaacgt    1500
ttattttaaa aggagtagta ctctatagta gagcaagttc gatagtatag ctaactgcta    1560
agtctaaatt atctatagtt aatttaatag ttaatatata tagtagttac ctacaaatat    1620
atacttatag tgtactgata catggtctga tacttggggc tcatagctag cgcgtgcgcg    1680
cggctagcaa gcacctcccc ttaagacttt aactacatct attaatttat tagttaatat    1740
ttaacactaa tgatactagt agtaattaga aaagattctg aagatttta agagattttt     1800 ttactaacag attgaaaatt taattttta agttagattt gaaaacttt gatttaagtt      1860 tcaaatttta aagtcaaatt ttgaaaactt tcaaaatcca gatttgaaaa atttgaaaac    1920
ttttaacttg agatttaaaa atttcaact cgagatttaa aaactttcaa cttaagattc     1980
gaaaactttc aagtctagat ttgaaaattt tgaaaacttt caacttgaga tttgaaaatt    2040
ttcaactcga gatttgaaaa cttcaactc gatattcgaa aactttcaag tccagatttg     2100
aaaattttga aaactttcaa ctaagattcg aaaattttca ctcgagaatt gaaattttca    2160
aggctagatt tgaaaatttt caagtcaata tttaaaaact ttcaactcaa acatttgaa     2220 aaagcacat ttgctattgg ctaggaaata gtggggatgg tggatgcatc gagtttgttg     2280
ctagagtaaa tatagtatga gagagttatt agcttttctt ggtcttagtg tacctatgaa    2340
atatatagat caatttggaa tggagggagt acttaggtgc agaaggaaat gatataactt    2400 ttcccccag attttctgtt acttcatgtt ttaggtatac caatattttt gtgtacttgg     2460
ttgatctgtg cactagcata taacaattat ccggccatca aaatggatga attttccatt    2520
tcatcatgtg aaagacataa taactggaac cttatcaaag acatatactt attagttatt    2580
gcatgaggta gttaacagaa ttgattgctt tcattcccca gctttcactg gtgatgaact    2640
tcaacttctt gtatataatc tttttgatgc tgcagttcat gtgatgtact gatttccttc    2700
tggtcattga attactatca tattgtattg ttttctttaa cggggaacag aaagggatac    2760
cctttctgaa atcatgctgc tgttattgaa ccctgtgttc cttattacag gtaaaagaca    2820
gcatgtcatg aggactttcc aaggtcataa ccccaacact atgaaagttc attctcgcaa    2880
gtctcaacct tcaaaaaaga agcctcgcga gttctatgac actgttgagg tacacattat    2940
tgatgatgac agtgatggtg atgcgaatat ccacaaggat tactcaatgg aagacacatc    3000
aaagcacctt gtcatgtaca atcctgagat cacgtatgac aaacaagggg aagttgaagt    3060
tactgagcct atagataact atacttcgct gaaccaaaga tacatgaagc caagacacgg    3120
atataacact gttttaccat ctatcggtgc ttacaccgtg caatgtgctc actgcttcaa    3180
atggaggatc atcccaacaa aagagaaata tgaagagata cgtgagaata tttgtcagga    3240
tgtgtttgta tgtgaaagag ctcgtgaatg gaaccgtgtt atatcttgcg ttgatcctga    3300
agatatatca caggatggaa gtagggtgtg ggcgattgac aaggcaagca tttcccagac    3360
```

```
tcctcctggc tgggatagag aggtcagaat cagaggagag ggttgcagca agtttgcaga       3420
tgtgtatgtc actgtttcct ttcctggatt tgcagtagta cgtgatattt ggtaccatat       3480
ttttggccgt ttccatattc ggatatcaaa cttctttctt tatgtgccta atagcatctt       3540
catgttaatc gtggcacact ggtcctgttt atttatgcct tgactagctg ctaactgcta       3600
agattagtta acactttcta ataattagt gcgatctcaa gtttattcat actagtacca        3660
cctatgatca tgaaacttct acagttttca gttaatactt tgtaacacca tagcaaatat       3720
ctcactaatt ccttatgata tgcctgcttg aataatgcaa acagccatta ttatgtttgc       3780
cagtttcctc aggaactttt tcattatatg atatttcgaa cagcaacatt gcttgtagga       3840
cacacaagat actcgaggtt gacatatgtg aaatactttt ctttttttcct tcaggtacta      3900 cacttctcca actgggaaga agttgaggtc attggtagaa gttgggaggt gggattcatc       3960
catttgtgct ctttttgttg catattttgt gtggctagtg tattacttgg ggtacctagt       4020
tctagttggt ctggtacaac aaaacgaagc tctggaaaag ctctggaaag ttcttgaaat       4080
atttcccagg aaatgatgta attattatgt ccatattcta ggtacttggc agagaaccca       4140
cactacatta ggcaaggggt taacttaacc cagttctctt tcgccacccc caagcctctg       4200
caagaagact atgtcaggaa gcatacatat gcagcaactc ctgaattacc agagcttctt       4260
gagactgcgc aaggtgtgtt atcagtccta ggtttgttac atctattcta cttttttttc       4320 attttttaact tcttgttccc cacattgttg gaaaggaggc gtgcttcaaa caaggtaagt       4380
tgctgcgcaa atggcacagt tggaggtatc tttgcaatgc aagcatgtct agttattttc       4440
agtcaaatga gctgtgagaa gtcatgtact catgatgccc ttgcattttg ctactttaca       4500
tcctttcttg atcttagcac catctaaata tcatttagtg ttgtgatatt aactgaatat       4560
attttccccc agtttcatcc catagctata tcctgtcaaa actacctgtt cttgggagct       4620
tttgctgata tatttgttat tgagtataca ttgttatttt tcagtggatc cactctgctg       4680
ggcagcaccc cctacacgca gcgaactgct tggtgagctt ggtgcttcaa cctcaagatc       4740
tgttgatgtc agccagtctg aggtgtcata ccctgtagac ttgcaccagc ccgaggagtc       4800
tgcgccacta cctccacgca caaagaagaa aactatgaaa cgagggcgag tgtcagcaac       4860
ggggtctcaa tcgactccac ctggttcatc caaagatcag tctggaggat gcgtaagcga       4920
cgtcgagttt gttcgctgt gaactctgga tgcagtgcct ttgtctctgt cagtctgcc        4979
```

<210> SEQ ID NO 15
<211> LENGTH: 1233
<212> TYPE: DNA
<213> ORGANISM: Oryza sativa

<400> SEQUENCE: 15

```
atgaggcggc gatcgaggag agaacgggac gtcggtcacc agcagcggtg gaggagcttg        60
cacgctggtg ctgctgctcc ggggagtaga ggccgtagcg gcgagtgtcg ccggcgtggg       120
ggcggcggcg gcgcgggtaa aagacagcat gtcatgagga cttccaagg tcataacccc        180 aacactatga agttcattc tcgcaagtct caaccttcaa aaaagaagcc tcgcgagttc       240
tatgacactg ttgaggtaca cattattgat gatgacagta tggtgatgc gaatatccac        300 aaggattact caatggaaga cacatcaaag caccttgtca tgtacaatcc tgagatcacg       360
tatgacaaac aaggggaagt tgaagttact gagcctatag ataactatac ttcgctgaac       420
caaagataca tgaagccaag acacggatat aacactgttt taccatctat cggtgcttac       480
```

-continued

```
accgtgcaat gtgctcactg cttcaaatgg aggatcatcc caacaaaaga gaaatatgaa      540
gagatacgtg agaatatttg tcaggatgtg tttgtatgtg aaagagctcg tgaatggaac      600
cgtgttatat cttgcgttga tcctgaagat atatcacagg atggaagtag ggtgtgggcg      660
attgacaagg caagcatttc ccagactcct cctggctggg atagagaggt cagaatcaga      720
ggagagggtt gcagcaagtt tgcagatgtg tactacactt ctccaactgg gaagaagttg      780
aggtcattgg tagaagttgg gaggtacttg gcagagaacc cacactacat taggcaaggg      840
gttaacttaa cccagttctc tttcgccacc cccaagcctc tgcaagaaga ctatgtcagg      900
aagcatacat atgcagcaac tcctgaatta ccagagcttc ttgagactgc gcaagtggat      960
ccactctgct gggcagcacc ccctacacgc agcgaactgc ttggtgagct tggtgcttca     1020
acctcaagat ctgttgatgt cagccagtct gaggtgtcat accctgtaga cttgcaccag     1080
cccgaggagt ctgcgccact acctccacgc acaaagaaga aaactatgaa acgagggcga     1140
gtgtcagcaa cggggtctca atcgactcca cctggttcat ccaaagatca gtctggagga     1200
tgcgtaagcg acgtcgagtt tgtttcgctg tga                                  1233
```

<210> SEQ ID NO 16
<211> LENGTH: 410
<212> TYPE: PRT
<213> ORGANISM: Oryza sativa

<400> SEQUENCE: 16

Met Arg Arg Arg Ser Arg Arg Glu Arg Asp Val Gly His Gln Gln Arg
1               5                   10                  15

Trp Arg Ser Leu His Ala Gly Ala Ala Pro Gly Ser Arg Gly Arg
            20                  25                  30

Ser Gly Glu Cys Arg Arg Gly Gly Gly Gly Ala Gly Lys Arg
        35                  40                  45

Gln His Val Met Arg Thr Phe Gln Gly His Asn Pro Asn Thr Met Lys
    50                  55                  60

Val His Ser Arg Lys Ser Gln Pro Ser Lys Lys Pro Arg Glu Phe
65                  70                  75                  80

Tyr Asp Thr Val Glu Val His Ile Ile Asp Asp Ser Asp Gly Asp
                85                  90                  95

Ala Asn Ile His Lys Asp Tyr Ser Met Glu Asp Thr Ser Lys His Leu
            100                 105                 110

Val Met Tyr Asn Pro Glu Ile Thr Tyr Asp Lys Gln Gly Glu Val Glu
        115                 120                 125

Val Thr Glu Pro Ile Asp Asn Tyr Thr Ser Leu Asn Gln Arg Tyr Met
    130                 135                 140

Lys Pro Arg His Gly Tyr Asn Thr Val Leu Pro Ser Ile Gly Ala Tyr
145                 150                 155                 160

Thr Val Gln Cys Ala His Cys Phe Lys Trp Arg Ile Ile Pro Thr Lys
                165                 170                 175

Glu Lys Tyr Glu Glu Ile Arg Glu Asn Ile Cys Gln Asp Val Phe Val
            180                 185                 190

Cys Glu Arg Ala Arg Glu Trp Asn Arg Val Ile Ser Cys Val Asp Pro
        195                 200                 205

Glu Asp Ile Ser Gln Asp Gly Ser Arg Val Trp Ala Ile Asp Lys Ala
    210                 215                 220

Ser Ile Ser Gln Thr Pro Pro Gly Trp Asp Arg Glu Val Arg Ile Arg
225                 230                 235                 240

```
Gly Glu Gly Cys Ser Lys Phe Ala Asp Val Tyr Tyr Thr Ser Pro Thr
                245                 250                 255
Gly Lys Lys Leu Arg Ser Leu Val Glu Val Gly Arg Tyr Leu Ala Glu
            260                 265                 270
Asn Pro His Tyr Ile Arg Gln Gly Val Asn Leu Thr Gln Phe Ser Phe
        275                 280                 285
Ala Thr Pro Lys Pro Leu Gln Glu Asp Tyr Val Arg Lys His Thr Tyr
    290                 295                 300
Ala Ala Thr Pro Glu Leu Pro Glu Leu Leu Glu Thr Ala Gln Val Asp
305                 310                 315                 320
Pro Leu Cys Trp Ala Ala Pro Pro Thr Arg Ser Glu Leu Leu Gly Glu
                325                 330                 335
Leu Gly Ala Ser Thr Ser Arg Ser Val Asp Val Ser Gln Ser Glu Val
            340                 345                 350
Ser Tyr Pro Val Asp Leu His Gln Pro Glu Glu Ser Ala Pro Leu Pro
        355                 360                 365
Pro Arg Thr Lys Lys Thr Met Lys Arg Gly Arg Val Ser Ala Thr
    370                 375                 380
Gly Ser Gln Ser Thr Pro Pro Gly Ser Ser Lys Asp Gln Ser Gly Gly
385                 390                 395                 400
Cys Val Ser Asp Val Glu Phe Val Ser Leu
                405                 410

<210> SEQ ID NO 17
<211> LENGTH: 2044
<212> TYPE: DNA
<213> ORGANISM: Oryza sativa

<400> SEQUENCE: 17
gaagtagtac taaaatggat ctcgcacact ttctctttcc gtatagccaa gctgtgctgc      60
aaagatcact gatcagagtg aacctggtac attttcacgg gctggttcat tttgtaggac     120
tgtctgcttg gcttggcctg tgcaatccag tgatcagcag tactgtactc cactatagta     180
atcagagcat gtgcgccagt ttctccctta tgttgctact ctaatacatt tgggattaac     240
taattatggt cactaatcag ctattgacag tagcaattgg ccggcttggc caaatatgca     300
agtgagttgg gctgttactt tgccttcttt ttcacaaagg aaaatgttac tgtcaagata     360
tactgggtaa gatgaatgat taaaagttaa ggtagtacat tgtatgcgct ctcttttttt     420
ttaaccggtt ctggcaatga gaccactatg ttcttttgc tatgtcaaaa cacctaattt     480
aaatcatatt agttttgaat cctcatcttt ttgttatagg aattcaaaat ctgtaggagt     540
ctcctgtgat ttttgtccac agttttgtc agagttagag gtagagacgg aactctttca     600
cttcgtgtca tgattcctac gcgacagcga gaccgtatca gatgctccca caacattacg     660
caatagtgtc ctgcaggtct tgactctcga gatttagatt ttgggatgtg cctatatgct     720
ccgaaaaaaa aaacttgcac gaaagttaaa gataatcagc ggctgtgatt agaagcgaga     780
ttagcactta attatcatta gcgaggggta atttcgtcaa gattttcgag cccatatcca     840
gcccagtcca tctgaagcga tccccacccc caccggtcca ccacggcgcc gctcctcaac     900
cgcaccgcca cgccgcctcc actccctcct ccctctcct ctccgccgct gctccgctca     960
atgccgcctt gccgcccag cgctccgctc tcttcttccc ctaggctgac cgctcagccc    1020
agcgccgccc ggcttgctgc ctctccatcc tcttcgcccc ctcgtctcgc cgcttccccg    1080
cccctgcgcc gtgcagcccg gcgcacccccc ttcatccatc tcacatgcgt agtttgcttg    1140
```

```
atgagtggtt tgctccatgt tagaagcttg gtattgcagc agaacatggc tattttgtca   1200
ggtaaacatt ttgagtacct tttttcttc ttaaatctgt ttttatttgc attttctcca    1260
cacactatta tgcaattgta cagttgaatt attcaggagt ataatgaact gtttatgttc   1320
tctcagatgg aacaaagcag ctgaatggga atcaagctat ccaaaccatg attttgagtg   1380
gaagcacatc gctgaaccga tcatgcaagt ttacaccgaa acaattgatg ggtcctccat   1440
agagccaaag gaaagtgctc tattatggca ttatctggat gcagaccatg acttcggttc   1500
ctgccaagca aaggaactac tgggtcatct tgaaagggtg ctatcaaatg aacctgttgt   1560
tgtgaagtgt ggtcattaca ttgtagaagt caaaccacag gtctatacca tttgaattta   1620
ttactacatt ttttcacttt caactcatta tgtccagctc acactaaatg aaatacatta   1680
cttgtgcagg gagttagcaa gggtcttgtt gtggacaagg taattcacag attgatgaac   1740
aacgggaaga cgctggattt cgtagtgtgc atcggtaacg atcgatctga tgaggacatg   1800
ttcaaaagca tcgacagcat gacctccagc tctgcattcc ctgcagttcc agaggtcttt   1860
gcctgttcag ttggtcagaa acccagcaaa gcaaaatact atgtcgacaa tgttggtgaa   1920
gtagtaagat tgctcaagaa tgtagccggc atttcgtcgc accgggaggc cgtcagccat   1980
ggacgtgtga tcttcaggga tgtgatcgat tatgtggact gaaccaccta atctttgtaa   2040
catc                                                                2044
```

<210> SEQ ID NO 18
<211> LENGTH: 819
<212> TYPE: DNA
<213> ORGANISM: Oryza sativa

<400> SEQUENCE: 18

```
atggatctcg cacactttct ctttccgtat agccaagctg tgctgcaaag atcactgatc     60
agagtgaacc tgctattgac agtagcaatt ggccggcttg ccaaatatg caagaattca    120
aaatctgtag gagtctcctg tgattttgt ccacagtttt tgtcagagtt agagaagctt    180
ggtattgcag cagaacatgg ctattttgtc agatggaaca aagcagctga atgggaatca    240
agctatccaa accatgattt tgagtggaag cacatcgctg aaccgatcat gcaagtttac    300
accgaaacaa ttgatgggtc ctccatagag ccaaaggaaa gtgctctatt atggcattat    360
ctggatgcag accatgactt cggttcctgc caagcaaagg aactactggg tcatcttgaa    420
agggtgctat caaatgaacc tgttgttgtg aagtgtggtc attacattgt agaagtcaaa    480
ccacagggag ttagcaaggg tcttgttgtg acaaggtaa ttcacagatt gatgaacaac     540
gggaagacgc tggatttcgt agtgtgcatc ggtaacgatc gatctgatga ggacatgttc    600
aaaagcatcg acagcatgac ctccagctct gcattccctg cagttccaga ggtctttgcc    660
tgttcagttg gtcagaaacc cagcaaagca aaatactatg tcgacaatgt tggtgaagta    720
gtaagattgc tcaagaatgt agccggcatt tcgtcgcacc gggaggccgt cagccatgga    780
cgtgtgatct tcagggatgt gatcgattat gtggactga                           819
```

<210> SEQ ID NO 19
<211> LENGTH: 272
<212> TYPE: PRT
<213> ORGANISM: Oryza sativa

<400> SEQUENCE: 19

```
Met Asp Leu Ala His Phe Leu Phe Pro Tyr Ser Gln Ala Val Leu Gln
1               5                   10                  15
```

Arg Ser Leu Ile Arg Val Asn Leu Leu Thr Val Ala Ile Gly Arg
            20                  25                  30

Leu Gly Gln Ile Cys Lys Asn Ser Lys Ser Val Gly Val Ser Cys Asp
        35                  40                  45

Phe Cys Pro Gln Phe Leu Ser Glu Leu Glu Lys Leu Gly Ile Ala Ala
    50                  55                  60

Glu His Gly Tyr Phe Val Arg Trp Asn Lys Ala Ala Glu Trp Glu Ser
65                  70                  75                  80

Ser Tyr Pro Asn His Asp Phe Glu Trp Lys His Ile Ala Glu Pro Ile
                85                  90                  95

Met Gln Val Tyr Thr Glu Thr Ile Asp Gly Ser Ser Ile Glu Pro Lys
            100                 105                 110

Glu Ser Ala Leu Leu Trp His Tyr Leu Asp Ala Asp His Asp Phe Gly
        115                 120                 125

Ser Cys Gln Ala Lys Glu Leu Leu Gly His Leu Glu Arg Val Leu Ser
    130                 135                 140

Asn Glu Pro Val Val Lys Cys Gly His Tyr Ile Val Glu Val Lys
145                 150                 155                 160

Pro Gln Gly Val Ser Lys Gly Leu Val Val Asp Lys Val Ile His Arg
                165                 170                 175

Leu Met Asn Asn Gly Lys Thr Leu Asp Phe Val Val Cys Ile Gly Asn
            180                 185                 190

Asp Arg Ser Asp Glu Asp Met Phe Lys Ser Ile Asp Ser Met Thr Ser
        195                 200                 205

Ser Ser Ala Phe Pro Ala Val Pro Glu Val Phe Ala Cys Ser Val Gly
    210                 215                 220

Gln Lys Pro Ser Lys Ala Lys Tyr Tyr Val Asp Asn Val Gly Glu Val
225                 230                 235                 240

Val Arg Leu Leu Lys Asn Val Ala Gly Ile Ser Ser His Arg Glu Ala
                245                 250                 255

Val Ser His Gly Arg Val Ile Phe Arg Asp Val Ile Asp Tyr Val Asp
            260                 265                 270

<210> SEQ ID NO 20
<211> LENGTH: 1481
<212> TYPE: DNA
<213> ORGANISM: Oryza sativa

<400> SEQUENCE: 20
catgaactcg ctccaatcct tcctcgccct caacccgccc gccgccgccg ccgccctcgg      60
cggcgcgcgc ctccgcccgt cgcgcgtcac cgcgtgcctc gccacgccca cgcccacgcc     120 gccgccccg acctccgcgc ccctcgcccc gccgccgcg gccgcgcgcc gcgagctgtc      180
cgccgcgagc cgcgccgtgg tggaggacga ggcgaggtac atcgtcggga cgtacaaccg     240
ctcccgcgtc gtcctcgtcg ccggccgcgg ctgcaagctg tacgacgccg acgggcgcga     300
gtacctcgac atggccgccg gcatcgccgt caacgcgctc ggccacgccg accccgactg     360
ggtcgccgcc gtctccgccc aggccgccac cctcgtccac gccagcaacg tccagtacac     420
cgtcccccag gtggcgctcg ccaagcgcct cgtggaggcc tccttcgcgg accgcgtctt     480
cttcgccaac accggcacgg aggccaacga ggcggccatc aagttcgcca ggaagttcca     540
gagggtggcg cgccccgacg cgacgcgcgc caccgagttc atgtcgttca ccaactgctt     600
ccatggcagg accatggggt cgctcgcgct caccagcaag gtccaatacc gggagccatt     660
cgcgccggtg atgcccggcg cgacgttcgc cgagtacggg aacctagagg aggccaagaa     720

```
ggtgatacag tctggcaaaa ttgctgccgt gttcgtcgag cccgtgcagg gcgagggtgg    780
gatccatagt gccaccaagg agttcttgca ggggctgcgg gatgcctgcg atgaggctgg    840
agctctcttg gtctttgatg aggtgcaatg tggtctggga cgcacaggtt acctctgggc    900
gtatgaagcc tatggagtac tacctgacat tatgaccttg gcaaagccat ggccggtgg     960
tctccccatt ggtgtagtct tggtcaccga gaaggttgct tcagcaataa acttcggcga   1020
ccacggtacc acattcgggg gaggccctct tgtttgccaa gctgcattga ccacattgga   1080
taagatccag aaacctggct cctagcaga ggtggccaag aaggagaga acttcaagca     1140
gcttctcagt accaagctga gcggaaacgc ccatgtgaaa gagatccggg ggatcggtct   1200
cattgtcggc atcgagctcg atgtcccagc gggtcctttg gttgatgcgt gcttggatcg   1260
cggtgtcata gtgctgacag ctggtaaagg caatgttgtg aggctggtgc cgccactcat   1320
catctcggaa aaggagcttg agcaggctgc agaggtgata agggactgtc tacctgcact   1380
tgatgcctct acctcttaat gtaagcaaca tccttagcaa tggaggctag aatgatcttc   1440
ccctttggg aagacccta gcaatggatg ttagaatgaa c                        1481
```

<210> SEQ ID NO 21
<211> LENGTH: 1398
<212> TYPE: DNA
<213> ORGANISM: Oryza sativa

<400> SEQUENCE: 21

```
atgaactcgc tccaatcctt cctcgccctc aacccgcccg ccgccgccgc cgccctcggc     60
ggcgcgcgcc tccgcccgtc gcgcgtcacc gcgtgcctcg ccacgcccac gcccacgccg    120
ccgccccga cctccgcgcc cctcgcccc ccgccgcgg ccgcgcgccg cgagctgtcc       180
gccgcgagcc gcgccgtggt ggaggacgag gcgaggtaca tcgtcgggac gtacaaccgc    240
tcccgcgtcg tcctcgtcgc cggccgcggc tgcaagctgt acgacgccga cgggcgcgag    300
tacctcgaca tggccgccgg catcgccgtc aacgcgctcg ccacgccga ccccgactgg     360
gtcgccgccg tctccgccca ggccgccacc ctcgtccacg ccagcaacgt ccagtacacc    420
gtcccccagg tggcgctcgc caagcgcctc gtggaggcct ccttcgcgga ccgcgtcttc    480
ttcgccaaca ccggcacgga ggccaacgag gcggccatca agttcgccag gaagttccag    540
agggtggcgc gccccgacgg cgacgcgccc accgagttca tgtcgttcac caactgcttc    600
catggcagga ccatggggtc gctcgcgctc accagcaagg tccaataccg ggagccattc    660
gcgccggtga tgcccggcgc gacgttcgcc gagtacggga acctagagga ggccaagaag    720
gtgatacagt ctggcaaaat tgctgccgtg ttcgtcgagc ccgtgcaggg cgagggtggg    780
atccatagtg ccaccaagga gttcttgcag gggctgcggg atgcctgcga tgaggctgga    840
gctctcttgg tctttgatga ggtgcaatgt ggtctgggac gcacaggtta cctctgggcg    900
tatgaagcct atggagtact acctgacatt atgaccttgg caaagccatt ggccggtggt    960
ctccccattg gtgtagtctt ggtcaccgag aaggttgctt cagcaataaa cttcggcgac   1020
cacggtacca cattcggggg aggccctctt gtttgccaag ctgcattgac cacattggat   1080
aagatccaga aacctggctt cctagcagag gtggccaaga aggagagaa cttcaagcag    1140
cttctcagta ccaagctgag cggaaacgcc catgtgaaag agatccgggg gatcggtctc   1200
attgtcggca tcgagctcga tgtcccagcg ggtcctttgg ttgatgcgtg cttggatcgc   1260
ggtgtcatag tgctgacagc tggtaaaggc aatgttgtga ggctggtgcc gccactcatc   1320
```

```
atctcggaaa aggagcttga gcaggctgca gaggtgataa gggactgtct acctgcactt    1380
gatgcctcta cctcttaa                                                  1398
```

<210> SEQ ID NO 22
<211> LENGTH: 465
<212> TYPE: PRT
<213> ORGANISM: Oryza sativa

<400> SEQUENCE: 22

```
Met Asn Ser Leu Gln Ser Phe Leu Ala Leu Asn Pro Pro Ala Ala Ala
1               5                   10                  15

Ala Ala Leu Gly Gly Ala Arg Leu Arg Pro Ser Arg Val Thr Ala Cys
            20                  25                  30

Leu Ala Thr Pro Thr Pro Thr Pro Pro Pro Pro Thr Ser Ala Pro Leu
        35                  40                  45

Ala Pro Ala Ala Ala Ala Arg Arg Glu Leu Ser Ala Ala Ser Arg
    50                  55                  60

Ala Val Val Glu Asp Glu Ala Arg Tyr Ile Val Gly Thr Tyr Asn Arg
65                  70                  75                  80

Ser Arg Val Val Leu Val Ala Gly Arg Gly Cys Lys Leu Tyr Asp Ala
                85                  90                  95

Asp Gly Arg Glu Tyr Leu Asp Met Ala Ala Gly Ile Ala Val Asn Ala
            100                 105                 110

Leu Gly His Ala Asp Pro Asp Trp Val Ala Ala Val Ser Ala Gln Ala
        115                 120                 125

Ala Thr Leu Val His Ala Ser Asn Val Gln Tyr Thr Val Pro Gln Val
    130                 135                 140

Ala Leu Ala Lys Arg Leu Val Glu Ala Ser Phe Ala Asp Arg Val Phe
145                 150                 155                 160

Phe Ala Asn Thr Gly Thr Glu Ala Asn Glu Ala Ala Ile Lys Phe Ala
                165                 170                 175

Arg Lys Phe Gln Arg Val Ala Arg Pro Asp Gly Asp Ala Pro Thr Glu
            180                 185                 190

Phe Met Ser Phe Thr Asn Cys Phe His Gly Arg Thr Met Gly Ser Leu
        195                 200                 205

Ala Leu Thr Ser Lys Val Gln Tyr Arg Glu Pro Phe Ala Pro Val Met
    210                 215                 220

Pro Gly Ala Thr Phe Ala Glu Tyr Gly Asn Leu Glu Glu Ala Lys Lys
225                 230                 235                 240

Val Ile Gln Ser Gly Lys Ile Ala Ala Val Phe Val Glu Pro Val Gln
                245                 250                 255

Gly Glu Gly Gly Ile His Ser Ala Thr Lys Glu Phe Leu Gln Gly Leu
            260                 265                 270

Arg Asp Ala Cys Asp Glu Ala Gly Ala Leu Leu Val Phe Asp Glu Val
        275                 280                 285

Gln Cys Gly Leu Gly Arg Thr Gly Tyr Leu Trp Ala Tyr Glu Ala Tyr
    290                 295                 300

Gly Val Leu Pro Asp Ile Met Thr Leu Ala Lys Pro Leu Ala Gly Gly
305                 310                 315                 320

Leu Pro Ile Gly Val Val Leu Val Thr Glu Lys Val Ala Ser Ala Ile
                325                 330                 335

Asn Phe Gly Asp His Gly Thr Thr Phe Gly Gly Gly Pro Leu Val Cys
            340                 345                 350

Gln Ala Ala Leu Thr Thr Leu Asp Lys Ile Gln Lys Pro Gly Phe Leu
```

```
                355              360              365
Ala Glu Val Ala Lys Lys Gly Glu Asn Phe Lys Gln Leu Leu Ser Thr
        370              375              380

Lys Leu Ser Gly Asn Ala His Val Lys Glu Ile Arg Gly Ile Gly Leu
385              390              395              400

Ile Val Gly Ile Glu Leu Asp Val Pro Ala Gly Pro Leu Val Asp Ala
                405              410              415

Cys Leu Asp Arg Gly Val Ile Val Leu Thr Ala Gly Lys Gly Asn Val
            420              425              430

Val Arg Leu Val Pro Pro Leu Ile Ile Ser Glu Lys Glu Leu Glu Gln
        435              440              445

Ala Ala Glu Val Ile Arg Asp Cys Leu Pro Ala Leu Asp Ala Ser Thr
    450              455              460

Ser
465

<210> SEQ ID NO 23
<211> LENGTH: 413
<212> TYPE: DNA
<213> ORGANISM: Oryza sativa

<400> SEQUENCE: 23
gcgaaaatct tatcattgta gttctttcca tcgcagaggg tgggctaggg cgatccgggg      60
ggcgcgacca tggcttacgt cgagagaggt gttgtgaaag acaaacggac aatttggcgg     120
ctaagcataa tttctgactt cttcagggct attgtgaact tcatcagaat gttcttcctt     180
acaatgttct cgattgaaaa aacagacagc tataggaaag ggtatggctc tggtaagaaa     240
tgggatggtg ggcctggtgg gggaggtcct ggtggtggcc cttatggggg cggccgcggc     300
ggtggaggcg gcctccgagg tcctcgcaca ctatctgaca tccgatctaa cgatcagaat     360
tctctccctg cttgtggatc ctgctgcggt taacctgtac atctgtcatt gtg            413

<210> SEQ ID NO 24
<211> LENGTH: 324
<212> TYPE: DNA
<213> ORGANISM: Oryza sativa

<400> SEQUENCE: 24
atggcttacg tcgagagagg tgttgtgaaa gacaaacgga caatttggcg gctaagcata      60
atttctgact tcttcagggc tattgtgaac ttcatcagaa tgttcttcct tacaatgttc     120
tcgattgaaa aaacagacag ctataggaaa gggtatggct ctggtaagaa atgggatggt     180
gggcctggtg ggggaggtcc tggtggtggc ccttatgggg gcggccgcgg cggtggaggc     240
ggcctccgag gtcctcgcac actatctgac atccgatcta acgatcagaa ttctctccct     300
gcttgtggat cctgctgcgg ttaa                                            324

<210> SEQ ID NO 25
<211> LENGTH: 107
<212> TYPE: PRT
<213> ORGANISM: Oryza sativa

<400> SEQUENCE: 25

Met Ala Tyr Val Glu Arg Gly Val Val Lys Asp Lys Arg Thr Ile Trp
1               5                   10                  15

Arg Leu Ser Ile Ile Ser Asp Phe Phe Arg Ala Ile Val Asn Phe Ile
            20                  25                  30
```

```
Arg Met Phe Phe Leu Thr Met Phe Ser Ile Glu Lys Thr Asp Ser Tyr
            35                  40                  45

Arg Lys Gly Tyr Gly Ser Gly Lys Lys Trp Asp Gly Gly Pro Gly Gly
 50                  55                  60

Gly Gly Pro Gly Gly Gly Pro Tyr Gly Gly Gly Arg Gly Gly Gly Gly
 65                  70                  75                  80

Gly Leu Arg Gly Pro Arg Thr Leu Ser Asp Ile Arg Ser Asn Asp Gln
                85                  90                  95

Asn Ser Leu Pro Ala Cys Gly Ser Cys Cys Gly
            100                 105

<210> SEQ ID NO 26
<211> LENGTH: 23
<212> TYPE: DNA
<213> ORGANISM: Artificial Sequence
<220> FEATURE:
<223> OTHER INFORMATION: Forward primer for cloning cDNA of OsICDH1 gene

<400> SEQUENCE: 26
gactccgacg accagaagct acc                                              23

<210> SEQ ID NO 27
<211> LENGTH: 21
<212> TYPE: DNA
<213> ORGANISM: Artificial Sequence
<220> FEATURE:
<223> OTHER INFORMATION: Reverse primer for cloning cDNA of OsICDH1 gene

<400> SEQUENCE: 27
ctaacatgtc ccctgccgtt g                                                21

<210> SEQ ID NO 28
<211> LENGTH: 26
<212> TYPE: DNA
<213> ORGANISM: Artificial Sequence
<220> FEATURE:
<223> OTHER INFORMATION: Forward primer for cloning gDNA of OsMtN3L gene

<400> SEQUENCE: 28
cactgacatg tggccttcct tcttcc                                           26

<210> SEQ ID NO 29
<211> LENGTH: 27
<212> TYPE: DNA
<213> ORGANISM: Artificial Sequence
<220> FEATURE:
<223> OTHER INFORMATION: Reverse primer for cloning gDNA of OsMtN3L gene

<400> SEQUENCE: 29
ctaagacaaa attaggtgca ggatggg                                          27

<210> SEQ ID NO 30
<211> LENGTH: 29
<212> TYPE: DNA
<213> ORGANISM: Artificial Sequence
<220> FEATURE:
<223> OTHER INFORMATION: Forward primer for cloning gDNA of OsDN-DTP6
      gene

<400> SEQUENCE: 30
gctgcaaagg aggaagagaa agagtgttg                                        29

<210> SEQ ID NO 31
<211> LENGTH: 27
```

```
<212> TYPE: DNA
<213> ORGANISM: Artificial Sequence
<220> FEATURE:
<223> OTHER INFORMATION: Reverse primer for cloning gDNA of OsDN-DTP6
      gene

<400> SEQUENCE: 31
gagatcgcaa caaacccata cccaaac                                      27

<210> SEQ ID NO 32
<211> LENGTH: 27
<212> TYPE: DNA
<213> ORGANISM: Artificial Sequence
<220> FEATURE:
<223> OTHER INFORMATION: Forward primer for cloning gDNA of OsANKL1 gene

<400> SEQUENCE: 32
caagtacctg taaattgaaa cctgcag                                      27

<210> SEQ ID NO 33
<211> LENGTH: 24
<212> TYPE: DNA
<213> ORGANISM: Artificial Sequence
<220> FEATURE:
<223> OTHER INFORMATION: Reverse primer for cloning gDNA of OsANKL1 gene

<400> SEQUENCE: 33
ccacactctg aattcccctc tttc                                         24

<210> SEQ ID NO 34
<211> LENGTH: 29
<212> TYPE: DNA
<213> ORGANISM: Artificial Sequence
<220> FEATURE:
<223> OTHER INFORMATION: Forward primer for cloning gDNA of OsMBD2 gene

<400> SEQUENCE: 34
ccctgtttag aactccatcc tatagatcg                                    29

<210> SEQ ID NO 35
<211> LENGTH: 25
<212> TYPE: DNA
<213> ORGANISM: Artificial Sequence
<220> FEATURE:
<223> OTHER INFORMATION: Reverse primer for cloning gDNA of OsMBD2 gene

<400> SEQUENCE: 35
ggcagactga cagagacaaa ggcac                                        25

<210> SEQ ID NO 36
<211> LENGTH: 29
<212> TYPE: DNA
<213> ORGANISM: Artificial Sequence
<220> FEATURE:
<223> OTHER INFORMATION: Forward primer for cloning gDNA of OsTP1 gene

<400> SEQUENCE: 36
gaagtagtac taaaatggat ctcgcacac                                    29

<210> SEQ ID NO 37
<211> LENGTH: 28
<212> TYPE: DNA
<213> ORGANISM: Artificial Sequence
<220> FEATURE:
<223> OTHER INFORMATION: Reverse primer for cloning gDNA of OsTP1 gene

<400> SEQUENCE: 37
```
gatgttacaa agattaggtg gttcagtc                28

<210> SEQ ID NO 38
<211> LENGTH: 25
<212> TYPE: DNA
<213> ORGANISM: Artificial Sequence
<220> FEATURE:
<223> OTHER INFORMATION: Forward primer for cloning cDNA of OsACOAT1 gene

<400> SEQUENCE: 38
catgaactcg ctccaatcct tcctc                25

<210> SEQ ID NO 39
<211> LENGTH: 27
<212> TYPE: DNA
<213> ORGANISM: Artificial Sequence
<220> FEATURE:
<223> OTHER INFORMATION: Reverse primer for cloning cDNA of OsACOAT1 gene

<400> SEQUENCE: 39
gttcattcta acatccattg ctaaggg                27

<210> SEQ ID NO 40
<211> LENGTH: 29
<212> TYPE: DNA
<213> ORGANISM: Artificial Sequence
<220> FEATURE:
<223> OTHER INFORMATION: Forward primer for cloning cDNA of OsDN-DTP7 gene

<400> SEQUENCE: 40
gcgaaaatct tatcattgta gttctttcc                29

<210> SEQ ID NO 41
<211> LENGTH: 26
<212> TYPE: DNA
<213> ORGANISM: Artificial Sequence
<220> FEATURE:
<223> OTHER INFORMATION: Reverse primer for cloning cDNA of OsDN-DTP7 gene

<400> SEQUENCE: 41
cacaatgaca gatgtacagg ttaacc                26

<210> SEQ ID NO 42
<211> LENGTH: 20
<212> TYPE: DNA
<213> ORGANISM: Artificial Sequence
<220> FEATURE:
<223> OTHER INFORMATION: Forward primer for real-time RT-PCR analysis of OsICDH1 gene

<400> SEQUENCE: 42
caaaaaggag gcgaaactag                20

<210> SEQ ID NO 43
<211> LENGTH: 23
<212> TYPE: DNA
<213> ORGANISM: Artificial Sequence
<220> FEATURE:
<223> OTHER INFORMATION: Reverse primer for real-time RT-PCR analysis of OsICDH1 gene

<400> SEQUENCE: 43
catgtacaag aagagctaga tcc                                            23

<210> SEQ ID NO 44
<211> LENGTH: 18
<212> TYPE: DNA
<213> ORGANISM: Artificial Sequence
<220> FEATURE:
<223> OTHER INFORMATION: Forward primer for real-time RT-PCR analysis of
      OsMtN3L gene

<400> SEQUENCE: 44
tgaaggccaa atcgaccg                                                  18

<210> SEQ ID NO 45
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsMtN3L gene

<400> SEQUENCE: 45
gaagtccata ccacaggcag                                                20

<210> SEQ ID NO 46
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsDN-DTP6 gene

<400> SEQUENCE: 46
ttgggacgct tcgagattg                                                 19

<210> SEQ ID NO 47
<211> LENGTH: 25
<212> TYPE: DNA
<213> ORGANISM: Artificial Sequence
<220> FEATURE:
<223> OTHER INFORMATION: Reverse primer for real-time RT-PCR analysis of
      OsDN-DTP6 gene

<400> SEQUENCE: 47
atctggtccg gagtaagata atttc                                          25

<210> SEQ ID NO 48
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsANKL1 gene

<400> SEQUENCE: 48 ggtatccctga gctatcgcaa ac                                            22

<210> SEQ ID NO 49
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsANKL1 gene

<400> SEQUENCE: 49
ttccacgtga acaggagaac                                                20

```
<210> SEQ ID NO 50
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsMBD2 gene

<400> SEQUENCE: 50
cataccctgt agacttgcac c                                              21

<210> SEQ ID NO 51
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsMBD2 gene

<400> SEQUENCE: 51
cgccctcgtt tcatagtttt c                                              21

<210> SEQ ID NO 52
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsTP1 gene

<400> SEQUENCE: 52
tgcagttcca gaggtctttg                                                20

<210> SEQ ID NO 53
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsTP1 gene

<400> SEQUENCE: 53
atcacacgtc catggctg                                                  18

<210> SEQ ID NO 54
<211> LENGTH: 20
<212> TYPE: DNA
<213> ORGANISM: Artificial Sequence
<220> FEATURE:
<223> OTHER INFORMATION: Forward primer for real-time RT-PCR analysis of
      OsACOAT1 gene

<400> SEQUENCE: 54
acgcccatgt gaaagagatc                                                20

<210> SEQ ID NO 55
<211> LENGTH: 20
<212> TYPE: DNA
<213> ORGANISM: Artificial Sequence
<220> FEATURE:
<223> OTHER INFORMATION: Reverse primer for real-time RT-PCR analysis of
      OsACOAT1 gene

<400> SEQUENCE: 55
caagcacgca tcaaccaaag                                                20
```

```
<210> SEQ ID NO 56
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsDN-DTP7 gene

<400> SEQUENCE: 56
gaaagggtat ggctctggta ag                                              22

<210> SEQ ID NO 57
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsDN-DTP7 gene

<400> SEQUENCE: 57
gatgtcagat agtgtgcgag g                                               21
```